United States Patent
De Silva et al.

(10) Patent No.: US 10,227,623 B2
(45) Date of Patent: Mar. 12, 2019

(54) HIGH FORCE AND HIGH STRESS DESTRUCTURING OF CELLULOSIC BIOMASS

(71) Applicant: E I DU PONT DE NEMOURS AND COMPANY, Wilmington, DE (US)

(72) Inventors: Wathudura Indika Namal De Silva, Rahway, NJ (US); Paul Joseph Fagan, Wilmington, DE (US); F Glenn Gallagher, Wilmington, DE (US); Zheng-Zheng Huang, Hockessin, DE (US); Guangliang Gary Liu, Wilmington, DE (US); Aaron Perelman, Wilmington, DE (US); Luis Fernando Romero Millan, Swindon (GB); Anton Shpilsky, Wilmington, DE (US); Daniel A Slanac, Greenville, DE (US); Maria Walsh, Chiseldon (GB)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/546,225

(22) Filed: Nov. 18, 2014

(65) Prior Publication Data
US 2015/0147311 A1 May 28, 2015

Related U.S. Application Data

(60) Provisional application No. 62/014,313, filed on Jun. 19, 2014, provisional application No. 61/908,158, filed on Nov. 24, 2013.

(51) Int. Cl.
| | | |
|---|---|---|
| *C12P 19/14* | (2006.01) | |
| *C08H 8/00* | (2010.01) | |
| *C12P 19/02* | (2006.01) | |
| *A61K 31/717* | (2006.01) | |
| *A61K 38/47* | (2006.01) | |
| *C08B 30/02* | (2006.01) | |
| *C08B 30/12* | (2006.01) | |
| *C12P 7/14* | (2006.01) | |
| *C12P 19/20* | (2006.01) | |
| *C13K 1/02* | (2006.01) | |
| *C12P 7/10* | (2006.01) | |
| *C13K 13/00* | (2006.01) | |
| *A23K 10/30* | (2016.01) | |
| *A23K 20/189* | (2016.01) | |

(52) U.S. Cl.
CPC ............ *C12P 19/14* (2013.01); *A23K 10/30* (2016.05); *A23K 20/189* (2016.05); *A61K 31/717* (2013.01); *A61K 38/47* (2013.01); *C08B 30/02* (2013.01); *C08B 30/12* (2013.01); *C08H 8/00* (2013.01); *C12P 7/10* (2013.01); *C12P 7/14* (2013.01); *C12P 19/02* (2013.01); *C12P 19/20* (2013.01); *C13K 1/02* (2013.01); *C13K 13/002* (2013.01); *C12P 2201/00* (2013.01); *C12Y 302/01004* (2013.01); *Y02E 50/16* (2013.01); *Y02P 60/877* (2015.11)

(58) Field of Classification Search
None
See application file for complete search history.

(56) References Cited

U.S. PATENT DOCUMENTS

| | | | |
|---|---|---|---|
| 5,008,437 A | 4/1991 | Mookherjee et al. | |
| 5,356,812 A | 10/1994 | Matsuyama et al. | |
| 5,370,999 A | * 12/1994 | Stuart ...................... | C08H 8/00 435/105 |
| 5,498,766 A | 3/1996 | Stuart et al. | |
| 5,514,583 A | 5/1996 | Picataggio et al. | |
| 5,686,276 A | 11/1997 | Laffend et al. | |
| 5,712,133 A | 1/1998 | Picataggio et al. | |
| 5,843,760 A | 12/1998 | Zhang et al. | |
| 6,013,494 A | 1/2000 | Nakamura et al. | |
| 6,159,738 A | 12/2000 | Donnelly et al. | |
| 6,228,117 B1 | 5/2001 | De Bruijn et al. | |
| 6,228,630 B1 | 5/2001 | Kofod et al. | |
| 6,423,145 B1 | 7/2002 | Nguyen et al. | |
| 6,514,733 B1 | 2/2003 | Emptage et al. | |
| 6,566,107 B1 | 5/2003 | Zhang | |
| 6,777,207 B2 | 8/2004 | Kjeldsen et al. | |
| 6,861,237 B2 | 3/2005 | Andersen et al. | |
| 6,962,805 B2 | 11/2005 | Asakura et al. | |
| 7,005,291 B1 | 2/2006 | Nair et al. | |
| 7,098,009 B2 | 8/2006 | Shanmugam et al. | |

(Continued)

FOREIGN PATENT DOCUMENTS

| | | | |
|---|---|---|---|
| EP | 136359 | A1 | 4/1985 |
| JP | 47004505 | | 3/1972 |
| JP | 47038995 | | 10/1972 |
| JP | 51006237 | | 1/1976 |

(Continued)

OTHER PUBLICATIONS

Verardi et al., Hydrolysis of Lignocellulosic Biomass: Current Status of Processes and Technologies and Future Perspectives, Bioethanol, Intechopen 2012.*

(Continued)

*Primary Examiner* — Sharmila G Landau
*Assistant Examiner* — Stephen M Chong

(57) ABSTRACT

A process for mechanical destructuring of cellulosic biomass was developed that makes use of a short application of high compression, impact, and shearing forces. The biomass may be destructured using a specific energy input that is less than 40% of the total combustible energy of the biomass. The destructured biomass, with or without saccharification and/or in-feed glycosyl hydrolase enzymes, may be used in feed applications.

40 Claims, 4 Drawing Sheets

(56) References Cited

U.S. PATENT DOCUMENTS

| | | |
|---|---|---|
| 7,223,575 B2 | 5/2007 | Zhang et al. |
| 7,629,151 B2 | 12/2009 | Gold et al. |
| 7,629,156 B2 | 12/2009 | Viitanen et al. |
| 7,642,083 B2 | 1/2010 | Frost et al. |
| 7,708,214 B2 | 5/2010 | Medoff |
| 7,741,119 B2 | 6/2010 | Viitanen et al. |
| 7,781,191 B2 | 8/2010 | Dunson, Jr. et al. |
| 7,819,976 B2 | 10/2010 | Friend et al. |
| 7,851,188 B2 | 12/2010 | Donaldson et al. |
| 7,897,396 B2 | 3/2011 | Caimi et al. |
| 7,910,338 B2 | 3/2011 | Hennessey et al. |
| 7,932,063 B2 | 4/2011 | Dunson, Jr. et al. |
| 7,989,206 B2 | 8/2011 | Viitanen et al. |
| 7,998,713 B2 | 8/2011 | Dunson, Jr. et al. |
| 7,998,722 B2 | 8/2011 | Viitanen et al. |
| 8,206,970 B2 | 6/2012 | Eliot et al. |
| 8,216,809 B2 | 7/2012 | Diner et al. |
| 8,241,873 B2 | 8/2012 | Diner et al. |
| 8,241,880 B2 | 8/2012 | Diner et al. |
| 8,304,213 B2 | 11/2012 | Diner et al. |
| 8,304,535 B2 | 11/2012 | Harmer et al. |
| 8,372,609 B2 | 2/2013 | Sabesan |
| 8,389,253 B2 | 3/2013 | Diner et al. |
| 8,445,236 B2 | 5/2013 | Hennessey et al. |
| 8,460,898 B2 | 6/2013 | Diner et al. |
| 8,512,979 B2 | 8/2013 | Dunson, Jr. et al. |
| 8,524,474 B2 | 9/2013 | Sabesan et al. |
| 8,651,403 B2 | 2/2014 | Camp et al. |
| 8,715,969 B2 | 5/2014 | Sabesan et al. |
| 2003/0170834 A1 | 9/2003 | Gatenby et al. |
| 2007/0292927 A1 | 12/2007 | Donaldson et al. |
| 2008/0182308 A1 | 7/2008 | Donaldson et al. |
| 2009/0042259 A1 | 2/2009 | Dale et al. |
| 2009/0053800 A1 | 2/2009 | Friend et al. |
| 2009/0155870 A1 | 6/2009 | Donaldson et al. |
| 2010/0024810 A1 | 2/2010 | Harmer |
| 2010/0159515 A1 | 6/2010 | Cirakovic |
| 2010/0159517 A1 | 6/2010 | Diner et al. |
| 2010/0159521 A1 | 6/2010 | Cirakovic et al. |
| 2010/0159522 A1 | 6/2010 | Cirakovic et al. |
| 2011/0143408 A1 | 6/2011 | Yang |
| 2011/0250646 A1 | 10/2011 | Bazzana et al. |
| 2011/0318801 A1 | 12/2011 | Kahsay et al. |
| 2011/0318803 A1 | 12/2011 | Hitz et al. |
| 2012/0125551 A1 | 5/2012 | Cohen et al. |
| 2012/0156746 A1 | 6/2012 | Caimi et al. |
| 2014/0131189 A1 | 5/2014 | Gallagher |
| 2014/0131487 A1 | 5/2014 | Gallagher |
| 2014/0131490 A1 | 5/2014 | Gallagher |
| 2014/0131492 A1 | 5/2014 | Gallagher |
| 2014/0273105 A1 | 9/2014 | Cheung |
| 2015/0147786 A1 | 5/2015 | Clarkson et al. |

FOREIGN PATENT DOCUMENTS

| | | |
|---|---|---|
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| WO | 95/28476 A1 | 10/1995 |
| WO | 02/37981 A2 | 5/2002 |
| WO | 2006/113686 A2 | 10/2006 |
| WO | 2006113683 A2 | 10/2006 |
| WO | 2007/044968 A3 | 6/2007 |
| WO | 2009/094418 A2 | 7/2009 |
| WO | 2011/038019 A3 | 12/2011 |

OTHER PUBLICATIONS

Hiroshi Hagino, Control Mechanisms in Aromatic Amino Acid Biosynthesis and the Amino Acid Production, Agric Chem Soc Japan, 50(1) R79-R87, 1976.

Savas Anastassiadis et al., Process Optimization of Continuous Gluconic Acids Fermentation by Isolated Yeast-Like Strains of Aureobasidium pullulans, Biotechnology and Bioengineering, Aug. 20, 2005, pp. 494-501, vol. 91, No. 4.

Abdellatif Barakat et al., Eco-friendly dry chemo-mechanical pretreatments of lignocellulosic biomass: Impact on energy and yield of the enzymatic hydrolysis, Applied Energy, 2014, pp. 97-105, vol. 113.

Munir Cheryan et al., Production of Acetic Acid by Clostridium thermoaceticum, Advances in Applied Microbiology, 1997, pp. 1-33, vol. 43.

Shishir P.S. Chundawat et al., High-Throughput Microplate Technique for Enzymatic Hydrolysis of Lignocellulosic Biomass, Biotechnology and Bioengineering, Apr. 15, 2008, pp. 1281-1294, vol. 99, No. 6.

Mukund V. Deshpande, Ethanol Production from Cellulose by Coupled Saccharification/Fermentation using *Saccharomyces cerevisiae* and Cellulase Complex from Sclerotium rolfsU UV-8 Mutant, Appl. Biochem. Biotechnol, 1992, vol. 36, 227.

P Durre, New insights and novel developments in clostridial acetone/butanol/isopropanol fermentation, Appl. Microbiol Biotechnol., 1998, pp. 639-648, vol. 49.

Mustafa Elfair et al., A Gluconobacter oxydans mutant converting glucose almost quantitatively to 5-keto-D-gluconic acid, Applied Genetics and Molecular Biotechnology, 2005, pp. 668-674, vol. 66.

Sigrun D. Feldmann et al., Pentose metabolism in Zymomonas mobilis wild-type and recombinant strains, Appl. Microbiol Biotechnol, 1992, pp. 354-361, vol. 38.

S. N. Freer, Acetic acid production by Dekkera/Brettanomyces yeasts, World Journal of Microbiology & Biotechnology, 2002, pp. 271-275, vol. 18.

V. Gorenflo et al., Development of a Process for the Biotechnological Large-Scale Production of 4-Hydroxyvalerate-Containing Polyesters and Characterization of Their Physical and Mechanical Properties, Biomacromolecules, 2001, pp. 45-57, vol. 2.

W. J. Groot et al., Technologies for Butanol Recovery Integrated with Fermentations, Process Biochemistry, 1992, pp. 61-75, vol. 27.

Ikram-Ul Haq et al., Optimization of nitrogen for enhanced citric acid productivity by a 2-deoxy D-glucose resistant culture of Aspergillus niger $NG^d$-280, Bioresource Technology, 2005, pp. 645-648, vol. 96.

Riikka Havukainen et al., Covalent Binding of Three Epoxyalkyl Xylosides to the Active Site of ento-1,4-Xylanase II from Trichoderma reesei, Biochemistry, 1996, pp. 9617-9624, vol. 35.

Sandra M. Hick et al., Mechanocatalysis for biomass-derived chemicals and fuels, Green Chem., 2010, pp. 468-474, vol. 12.

Yao-Bing Huang et al., Hydrolysis of cellulose to glucose by solid acid catalysts, Green Chemistry, 2013, pp. 1095-1111, vol. 15.

Peter H. Janssen, Propanol as an end product of threonine fermentation, Arch Microbiol, 2004, pp. 482-486, Vo. 182.

Dharmendra Kumar et al., Effect of cysteine on methionine production by a regulatory mutant of Corynebacterium lilium, Bioresource Technology, 2005, pp. 287-294, vol. 96.

Marko Kuyper et al., Metabolic engineering of a xylose-isomerase-expressing *Saccharomyces cerevisiae* strain for rapid anaerobic xylose fermentation, FMES Yeast Research, 2005, pp. 399-409, vol. 5.

Y. Li et al., Efficient pyruvate production by a multi-vitamin auxotroph of Torulopsis glabrata: key role and optimization of vitamin levels, Appl. Microbiol Biotechnol, 2001, pp. 680-685, vol. 55.

Henry Lin et al., Metabolic engineering of aerobic succinate production systems in *Escherichia coli* to improve process productivity and achieve the maximum theoretical succinate yield, Metabolic Engineering, 2005, pp. 116-127, vol. 7.

Lee R. Lynd et al., Microbial Cellulose Utilization: Fundamentals and Biotechnology, Microbiology and Molecular Biology Reviews, Sep. 2002, pp. 506-577, vol. 66, No. 3.

Akinori Matsushika et al., Ethanol production from xylose in engineered *Saccharomyces cerevisiae* strains: current state and perspectives, Appl. Microbiol Biotechnol, 2009, pp. 37-53, vol. 84.

Peter McKendry et al., Energy production from biomass (part 1): overview of biomass, Bioresource Technology, 2002, pp. 37-46, vol. 83.

(56) References Cited

OTHER PUBLICATIONS

Ali Mohagheghi et al., Performance of a newly developed integrant of Zymomonas mobilis for ethanol production on corn stover hydrolysate, Biotechnology Letters, 2004, pp. 321-325, vol. 26.

Mori et al., Japan Society of Mechanical Engineers collected papers; Note No. 2011-JBM-0582; 78 No. 787 (Mar. 2012).

S. I. Mussatto et al., Xylitol production from high xylose concentration: evaluation of the fermentation in bioreactor under different stirring rates, Journal of Applied Microbiology, 2003, pp. 331-337, vol. 95.

Kiyoshi Nakayama et al., Fermentative Production of L-Arginine, Agr. Biol. Chem., 1972, pp. 1675-1684, vol. 36, No. 10.

Wei Niu et al., Benzene-Free Synthesis of Adipic Acid, Biotechnol Prog., 2002, pp. 201-211, vol. 18.

Kazuyuki Okamoto et al, Development of an Industrially Stable Process for L-Threonine Fermentation by an L-Methionine-Auxotrophic Mutant of *Escherichia coli*, Journal of Bioscience and Bioengineering, 2000, pp. 87-89, vol. 89, No. 1.

C.S.K. Reddy et al., Enhanced production of itaconic acid from corn starch and market refuse fruits by genetically manipulated Aspergillus terreus SKR10, Bioresource Technology, 2002, pp. 69-71, vol. 85.

Om Vir Singh et al., Optimisation of fermentation conditions for bluconic acid production by a mutant of Aspergillus niger, Indian Journal of Experimental Biology, Nov. 2011, pp. 1136-1143, vol. 39.

Supaporn Suwannakham et al., Enhanced Propionic Acid Fermentation by Propionibacterium acidipropionici Mutant Obtained by Adaptation in a Fibrous-Bed Bioreactor, Biotechnology and Bioengineering, Aug. 5. 2005, pp. 325-337, vol. 91, No. 3.

Takahashi et al., Japan Society of Mechanical Engieers collected papers; Note No. 2011-JBR-0845; 78 No. 788 (Apr. 2012).

Abullatif Tay et al., Production of L(+)-Lactic Acid From Glucose and Starch by Immobilized Cells of Rhizopus oryzae in a Rotating Fibrous Bed Bioreactor, Biotechnology and Bioengineering, Oct. 5, 2002, pp. 1-12, vol. 80, No. 1.

S. Ui et al., Production of L-2,3-butanediol by a new pathway constructed in *Escherichia coli*, Letters in Applied Microbiology, 2004, pp. 533-537, vol. 39.

S. A. Underwood et al., Genetic Changes to Optimize Carbon Partitioning between Ethanol and Biosynthesis in Ethanologenic *Escherichia coli*, Applied and Environmental Microbiology, Dec. 2002, p. 6263-6272, vol. 68, No. 12.

Alessandra Verardi et al., Hydrolysis of Lignocellulosic Biomass: Current Status of Processes and Technolgies and Future Perspectives, Bioethanol, Intechopen, 2012; pp. 95-122.

Zetang Wu et al., Extractive Fermentation for Butyric Acid Production From Glucose by Clostridium tyrobutyricum, Biotechnology and Bioengineering, Apr. 5, 2003, pp. 93-102, vol. 82, No. 1.

Atsushi Yokota et al., Pyruvic Acid Production by an $F_1$-ATPase-defective Mutant of *Escherichia coli* W1485lip2, Biosci. Biotech. Biochem, 1994, pp. 2164-2167, vol. 58, No. 12.

Min Zhang et al., Metabolic Engineering of a Pentose Metabolism Pathway in Ethanologenic Zymomonas mobilis, Science, Jan. 13, 1995, pp. 240-243, vol. 267.

Xuebing Zhao et al., Biomass recalcitrance. Part II: Fundamentals of different pre-treatments to increase the enzymatic digestibility of lignocullulose, Biofuels Bioproducts & Biorefining, 2012, pp. 561-579, vol. 6(5).

Shengde Zhou et al., Production of Optically Pure $_D$-Lactic Acid in Mineral Salts Medium by Metabolically Engineered *Escherichia coli* W3110, Applied and Environmental Microbiology, Jan. 2003, pp. 399-407, vol. 69, No. 1.

U.S. Appl. No. 13/297,413, filed Nov. 16, 2011.

International Search Report—PCT/US2014/066835—mailed Feb. 27, 2015.

International Search Report—PCT/US2014/066846—mailed Mar. 4, 2015.

Chundawat, Shishir et al., Effect of Particle Size Based Separation of Milled Corn Stover on AFEX Pretreatment and Enzymatic Digestibility, Biotechnology and Bioengineering, Feb. 1, 2007, pp. 219-231, vol. 96, No. 2.

Dale, Bruce E. et al., Extrusion Processing for Ammonia Fiber Explosion (AFEX), Applied Biochemistry and Biotechnology, 1999, pp. 35-45, vol. 77-79.

Taylor, Frank et al., Corn-Milling Pretreatment and Anhydrous Ammonia, Applied Biochemistry and Biotechnology, 2003, pp. 141-148, vol. 104.

Bals, Bryan et al., Evaluation of ammonia fibre expansion (AFEX) pretreatment for enzymatic hydrolysis of switchgrass harvested in different seasons and locations, Biotechnology and Biofuels, 2010, pp. 1-11, vol. 3, No. 1.

Banerjee, Goutami et al., Synthetic Enzyme Mixtures for Biomass Deconstruction: Production and Optimization of a Core Set, Biotechnology and Bioengineering, Aug. 1, 2010, pp. 707-720, vol. 106.

Kabeya, Hiroshi et al., Shikoku Kogyo Gijutsu Shikensho Kenkyu Hokoku, Chapter 4: Chemical and Physical Pretreatments for Enhancement of the Enzymatic Hydrolysis of Thermomechanical Pulp, 1993, pp. 42-90, vol. 24.

Cheetham et al., 'Variation in crystalline type with amylose content in maize starch granules: an X-ray powder diffraction study,' Carbohydrate Polymers, 1998, vol. 36, pp. 277-284.

Nara et al., 'Studies on the relationship between water-satured state and crystallinity by the diffraction method for moistened potato starch,' Starch, 1983, vol. 35, pp. 407-410.

Zhang et al., 'Synthesis of multiresponsive and dynamic chitosan-based hydrogels for controlled release of bioactive molecules,' Biomacromolecules, 2011, vol. 12, pp. 2894-2901.

\* cited by examiner

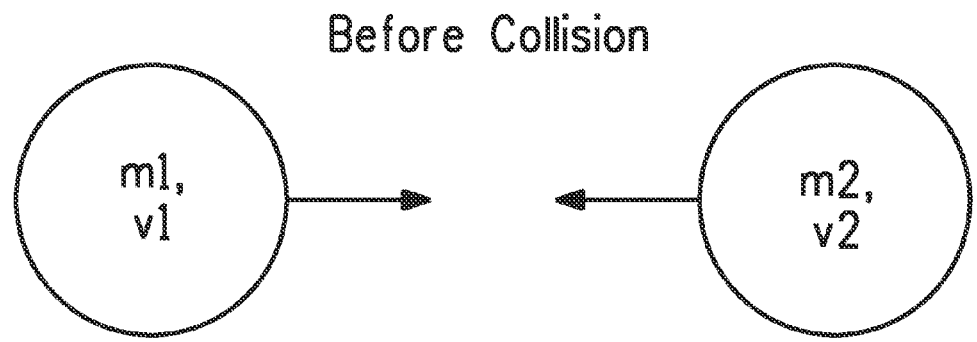
FIG. 2A
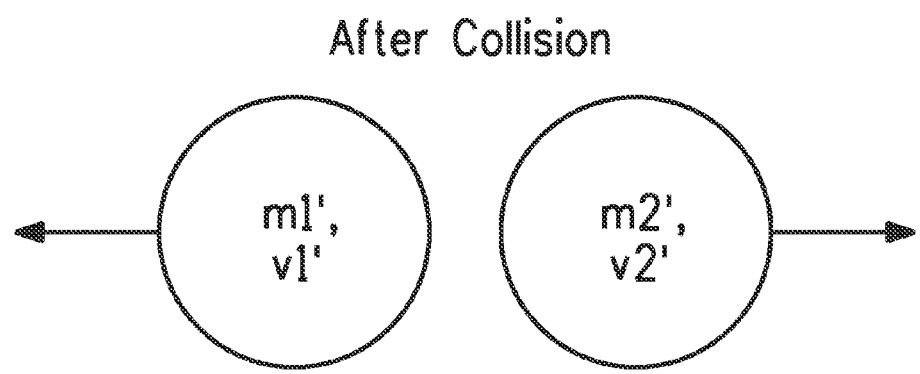
FIG. 2B
$$F = m\Delta v/\Delta t$$
FIG. 2C
FIG. 2

HIGH FORCE AND HIGH STRESS DESTRUCTURING OF CELLULOSIC BIOMASS

This application claims the benefit of U.S. Provisional Applications 61/908,158 and 62/014,313, filed Nov. 24, 2013 and Jun. 19, 2014, respectively, which are incorporated in their entirety herein by reference.

FIELD OF THE INVENTION

Processes for producing destructured cellulosic biomass are provided. Specifically, cellulosic biomass is processed using high compression, impact, and shearing forces with relatively low energy input, thereby producing a destructured cellulosic biomass that is digestible and from which sugars can be obtained.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, containing carbohydrate polymers comprising cellulose, hemicellulose, and lignin are generally treated by a variety of chemical, mechanical and enzymatic means to release primarily hexose and pentose sugars, which can then be converted to useful products with processes such as thermal, enzymatic, chemical, and/or biological treatments.

Impediments to release of sugars from cellulosic biomass include its protection by lignin and cellulose crystallinity. Pretreatment methods, including steam explosion, hot water, dilute acid, ammonia fiber explosion, alkaline hydrolysis, oxidative delignification and organosolv (Zhao et al. (2012); Biofuels, Bioproducts and Biorefining 6(5): 561-579), are often used to make the carbohydrate polymers of cellulosic and lignocellulosic materials more available for saccharification. Mechanical size reduction is often used in combination with chemical treatments to make cellulosic biomass amenable to saccharification, primarily to create more surface area of the biomass to speed up reactions. Costs of chemicals, chemical recovery, energy inputs, and capital equipment make many pretreatment methods not amenable to commercial production.

Using mechanical treatment alone prior to saccharification, where only size reduction takes place, does not eliminate the aforementioned issues that hinder sugars release: protection by lignin and cellulose crystallinity. However, mechanical treatment alone has been used to affect the cellulose crystallinity thereby increasing release of sugars, but typically requires high energy input. Hick et. al (Green Chemistry (2010) 12(3): 468-474) experimentally show that at small scale (1 gram batches) shaker mills, wherein spherical media are shaken with material inside of a container, can sufficiently destructure cellulose for full enzymatic release of glucose, but at energies upwards of ~500 kJ/g, which is ~25× the combustion energy of the biomass (~17-22 kJ/g) (McKendry Bioresource Technology (2002) 83(1) p 37-46). Larger scale stirred ball mills (1 kg) can achieve a 5× reduction in specific energy to ~100 kJ/kg. Simulated results of larger scale attrition milling (stirred ball milling) (100 kg) predict energies >15 kJ/g, or at least 75% the energy of the biomass.

In an attempt to create a more energy efficient mechanical process for the release of sugars, Takahashi et al. (Japan Society of Mechanical Engineers collected papers; Note No. 2011-JBR-0845; 78 No. 788 (2012-4)) use a gear type grinding-media mill. The biomass was milled in batch inside a cylindrical chamber that vibrates around a central axis. Circular gears are placed inside the cylindrical chamber as free flowing media, and are allowed to freely move around inside the container as the container vibrates, causing a grinding action against the wall. Biomass particle size diameter was reduced on average from 55 μm to 20 μm in 20 minutes, and the saccharification efficiency of holocellulose (combined cellulose and hemicellulose) reached around 70% at pulverizing time of 60 minutes. The specific energies required to achieve the sugar yield above still required ~40-103 kJ/g. In a similar report by Mori et al. (Japan Society of Mechanical Engineers collected papers; Note No. 2011-JBN-0582; 78 No. 787 (2012-3)), biomass was continuously processed in a continuous high-impact pulverizing vibration mill without the use of gears, but using smooth surfaced rings. The saccharification efficiency of holocellulose reached ~50% at pulverizing time of 60 minutes for a continuous pulverizing process and about 65% for a batch process run for 60 minutes. These lower sugars yields still required a specific energy of ~8-10 kJ/g, which is ~40% of the combustible energy of the biomass. Stresses on the material reach almost 20,000 psi (137.9 MPa), and the force applied is <5,000 N.

There remains a need for lignocellulosic biomass pretreatment processes that use lower specific energies to create destructured cellulosic biomass from which sugars can be obtained. Such processes can reduce energy costs and increase investment productivity relative to alternative strategies.

SUMMARY OF THE INVENTION

The invention provides a process for pretreating cellulosic biomass in preparation for saccharification or combining with in-feed glycosyl hydrolase enzyme(s) or a combination of both.

Accordingly, the invention provides a process for producing destructured cellulosic biomass comprising:
a) providing a portion of cellulosic biomass; and
b) applying to the biomass of (a) at least one set of compression and impact forces of at least 5,000 N combined with shearing forces;
wherein contact stress of greater than 5,000 psi is applied to the biomass and wherein a destructured cellulosic biomass is produced.

In another embodiment the invention provides a process for producing destructured cellulosic biomass comprising:
a) providing a portion of cellulosic biomass; and
b) applying to the biomass of (a) at least one set of compression and impact forces of at least 1,500 N combined with shearing forces, and contact stress of greater than 5,000 psi;
wherein specific energy input in the process is less than 40% of the total combustible energy of the portion of biomass being treated and wherein a destructured cellulosic biomass is produced.

In yet another embodiment the invention provides cellulosic biomass produced by the process above comprising cellulose having a coherent domain size that is less than about 2.5 nm and having a processed energy equivalency of greater than 60%.

In additional embodiments the invention provides a feed additive composition comprising destructured biomass produced by the process above, a feed additive composition comprising the destructured biomass in combination with at least one in-feed glycosyl hydrolase enzyme, and a feed additive kit, feed or feedstuff, or premix comprising the destructured biomass or the destructured biomass in combination with at least one in-feed glycosyl hydrolase enzyme, and at least one mineral and/or at least one vitamin.

In further embodiments the invention provides a method for improving a biophysical characteristic of an animal comprising administering to an animal said feed additive composition or said premix, using said feed additive composition or said premix for improving a biophysical characteristic of an animal, and a method of preparing a feedstuff comprising contacting a feed component with said feed additive composition.

BRIEF DESCRIPTION OF THE DRAWINGS

FIG. 2 is a diagram of the particle size reduction mechanism in a jet mill.

FIG. 2A shows particles before collision.

FIG. 2B shows particles after collision.

FIG. 2C gives the equation used to calculate the force of the collision impact.

DETAILED DESCRIPTION

Figure 1:
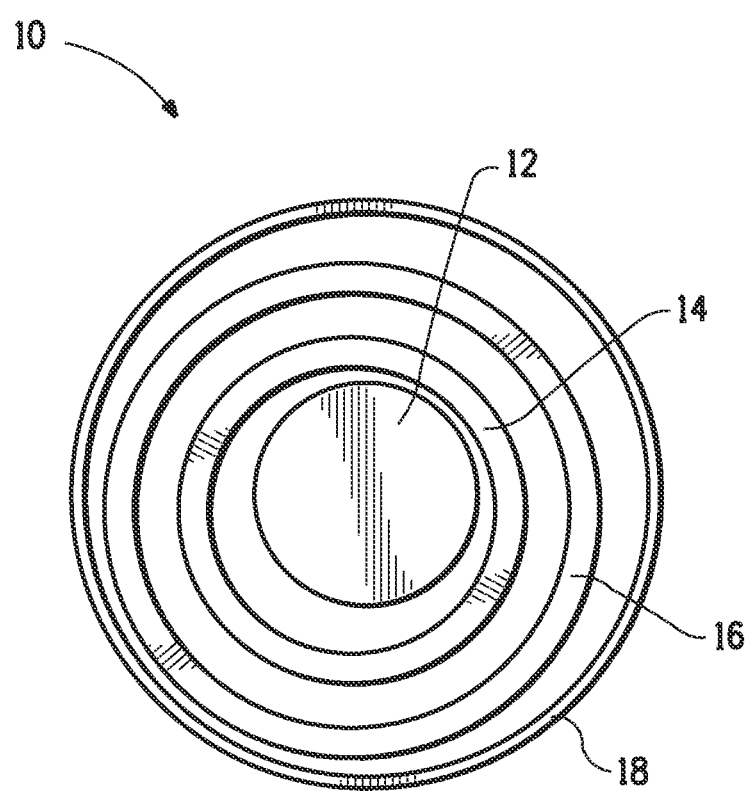
FIG. 1 is a diagram of an apparatus for imparting compression and impact forces using centrifugal motion.

The invention relates to a process for pretreating cellulosic biomass with high force and a low input of mechanical energy where a destructured biomass product is made. The destructured biomass product may be saccharified producing sugars which may be used in production of desired target products, such as through fermentation using a biocatalyst or by reacting with a chemical catalyst. Alternatively the saccharified destructured biomass (also referred to herein as biomass hydrolysate) may be used as an animal feed or as a feed additive composition. The destructured biomass product or the sacchariifed destructured biomass product (e.g the biomass hydrolysate) may be admixed or combined with at least one in-feed glycosyl hydrolase enzyme prior to feeding to an animal.

The following definitions and abbreviations are to be used for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "fermentable sugar" refers to oligosaccharides and monosaccharides that can be used as a carbon source by a microorganism in a fermentation process.

The term "lignocellulosic" describes to a composition comprising both lignin and at least 10 wt % cellulose. Lignocellulosic material may also comprise hemicellulose.

The term "cellulosic" describes a composition comprising at least 10 wt % cellulose or cellulose plus hemicellulose. Cellulosic material may also include lignin. Thus lignocellulosic material is a type of cellulosic material. Cellulosic also refers to compositions enriched in cellulose and/or hemicellulose obtained from processing of grains, including but not limited to grain fractions (for example a fiber fraction), by-products (for example whole stillage, wet cake, distillers dry grains (DDG) or distillers dry grains with solubles (DDGS)), biomass post any liquefaction, saccharification, fermentation, SSF and/or other process or treatment.

The term "saccharification" refers to the production of sugars from polysaccharides. Saccharification may be by any method including enzymatic digestion and chemical treatment.

The term "pretreated biomass" means biomass that has been subjected to pretreatment prior to saccharification.

The term "destructured" when applied to cellulosic biomass refers to a biomass having reduced length over which crystalline order is observed, which is called the coherent domain size.

As used herein the term "compression force" refers to the application of inward ("pushing") forces to different points on a material or structure, that is, forces with no net sum or torque directed so as to reduce its size in one or more directions. Compression force is applied between two surfaces where equal and opposite force vectors are generated normal to the curvature of the surfaces.

As used herein an "impact force" is a high force or shock applied over a short time period when two or more bodies collide. For example, when a compressive force is applied over a short period of time, this is considered as an impact force. As used herein, the impact force is a force resulting from a fast compression between surfaces. It is a mode of applying an impact force that is different from a mode where force is generated by only one surface effectively applying a force on a material (e.g. a swinging hammer hitting material in a hammer mill). Hammer milling or jet milling are types of milling that are used herein for comparative purposes and do not result in destructured cellulosic biomass in accordance with the present invention. These are used as control treatments in the examples referred to herein.

As used herein the term "milling media" refers to any grinding surface inside the confines of a mill's grinding chamber, that does not include the chamber itself, including but not limited to balls in a ball mill, rods in a rod mill, the rollers in a ring-roller mill employing centrifugal force, the rollers in a ring-roller mill employing spring and/or hydraulic force, rings and puck in a puck mill, and gears in a gear-type grinding media mill.

The term "G-force" as used herein refers to the ratio of the actual acceleration to the gravitational acceleration, where the gravitational acceleration is ~9.8 m/s$^2$. For example, if the acceleration of the milling media is calculated to be ~60 m/s$^2$, then the corresponding "G-force" is ~6 G.

The term "cellulosic biomass" refers to any cellulosic or lignocellulosic material containing at least 10 wt % cellulose and includes materials comprising cellulose, and optionally further comprising hemicellulose, lignin, starch, oligosaccharides and/or monosaccharides. Cellulosic biomass may also comprise additional components, such as protein and/or lipid. According to the invention, cellulosic biomass may be derived from a single source, or cellulosic biomass can comprise a mixture derived from more than one source; for example, cellulosic biomass could comprise a mixture of corn cobs and corn stover, or a mixture of grass and leaves. In addition, a cellulosic biomass mixture may contain cellulosic biomass and non-cellulosic biomass, where the cellulose content of the mixture is at least 10%. Cellulosic biomass includes, but is not limited to, bioenergy crops, agricultural residues, municipal solid waste, industrial solid waste, sludge from paper manufacture, yard waste, wood and forestry waste or a combination thereof. Examples of cellulosic biomass include, but are not limited to, corn cobs, crop residues such as corn husks, corn stover, corn grain fiber, grasses, wheat, wheat straw, barley, barley straw, hay, rice straw, switchgrass, waste paper, sugar cane bagasse, sorghum, soy, components obtained from milling of grains or from using grains in production processes (such as corn fiber fraction, DDGS: dried distillers grains with solubles), trees, branches, roots, leaves, wood chips, sawdust, shrubs and bushes, vegetables, fruits, flowers, and animal manure or a combination thereof.

The term "biomass hydrolysate" refers to the product resulting from saccharification of biomass. The biomass may also be pretreated or pre-processed prior to saccharification.

"Enzyme consortium" or "saccharification enzyme consortium" is a collection of enzymes, usually secreted by microorganisms, which in the present case will typically contain one or more cellulases, xylanases, glycosidases, ligninases and esterases.

The term "target compound" refers to any product that is produced by a microbial production host cell in a fermentation. Target compounds may be the result of genetically engineered enzymatic pathways in host cells or may be produced by endogenous pathways. In addition, target compounds may be produced via chemical reaction with or without a chemical catalyst. Typical target compounds include but are not limited to acids, alcohols, alkanes, alkenes, aromatics, aldehydes, ketones, biopolymers, proteins, peptides, amino acids, vitamins, antibiotics, and pharmaceuticals.

The term "coherent domain size" refers to the average distance (length) over which crystalline order is observed in cellulose, that is, the cellulose crystalline size that is free of structural defects.

The term "crystalline fraction" or "crystallinity fraction" refers to volume ratio of the crystalline portion of cellulose to the total volume of cellulose (including both amorphous and crystalline regions).

The term "yield" with respect to sugars refers to the amount obtained as a percentage of the total calculated amount.

The term "processed energy equivalency" refers to an energy percentage that is determined by the ratio of the difference of the combustible energy of the input material minus the energy used in processing of the material to the combustible energy of the input material.

As used herein, "destructured biomass" refers to destructured cellulosic (including lignocellulosic) biomass.

Pretreatment Using High Force and High Stress Milling

In the present process, cellulosic biomass (including lignocellulosic biomass) is treated (e.g. in preparation for saccharification or in preparation for combining with in-feed glycosyl hydrolase enzymes or a combination thereof) using mechanical forces. The present process performs mechanical destructuring of the cellulosic biomass such that it produces a destructured biomass product. The present mechanical destructuring is effective with a short period of application for the required power, thereby providing a process that requires relatively low energy input in support of a commercially effective cellulosic biomass pretreatment process.

Cellulosic biomass refers to any cellulosic or lignocellulosic material which contains at least 10% cellulose, for example, bioenergy crops, agricultural residues, municipal solid waste, industrial solid waste, yard waste, wood, forestry waste and combinations thereof. In particular, cellulosic biomass may include corn stover, corn cob, corn grain fiber, grasses, beet pulp, wheat straw, wheat chaff, oat straw, barley straw, barley hulls, hay, rice straw, rice hulls, switchgrass, *miscanthus*, cord grass, reed canary grass, waste paper, sugar cane bagasse, sorghum bagasse, sorghum stover, soybean stover, components obtained from milling of grains, or from using grains in production processes (such as DDGS: dried distillers grains with solubles), trees, branches, roots, leaves, wood chips, sawdust, palm waste, shrubs and bushes, vegetables, fruits, flowers and animal manure.

In various embodiments the cellulosic biomass may be size reduced, such as by hammer milling, shredding, chopping, chipping, disc refining, and/or cutting. Particles of cellulosic biomass used may be from very small, in the micron range (i.e. 1-999 microns), to much larger, with at least one dimension on the order of centimeters. In some embodiments an advantage of the present process is its applicability to the use of cellulosic biomass that has particles with at least one dimension in the one to ten centimeter size range, thereby requiring less prior size reduction. For example, in various embodiments the particle size in at least one dimension may be at least about 0.25 inches (0.635 cm), 0.5 inches (1.27 cm), one inch (2.54 cm), 1.5 inches (3.81 cm), 2 inches (5.08 cm), 2.5 inches (6.35 cm), or three inches (7.62 cm). In other embodiments the size may be even larger.

In addition, the cellulosic biomass may be dried, such as air dried or dried with heat and optionally with vacuum. The moisture content of cellulosic biomass used in the present process is generally less than 30%. Typically the moisture content of cellulosic biomass used in the present process is less than 20%, 15%, 10%, or less. Typical moisture content of dried cellulosic biomass is about 7% to about 8%. The moisture content is low enough to provide a friability to the biomass. Techniques such as freezing may be employed to increase the brittleness/friability of the cellulosic biomass to allow for milling of high moisture content biomass.

The mechanical forces applied to the cellulosic biomass are compression and impact forces that result in normal and shear stresses. Stress may be generated by rolling action against a surface, wherein forces are applied by rolling a mass over material against a surface, where sandwiching the material between the mass and the surface creates an anisotropic stress distribution (i.e. shearing, sudden compression (impact) and decompression). The mass is generally referred to as a media. Types of media that may be used to apply compression and impact forces include, but are not limited to, a puck, a ring, a roller, a rod, a disc, and a sphere.

The particles that are ground via these mechanisms may also shear against one another for additional destructuring. In one embodiment the forces applied are of at least about 5,000 N, with stresses of at least 5,000 psi. There may be one level of force applied, or more than one level of force which may be applied concurrently. For example, there may be multiple media that apply forces of different strengths, as described below and shown in FIG. 1. In the case of multiple forces, included are forces of at least about 5,000 N with stresses of at least 5,000 psi. There may be additional lower forces (as well as stresses) applied concurrently. In one embodiment, whether a single level or multiple levels of forces are applied, the forces include a level of at least about 7,000 N combined with stresses of at least 5,000 psi. In other embodiments with single or multiple forces, the forces include a level of at least about 10,000, 12,000, 15,000, 20,000, 25,000, 50,000, 100,000 N or greater combined with stresses of at least about 5,000, 8,000, 13,000, 15,000, 18,000, 20,000, 22,000, or 25,000 psi. In the present process these forces are imparted via a non-vibratory apparatus which does not contain any free flowing media. Media of an apparatus used in the present process are attached to a support, and the described forces are generated using centrifugal, hydraulic, or spring mechanisms and applied to the media and/or a grinding surface.

For illustrative purposes, a diagram of a small scale apparatus for imparting compression, impact and shear forces using centrifugal motion is shown in FIG. 1. This apparatus is a vibratory mill which has free flowing media. A top view of the apparatus is shown (10). A puck (12) is centrally located in a chamber (18) which is attached to an eccentric motor. Two rings (14 and 16) surround the puck, one inside the other, in the chamber (18). When driven by the eccentric motor, the puck and rings produce centrifugal motion, applying compression and impact forces to biomass contained within the chamber.

An example of a non-vibratory apparatus without free flowing media for imparting compression, impact and shear forces that may be used in the present process is a ring-roller mill (Perry's Chemical Engineers' Handbook, 8$^{th}$ Edition, p 21-60). One mill of this type which generates centrifugal force is a centrifugal force roller mill.

In one embodiment, force is applied through centrifugal motion in a centrifugal force roller mill using at least one grinding medium that is attached to a rotating shaft. The grinding medium revolves around the rotating shaft with an angular frequency to create a centrifugal force and swings against a grinding surface thereby applying compression, impact, and shearing forces to cellulosic biomass which is between the medium and grinding surface in the apparatus. In one embodiment the medium is an object with a mass of at least 100 kilograms.

Figure 3A:
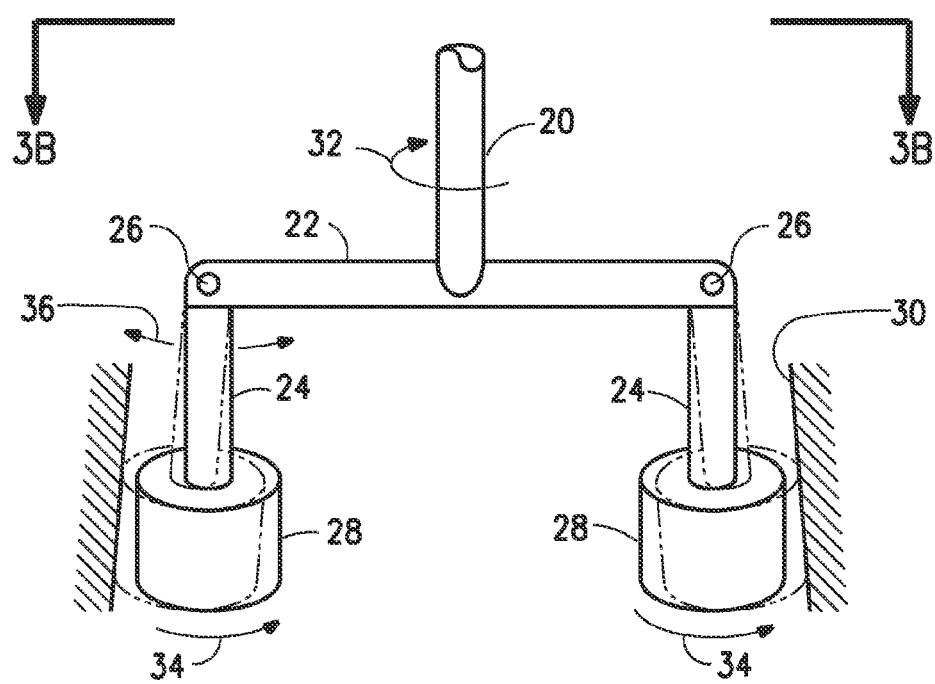
FIG. 3A is a diagram of a side view of a ring-roller mill that employs centrifugal force between revolving milling media and a grinding surface.
Figure 3B:
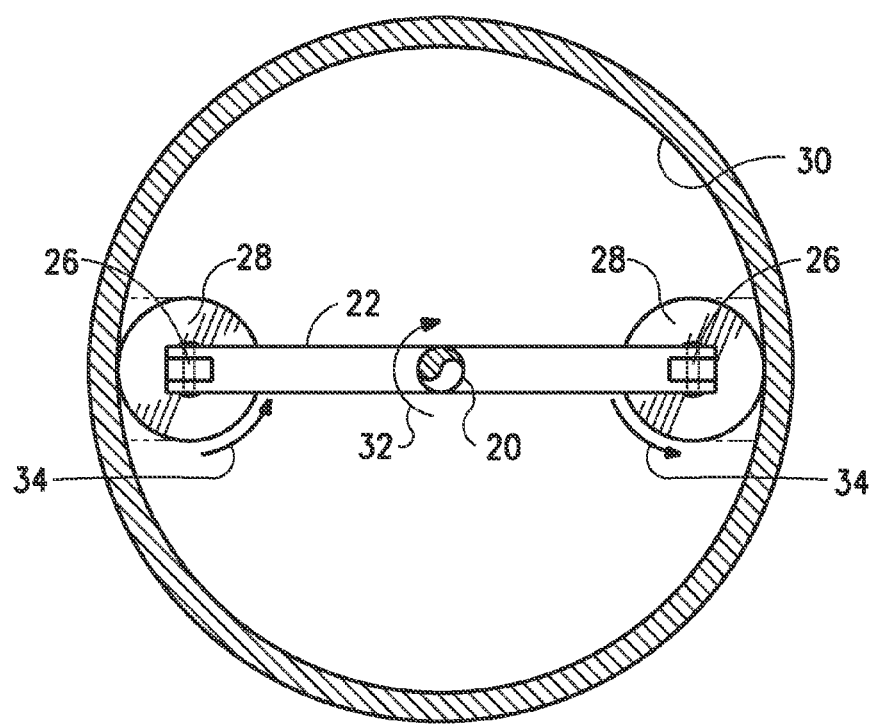
FIG. 3B is a diagram of a top view of a ring-roller mill that employs centrifugal force between revolving milling media and a grinding surface.

An example of this apparatus is shown in FIG. 3, with a side view in A and a top view in B (the two arrows labeled 3B in A show the region of the top view). A drive shaft (20) that rotates (32) is attached to a cross bar (22) that has a hinge (26) at each end. The hinge at each end attaches a rod (24) to the cross bar. Attached to the rod is a roller (28) which rotates (34). As the shaft turns, the rod swings (36) at the hinge and the roller contacts the grinding surface (30). In FIG. 3B is shown that the grinding surface (30) is a continuous ring that the rollers continuously make contact with as the drive shaft (20) rotates. The shape of the roller can be tapered in any manner and the grinding surface can be angled in any manner such that when the drive shaft rotates and the rollers swing out, the roller makes contact with the grinding surface. Contact may be either over the total surface of the roller, or over a substantial portion of the surface of the roller. Preferably, the contact is substantially uniform along the length of the roller.

The centrifugal force of this type of mill is related to the mass of the medium, the center-of-mass radius of the medium, and the angular frequency of rotation, as described in Equation 1, and will vary depending on these aspects of an apparatus used in the present process. The magnitude of centrifugal force [N] is described by:

$$F = mr\omega^2 \qquad \text{Equation 1}$$

where m represents the mass [kg] of the media, r represents the center-of-mass radius of the media [m], and ω represents the angular frequency [rad/s] of rotation.

From the Hertzian contact equations, the contact stress formed by contact of two cylinders is calculable. For a concave cylinder (ring) and a convex cylinder (roller) the calculation of the Hertzian contact half-width, b, and stress, $\sigma_H$, is calculated by the following equations:

$$b = \sqrt{\frac{2F}{\pi l}} \times \sqrt{\frac{\frac{(1-v_1^2)}{E_1} + \frac{(1-v_2^2)}{E_2}}{\frac{1}{d_1} - \frac{1}{d_2}}} \qquad \text{Equation 2}$$

$$\sigma_H = \sqrt{\frac{2F}{\pi l}} \times \sqrt{\frac{\frac{1}{d_1} - \frac{1}{d_2}}{\frac{(1-v_1^2)}{E_1} + \frac{(1-v_2^2)}{E_2}}} \qquad \text{Equation 3}$$

Where F is the force between the two cylinders (centrifugal force in this case), $E_1$ and $E_2$ are the elastic moduli for the roller and ring, respectively, $d_1$ and $d_2$ are the diameters of the convex and concave surfaces (e.g. roller and ring (or chamber)), respectively, l is the contact length along the cylinders, and $v_1$ and $v_2$ are the Poisson ratios for the roller and ring, respectively.

In an apparatus with low masses of rollers and low center of mass radii, the G-forces required to achieve a desired force are high, (for example, greater than 15 G) such as a combination of ~1,500 N and G-forces of 21.5 G. However lower G-force is desired to reduce the power requirement. In one embodiment an apparatus applies to the cellulosic biomass greater than 5,000 N and the G-force is less than 10 G. In another embodiment an apparatus applies to the cellulosic biomass at least about 10,000 N and the G-force is about 5 G.

A centrifugal force roller mill can contain a wide variety of dimensions based on the scale of the operation, such as a ring diameter of between about 12 and 120 inches, roller diameters of between about 4 and 40 inches, and heights of the ring and roller of between about 3 and 30 inches. Mills with different dimensions can be operated with rpm values from about 50 to about 500 rpm. A mill used in the present process additionally may be equipped with a gas conveying system with a recycle classifier and cyclone for product recovery. The gas composition and feed rate may be adjusted to prevent dust explosions. One skilled in the art can choose the mill size, rpm, and required motors to drive the mill to obtain the desired force, which is governed by Equation 1 above. The residence time in the mill can be tuned by modifying classifier and air handling systems, to ensure that the lignocellulosic material that exits the mill contains destructured cellulose. One of skill in the art can modify the system to achieve the required force, residence time, and power input to achieve energy input of less than 40% of the starting total combustible energy of the input cellulosic biomass.

To achieve processed energy equivalency greater than 60% for cellulosic biomass, mill dimensions are tailored to reach high performance in a centrifugal force roller mill. The ratio between the radius of the media and radius of the ring or chamber, herein referred to as Radii Ratio, is a defining parameter in stress calculations (Equation 4).

$$\text{RadiiRatio} = \text{radius}_{media}/\text{radius}_{chamber} \quad \text{Equation 4}$$

When operating the roller mill with high centrifugal force, a preferred geometric arrangement for any force magnitude is when the Radii Ratio equals 1:3 (0.33). At a Radii Ratio of 0.33 the pressure reaches a maximum. For a non-vibratory mill with a central driving shaft, the maximum Radii Ratio is ~1:2 (0.5), defined by the distance between the chamber radius and the central shaft. Thus in the present process wherein centrifugal motion is used to impart the described forces, the Radii Ratio is less than 0.5. In one embodiment the Radii Ratio is less than 0.4, In one embodiment the Radii Ratio is about 0.33, which is used to achieve maximal pressure.

Mill dimensions that approximately represent a Radii Ratio of 1:3 are desired to achieve an energy equivalency greater than 60% for processed cellulosic biomass. In one embodiment, the mill cfRRM-1 in Table 15 represents a mill with a chamber diameter of 40 inches, roller height of 10 inches, and operates at 90 rpm. For this fixed rpm, roller height, and chamber diameter, the optimal roller radius to achieve a peak pressure would be 6.67 inches (16.94 cm) (Radii Ratio=1/3 or 0.33). The minimum Radii Ratio for the cfRRM-1's fixed ring diameter, roller height, and rpm would be 0.3129 to achieve a minimum of 5,000 N and 5,000 psi (34.47 MPa). The centrifugal force on the system can be changed by increasing or decreasing the contact length of the mass-ring interface (i.e. making the roller and grinding surface longer). For example, increasing the contact length effectively increases the mass of the roller and hence increases the centrifugal force (assuming all else is constant, see Equation 1). Changing of the contact length while all else is kept constant will not affect the Hertzian stress calculation.

In another embodiment, the mill cfRRM-4 in Table 15 represents a mill with a chamber diameter of 100 inches, roller height of 29.2 inches, and operates at 100 rpm. For the fixed rpm, roller height, and chamber diameter, the optimal roller radius to achieve a peak pressure would be 16.67 inches (42.34 cm) (Radii Ratio=1/3 or 0.33). The minimum Radii Ratio for the cfRRM-4's fixed ring diameter, roller height, and rpm would be 0.0610 to achieve a minimum of 5,000 N and 5,000 psi (34.47 MPa).

With an optimized Radii Ratio, such as those in Table 15, much higher forces and stresses can be achieved. In various embodiments the stress is greater than about 5,000, 8,000, 13,000, 15,000, 18,000, 20,000, 22,000, or 25,000 psi (34.37, 55.16, 89.63, 103.42, 124.11, 137.90, 151.68, 172.37 MPa).

Equation 6 shows a modified Hertzian equation from Equation 3, which illustrates the embodiments mentioned above. Equation 6 is derived from combining Equations 4 and 5 with Equation 3, to yield a simplified equation relating Hertzian contact theory to the Radii Ratio that defines a mill.

$$F = \pi * (\text{radius}_{mass})^2 * l * (\text{radius}_{chamber} - \text{radius}_{mass}) * \omega^2 \quad \text{Equation 5}$$

$$\text{Pressure} = \text{radius}_{chamber} * \omega * \sqrt{\frac{\rho * \text{ratio} * (\text{ratio} - 1)^2}{\frac{(1 - v_1^2)}{E_1} + \frac{(1 - v_2^2)}{E_2}}} \quad \text{Equation 6}$$

In another embodiment, the force is applied using spring and/or hydraulic mechanisms. An apparatus for applying force in this manner typically has one or more milling media (e.g. rollers) that are forced against a grinding surface (e.g. a ring). The apparatus may function by moving the grinding surface (such as by rotating a shaft to which the ring is attached) while the grinding media remain motionless, which causes material to be fed through and ground between the media and the surface. An apparatus of this type is available commercially such as from FLSmidth (Bethlehem, Pa.), ALSTOM Power Inc. (Windsor, Conn.), and Babcock & Wilcox (Charlotte, N.C.). Alternatively, this type of apparatus may function by moving grinding media attached to a central rotating shaft and keeping the grinding ring stationary. Further, both the media and the surface may move, but motion relative to each other is required to cause grinding.

In one embodiment each individual application of force occurs in less than ten milliseconds. More typically, each individual application of force occurs in between 1 and 200 microseconds. In one embodiment the compression, impact, and shearing forces are applied with a specific energy input that is less than 40% of the total combustible energy of the cellulosic biomass being treated, as further described below. A low energy input is achieved by application of the described high forces together with a throughput of cellulosic biomass that achieves a power draw that is less than 40% of the total combustible energy of the cellulosic biomass being treated. The high forces (>5,000 N) are used to achieve a stress of at least 5,000 psi. This process performs mechanical destructuring of the cellulosic biomass such that it produces a destructured biomass product. At constant power, for lower time periods over which forces are applied, the specific energy requirement is lowered compared to methods requiring longer times, thereby providing a more cost-effective, energy-efficient pretreatment process.

In one embodiment the compression and impact forces applied to the cellulosic biomass are applied by surfaces which are not intentionally textured as in a cog ring or gear type media. Thus the surfaces of the media and the grinding surface are considered to be smooth, although there may be imperfections in these surfaces. Owing to the isotropic form of a smooth surface of a circular ring, the wear resistance is expected to be higher.

The specific energy input [kJ/g of dry biomass] required to convert an amount of cellulosic biomass to a destructured product may be calculated by dividing the steady state power output [kW] of the apparatus used by the throughput [g/s]. The power output for any auxiliary equipment required for the operation of the apparatus, such as a blower and classifier, is added to the power output of the mill. The specific energy input is reduced for a high force centrifugal apparatus as compared to other processes.

In the present process the destructured biomass is produced with high compression and impact forces in combination with some shear from the rolling action of the media against a surface. The mechanical energy input that is required to achieve cellulosic biomass destructuring can be compared to the total combustible energy of the biomass. The total combustible energy of the biomass, or higher heating value (HHV) or Gross Calorific Value (GCV), can be measured according to the American Society for Testing and Materials procedure ASTM-D2015. Typical total combustible energy values for biomass are generally between 17,000 and 22,000 kJ/kg of dry biomass (McKendry Bioresource Technology (2002) 83(1) p 37-46), with 18,000 kJ/kg of dry biomass for corn stover and 20,000 kJ/kg of dry biomass for wood. Subtracting the energy input from the total combustible energy of a portion of biomass is used to give the processed energy equivalency of the resulting destructured biomass. Thus when energy input is less than 40% of the total combustible energy of a portion of biomass, the processed energy equivalency of the biomass is greater than 60% of the starting total combustible energy for the portion of biomass. In one embodiment the present process produces destructured cellulosic biomass having a processed energy equivalency of greater than 60%. Energy input may be less than 40%, 35%, 30%, 25% or less, which gives 60%, 65%, 70%, 75% or greater energy equivalency.

In one embodiment energy input of less than 40% of total combustible energy of the biomass feed is used to produce a destructured cellulosic biomass in a ring and puck mill, wherein a force of at least 1,500N creates a stress of greater than 5,000 psi. The force may be at least 1,500, 3,000, 5,000, 10,000, 12,000, 15,000, 20,000, 25,000, 50,000, 100,000 N or greater. The stress may be greater than 5,000, 8,000, 13,000, 15,000, 18,000, 20,000, 22,000, or 25,000 psi. Energy input may be less than 40%, 35%, 30%, 25% or less which gives 60%, 65%, 70%, 75% or greater energy equivalency, respectively.

Pretreatment Combination with Chemical Treatment

In various embodiments the described mechanical destructuring of cellulosic biomass using high forces is combined with treatment with a pretreatment chemical to further enhance processing. Cellulosic biomass may be contacted with a pretreatment chemical prior to, during, or after treatment with the described compression and impact forces. When the pretreatment chemical is present during force application (when added prior to or during treatment), the chemical should not take away the friability of the biomass. When the pretreatment chemical is added after mechanical destructuring it is typically added as a solution. Any chemical may be used which enhances the following processing, such as saccharification. Examples of pretreatment chemicals that may be used include acids such as sulfuric, acetic, hydrochloric, phosphoric, and sulfonic acids, bases such as sodium hydroxide, ammonium hydroxide, ammonia, calcium hydroxide, calcium oxide, magnesium oxide, potassium hydroxide, and sodium carbonate, and solvents such as sulfolane. The biomass and pretreatment chemical mixture may be washed or treated prior to further processing, such as by enzymatic saccharification, to remove the chemical. The mixture may be washed and vacuum filtered.

Alternatively, the mixture may be used directly in further processing. For example, cellulosic biomass may be destructured as described herein, then treated with aqueous ammonia as disclosed in U.S. Pat. No. 7,932,063, which is incorporated herein by reference, then further processed by saccharification and used in fermentation without washing. Saccharification and fermentation may be separate or simultaneous (simultaneous saccharification and fermentation: SSF), or partially simultaneous (a period of saccharification alone followed by combined saccharification and fermentation).

In various embodiments where the destructured cellulosic biomass is not treated with a pretreatment chemical prior to further processing, or is stored prior to further processing, the destructured cellulosic biomass may be treated to reduce or eliminate microorganisms such as bacteria and/or yeast that are present. Thus the destructured cellulosic biomass may be treated with sterilizing agents that can destroy microorganisms, such as heat, irradiation, high pressure, and filtration as wells as various gases and chemicals such as bleach, ozone, chlorine dioxide, chlorine, bromine, iodine, ethylene oxide, or any other agent known to destroy microorganisms.

Destructured Cellulosic Biomass

Cellulosic biomass treated by the described mechanical process has reduced particle size and reduced length over which crystalline order is observed in the cellulose, which is called the coherent domain size. The cellulosic biomass treated by the described mechanical process may be used as a feed additive composition or part of a feed additive composition or as a feedstuff or part of a feedstuff. The biomass is not only reduced in particle size, but is also destructured, which enhances its ability to undergo saccharification and/or for use in combination with in-feed enzymes. In one embodiment the invention provides cellulosic biomass produced by the process described above which has a coherent domain size that less than about 2.5 nm. In some cases the overall crystalline fraction of the cellulose is decreased as well. The destructured biomass typically has a particle size of less than 200 μm. The particle size may be less than 200 μm, 150 μm, 100 μm, 50 μm, or less.

Thus the present process produces destructured cellulosic biomass having a coherent domain size that is less than about 2.5 nm and having a processed energy equivalency of greater than 60%. This treated cellulosic biomass is a destructured material which can be saccharified to produce sugars in higher yields relative to material that has not undergone the present mechanical processing. In some embodiments saccharification of the resulting material produces a combined yield of glucose and glucose oligomers and of xylose and xylose oligomers that is at least about 15% greater on a total possible sugars yield basis (i.e. from 40% to 55% is a 15% yield increase) than the yield from cellulosic biomass that is of similar particle size but has not been destructured.

In various embodiments the resulting material is saccharified to produce sugars and sugar oligomers with a combined yield of glucose, glucose oligomers, xylose, and xylose oligomers of at least about 50%, 55%, 60%, 65%, 70%, 75%, 80%, 85%, or greater of total possible yield of these sugars. In some embodiments the resulting material is saccharified to produce sugars and sugar oligomers, with at least about 50%, 55%, 60%, 65%, 70%, 75%, or 80% yield of glucose and glucose oligomers. In some embodiments the resulting material is saccharified to produce sugars and sugar oligomers, with at least about 50%, 55%, 60%, 65%, 70%, or 74% yield of xylose and xylose oligomers. Embodiments include any combination of glucose and glucose oligomers, and xylose and xylose oligomers produced at any of these levels. The yields of glucose and xylose will depend on the saccharification method used. For example, enzymatic saccharification will typically give the high yield of glucose and a lower yield of xylose, and some chemical saccharification methods will typically give the high yield of xylose and a lower yield of glucose.

Saccharification

Saccharification may be either by enzymatic or chemical treatments. In one embodiment the destructured biomass product produced using the present process is contacted with a saccharification enzyme consortium under suitable saccharification conditions to produce fermentable sugars. Prior to saccharification, the pretreated biomass may be brought to the desired moisture content and treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed into the pretreatment product headspace in the flash tank or bubbled through the pretreated biomass if adequate liquid is present while monitoring the pH, until the desired pH is achieved. The temperature is brought to a temperature that is compatible with saccharification enzyme activity, as noted below. Typically suitable conditions may include temperature between about 40° C. and 50° C. and pH between about 4.8 and 5.8. Typically enzymatic saccharification is achieved in about 72 hours or less. The saccharification conditions typically include solids at about 10% or greater.

Enzymatic saccharification of cellulosic or lignocellulosic biomass typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass components they hydrolyze. Glycosidases useful for the present method may include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), acetylxylan esterases (EC 3.1.1.72), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme. Many glycosyl hydrolase enzymes and compositions thereof that are useful for saccharification are disclosed in WO 2011/038019.

In one embodiment (particularly in relation to the production of animal feed or animal feed additive compositions) the saccharification enzyme may comprise at least the following activities: endoglucanase activity and β-glucosidase. Commercial enzymes with such activities can be purchases such as Celluclast® (from DSM/Novozymes). Suitably the saccharification enzyme may additionally comprise an endoxylanase activity. Commercial enzymes with such activities can be purchases such as Accellerase® Duet™ (from Danisco (now DuPont)), Accellerase® Trio™ (from Danisco (now DuPont))

Endoglucanase activity as referred to herein may be endo-1,4-β-D-glucanase activity. An endoglucanase is one which catalyses the endohydrolysis of (1→4)-β-D-glucosidic linkages in cellulose, lichenin and cereal β-D glucans. In other words endoglucanase activity as defined herein means and enzyme which endohydrolyses (1→4)-β-D-glucosidic linkages in cellulose, lichenin and cereal β-D glucans. Endoglucanase activity can be classified under E.G. classification E.G. 3.2.1.4. Another name for endoglucanase is β-glucanase.

The endoxylanase activity—may be endo-1,4-β-xylanase activity. Preferably the endoxylanase endohydrolyses the (1→4)-β-D-xylosidic linkage in xylans. Preferably the endoxylanase is classified as E.G. 3.2.1.8.

β-glucosidase activity as defined herein is the hydrolysis of terminal, non-reducing β-D-glucosyl residues with the release of β-D-glucose. β-glucosidase activity can be classified under E.G. classification E.G. 3.2.1.21.

In one embodiment the saccharification enzyme may comprise no, or substantially no, β-xylosidase activity and/or α-L-arabinofuranosidase activity.

The term "absent" or "no" as used herein means that the enzyme composition has no β-xylosidase activity and no α-arabinofuranosidase activity.

The terms "substantially absent" and "substantially no" as used herein in reference to β-xylosidase activity and/or α-L-arabinofuranosidase activity mean an activity of less than 0.05 unit/mg β-xylosidase activity (suitably less than 0.04 units/mg, suitably less than 0.03 units/mg, suitably less than 0.02 units/mg) as determined using the "Beta-Xylosidase Activity Assay" taught herein and/or less than 0.05 units/mg α-L-arabinofuranosidase activity (suitably less than 0.04 units/mg, suitably less than 0.03 units/mg, suitably less than 0.02 units/mg) as determined using the "Alpha-L-arabinofuranosidase Activity Assay" taught herein.

"Beta-Xylosidase Activity Assay"

The substrate for beta-xylosidase is p-nitropheny-β-D-xylopyranoside (pNβxp) (Sigma).

Reagents:

1. 0.05M Sodium acetate buffer pH 4.8: Add 4.1 g sodium acetate (anhydrous) to 1 L volumetric flask and fill to 1 L with MilliQ water. pH to 4.8 and filter. 2. Substrate solution—1.0 mM pNβxp: Add 0.03 g 4-Nitrophenyl B-D-xylanopyranoside to a 100 mL volumetric flask and fill to 100 mL using 0.05M sodium acetate buffer. Mix until dissolved. 3.1M Sodium carbonate: Add 21.2 g sodium carbonate (anhydrous) to 200 mL of MilliQ water and mix until dissolved.

Standard Curve Generation:

Preparation of stock solution: Add 0.05 g 4-nitrophenol (Sigma 1048) to 15 mL conical tube and vortex with 5 mL 190 proof ethanol until dissolved. Pour solution into a 100 mL volumetric flask making sure to transfer entire solution by rinsing the conical tube with MilliQ water and transferring contents to flask. Fill flask to 100 mL with MilliQ water and mix thoroughly. Prepare 4 sets of the following dilutions from stock solution in 15 mL conical tubes (20 tubes total):

| Dilution | MilliQ Water (mL) | Stock Solution (mL) | 4-nitrophenol concentration (mM) |
| --- | --- | --- | --- |
| 1:10 | 9.0 | 1.0 | 0.359 |
| 1:8 | 7.0 | 1.0 | 0.449 |
| 1:6 | 5.0 | 1.0 | 0.599 |
| 1:4 | 3.0 | 1.0 | 0.898 |
| 1:2 | 1.0 | 1.0 | 1.797 |

To each of the tubes add: 1 mL pNβxp substrate solution, 1 mL sodium carbonate solution, 10 mL MilliQ water, 100 uL standard dilution. Prepare reagent blank by adding 200 uL sodium acetate buffer instead of standard dilution. Vortex tubes. Blank spectrophotometer with MilliQ water at 400 nm. Measure and record absorbance of each sample at 400 nm. Subtract the absorbance of the reagent blank from the absorbance of the samples.

Preparation of Enzyme Dilutions:

Enzyme samples should be diluted with sodium acetate buffer so that the final absorbance (sample absorbance—reagent blank absorbance) is between 0.2 and 0.4. This will ensure that the activity is measured in the linear range of the assay. Prepare serial dilutions from 1:10 to 1:100,000 to help determine what dilution will be in the linear range of the assay.

Assay:

Incubate 1 mL of pNβxp substrate in each sample and reagent blank tube in a 50 C water bath until substrate is equilibrated to 50 C (5-10 min). Set timer for 10 min, start timer and at 10 sec intervals, add 200 uL of sample to their respective conical tubes and 200 uL sodium acetate buffer to the reagent blank tube. At the end of 10 min, add 1 mL sodium carbonate to each tube at 10 second intervals to quench the reaction. Remove from water bath, add 10 mL MilliQ water to each tube and vortex. Read each sample at 400 nm on the spectrophotometer and subtract the reagent blank to obtain final absorbance of the sample. The beta-xylosidase activity in pNβxp U/mL is calculated using the following formula: [(Δabs-y int.)×dilution factor]/slope×10. α-L-arabinofuranosidases (E.G. 3.2.1.55) may hydrolyze arabinan to L-arabinose.

"Alpha-L-Arabinofuranosidase Activity Assay"

The substrate for α-L-arabinofuranosidase is p-nitrophenyl-α-L-arabinofuranoside (pNαLaf) (Sigma).

Reagents:

1. 0.05M Sodium acetate buffer pH 4.8: Add 4.1 g sodium acetate (anhydrous) to 1 L volumetric flask and fill to 1 L with MilliQ water. pH to 4.8 and filter. 2. Substrate solution—1.0 mM pNαLaf: Add 0.03 g 4-Nitrophenyl α-L-arabinofuranoside to a 100 mL volumetric flask and fill to 100 mL using 0.05M sodium acetate buffer. Mix until dissolved. 3.1M Sodium carbonate: Add 21.2 g sodium carbonate (anhydrous) to 200 mL of MilliQ water and mix until dissolved.

Standard Curve Generation:

Preparation of stock solution: Add 0.05 g 4-nitrophenol (Sigma 1048) to 15 mL conical tube and vortex with 5 mL 190 proof ethanol until dissolved. Pour solution into a 100 mL volumetric flask making sure to transfer entire solution by rinsing the conical tube with MilliQ water and transferring contents to flask. Fill flask to 100 mL with MilliQ water and mix thoroughly. Prepare 4 sets of the following dilutions from stock solution in 15 mL conical tubes (20 tubes total):

| Dilution | MilliQ Water (mL) | Stock Solution (mL) | 4-nitrophenol concentration (mM) |
| --- | --- | --- | --- |
| 1:10 | 9.0 | 1.0 | 0.359 |
| 1:8 | 7.0 | 1.0 | 0.449 |
| 1:6 | 5.0 | 1.0 | 0.599 |
| 1:4 | 3.0 | 1.0 | 0.898 |
| 1:2 | 1.0 | 1.0 | 1.797 |

To each of the tubes add: 1 mL pNαLaf substrate solution, 1 mL sodium carbonate solution, 10 mL MilliQ water, 100 uL standard dilution. Prepare reagent blank by adding 200 uL sodium acetate buffer instead of standard dilution. Vortex tubes. Blank spectrophotometer with MilliQ water at 400 nm. Measure and record absorbance of each sample at 400 nm. Subtract the absorbance of the reagent blank from the absorbance of the samples.

Preparation of Enzyme Dilutions:

Enzyme samples should be diluted with sodium acetate buffer so that the final absorbance (sample absorbance–reagent blank absorbance) is between 0.2 and 0.4. This will ensure that the activity is measured in the linear range of the assay. Prepare serial dilutions from 1:10 to 1:100,000 to help determine what dilution will be in the linear range of the assay.

Assay:

Incubate 1 mL of pNαLaf substrate in each sample and reagent blank tube in a 50 C water bath until substrate is equilibrated to 50 C (5-10 min). Set timer for 10 min, start timer and at 10 sec intervals, add 200 uL of sample to their respective conical tubes and 200 uL sodium acetate buffer to the reagent blank tube. At the end of 10 min, add 1 mL sodium carbonate to each tube at 10 second intervals to quench the reaction. Remove from water bath, add 10 mL MilliQ water to each tube and vortex. Read each sample at 400 nm on the spectrophotometer and subtract the reagent blank to obtain final absorbance of the sample. The α-L-arabinofuranosidase activity in pNαLaf U/mL is calculated using the following formula: [(Δabs-y int.)×dilution factor]/slope×10.

In one embodiment the enzyme composition for use in the present invention has less than 0.05 unit/mg β-xylosidase activity (suitably less than 0.04 units/mg, suitably less than 0.03 units/mg, suitably less than 0.02 units/mg) as determined using the "Beta-Xylosidase Activity Assay" taught herein and less than 0.05 units/mg α-L-arabinofuranosidase activity (suitably less than 0.04 units/mg, suitably less than 0.03 units/mg, suitably less than 0.02 units/mg) as determined using the "Alpha-L-arabinofuranosidase Activity Assay" taught herein.

In one embodiment, the enzyme composition may comprise no, or substantially no, β-xylosidase activity and no, or substantially no, α-L-arabinofuranosidase activity.

In one embodiment, the enzyme composition may comprise no β-xylosidase activity and no α-L-arabinofuranosidase activity.

Saccharification enzymes may be obtained commercially. Such enzymes include, for example, Spezyme® CP cellulase, Multifect® xylanase, Accelerase® 1500, Accellerase® DUET, and Accellerase® Trio™ (Dupont™/Genencor®, Wilmington, Del.), and Novozyme-188 (Novozymes, 2880 Bagsvaerd, Denmark). In addition, saccharification enzymes may be unpurified and provided as a cell extract or a whole cell preparation. The enzymes may be produced using recombinant microorganisms that have been engineered to express one or more saccharifying enzymes.

Additional enzymes for saccharification include, for example, glycosyl hydrolases such as members of families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and the classification is available in the Carbohydrate-Active enzyme (CAZy) database (Cantarel et al. (2009) Nucleic Acids Res. 37 (Database issue):D233-238). Certain of these enzymes are able to act on various substrates and have demonstrated efficacy as saccharification enzymes. Glycoside hydrolase family 3 ("GH3") enzymes have a number of known activities, including, for example, β-glucosidase (EC:3.2.1.21); β-xylosidase (EC:3.2.1.37); N-acetyl β-glucosaminidase (EC:3.2.1.52); glucan β-1,3-glucosidase (EC:3.2.1.58); cellodextrinase (EC:3.2.1.74); exo-1,3-1,4-glucanase (EC: 3.2.1); and/or β-galactosidase (EC 3.2.1.23) activities. Glycoside hydrolase family 39 ("GH39") enzymes also have a number of known activities, including, for example, α-L-iduronidase (EC:3.2.1.76) and/or β-xylosidase (EC: 3.2.1.37) activities. Glycoside hydrolase family 43 ("GH43") enzymes have a number of known activities including, for example, L-α-arabinofuranosidase (EC 3.2.1.55); β-xylosidase (EC 3.2.1.37); endoarabinanase (EC 3.2.1.99); and/or galactan 1,3-β-galactosidase (EC 3.2.1.145) activities. Glycoside hydrolase family 51 ("GH51") enzymes are known to have, for example, L-α-arabinofuranosidase (EC 3.2.1.55) and/or endoglucanase (EC 3.2.1.4) activities. Glycoside hydrolase family 10 ("GH10") have been described in detail in Schmidt et al., 1999, Biochemistry 38:2403-2412 and Lo Leggio et al., 2001, FEBS Lett 509: 303-308) and the Glycoside hydrolase family 11 ("GH11") have been described in Hakouvainen et al. (1996, Biochemistry 35:9617-24).

Destructured biomass of the present process may be saccharified using saccharification chemical treatment under suitable conditions for saccharification as known to one skilled in the art. Chemical saccharification methods that may be used include treatment with a saccharification chemical such as mineral acids including HCl and $H_2SO_4$, as shown in Example 7 herein. The use of liquid acids and well as solid acids, including metal oxides, sulfonated carbonaceous based acids and polymer based acids, for hydrolysis of cellulose is described in Huang and Fu ((2013) Green Chem. 15:1095-1111). Organic solvents may be used as chemical treatment for saccharification of the present destructured biomass. Any polar organic solvent may be used including, but not limited to, cyclic ethers, cyclic lactones, alcohols, alkane diols, ketones, ethers, esters, amides, cyclic amides, polyethylene glycols, sulfoxides, sulfones, glycols, and formamides. For example, treatment of the present destructured biomass with the sulfone sulfolane is shown in Examples 16-18 herein. Any of these methods may be used to saccharify the present destructured cellulosic biomass.

Sugars including glucose and xylose are released by saccharification of the present destructured biomass, and these may provide a carbohydrate source for a biocatalyst for a fermentation process. Sugars released from the destructured biomass produced in the present process have a yield that is at least about 15% greater (on a total possible sugars yield basis) as compared to the yield from the same input cellulosic biomass that is not treated with at least one set of compression and impact forces of at least about 5,000 N using centrifugal motion, with a specific energy input that is less than 40% of the total combustible energy of the biomass. The yield on a total possible sugars yield basis may be at least about 50%, 55%, 60%, 65%, 70%, 75%, 80% or greater.

Sugars released from the destructured biomass, produced in the present process, by enzymatic saccharification were shown herein to include glucose and glucose oligomers at greater than 80% yield. The yield of glucose and glucose oligomers may be greater than 80%, 85%, 90%, 95% or more. Sugars released from the destructured biomass produced in the present process by enzymatic saccharification were shown herein to include xylose and xylose oligomers at greater than 70%. The yield of xylose and xylose oligomers may be greater than 70%, 75%, 80%, 85% or more.

Sugars released from the destructured biomass, produced in the present process, by chemical saccharification were shown herein in Example 14 to include xylose and xylose oligomers at greater than 74% yield. Sugars released by chemical saccharification in Examples 16-18 herein include glucose and glucose oligomers at 100% yield, and xylose and xylose oligomers at 100% yield. Thus the yield of xylose and xylose oligomers from chemical saccharification may be greater than 70%, 75%, 80%, 85%, 90%, 95% or more depending on the chemical treatment used.

Thus in one embodiment, the yield from saccharification of the destructured biomass produced by the present process for glucose and glucose oligomers is at least about 80%. In another embodiment, the yield from saccharification of the destructured biomass produced by the present process for xylose and xylose oligomers is at least about 74%. In yet another embodiment the yield from saccharification of the destructured biomass produced by the present process for glucose and glucose oligomers is at least about 80% and for xylose and xylose oligomers is at least about 74%.

The sugars produced by saccharification of the present destructured biomass may be used as a carbohydrate source for biocatalyst fermentation. The sugars may be isolated prior to use. More typically the sugars are present in a biomass hydrolysate that is used as fermentation medium. The fermentation medium may be composed solely of hydrolysate, or may include components additional to the hydrolysate such as sorbitol or mannitol as described in U.S. Pat. No. 7,629,156.

In addition, one or more of the sugars released from the destructured biomass produced in the present process may be used in chemical reactions to produce products. The chemical reactions performed using these sugars may optionally include a chemical catalyst.

In addition the product produced by saccharification of the present destructured biomass may be used as a feed additive composition or as a feedstuff or part of a feedstuff for animals.

Biocatalyst

Any biocatalyst that produces a target compound utilizing glucose and preferably also xylose, either naturally or through genetic engineering, may be used for fermentation of the fermentable sugars produced using the present process. Target compounds that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, mannitol, and sorbitol. Acids may include acetic acid, formic acid, lactic acid, propionic acid, 3-hydroxypropionic acid, butyric acid, gluconic acid, itaconic acid, citric acid, succinic acid, 3-hydroxyproprionic acid, fumaric acid, maleic acid, and levulinic acid. Amino acids may include glutamic acid, aspartic acid, methionine, lysine, glycine, arginine, threonine, phenylalanine and tyrosine. Additional target compounds include methane, ethylene, acetone and industrial enzymes.

The fermentation of sugars to target compounds may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and may include, for example, organisms belonging to the genera of *Escherichia, Zymomonas, Saccharomyces, Candida, Pichia, Streptomyces, Bacillus, Lactobacillus*, and *Clostridiuma*. Typical examples of biocatalysts include recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*.

Typically the biocatalyst is able to utilize glucose and xylose, and may additionally utilize arabinose. For example, any strain of *Zymomonas* that is an effective biocatalyst for the desired target compound production may be used. *Zymomonas* cells naturally produce ethanol using glucose, fructose and/or sucrose as fermentation substrates, but xylose is not metabolized. It is desirable to use *Zymomonas* cells that have been engineered for xylose utilization, which has been accomplished as follows. Typically four genes have been introduced into *Z. mobilis* for expression of four enzymes involved in xylose metabolism to create a xylose utilization metabolic pathway as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol. DNA sequences encoding these enzymes may be obtained from any of numerous microorganisms that are able to metabolize xylose, such as enteric bacteria, and some yeasts and fungi. Sources for the coding regions may include *Xanthomonas, Klebsiella, Escherichia, Rhodobacter, Flavobacterium, Acetobacter, Gluconobacter, Rhizobium, Agrobacterium, Salmonella, Pseudomonads,* and *Zymomonas*. The coding regions of *E. coli* are typically used.

The encoding DNA sequences are operably linked to promoters that are expressed in *Zymomonas* cells such as the promoter of *Z. mobilis* glyceraldehyde-3-phosphate dehydrogenase (GAP promoter), and *Z. mobilis* enolase (ENO promoter). A mutant GAP promoter with increased expression as disclosed in U.S. Pat. No. 7,989,206, is also useful for expression in *Zymomonas*. The coding regions may individually be expressed from promoters, or two or more coding regions may be joined in an operon with expression from the same promoter. The resulting chimeric genes may be introduced into *Zymomonas* cells and maintained on a plasmid, or integrated into the genome using, for example, homologous recombination, site-directed integration, or random integration. Examples of strains engineered to express a xylose utilization metabolic pathway include CP4(pZB5) (U.S. Pat. No. 5,514,583), ATCC31821/pZB5 (U.S. Pat. No. 6,566,107), 8b (U.S. Pat. No. 7,223,575; Mohagheghi et al., (2004) Biotechnol. Lett. 25; 321-325), and ZW658 (ATTCC # PTA-7858). Cells of *Zymomonas* that are engineered for expression of the xylose utilization metabolic pathway generally require a period of adaptation in xylose-containing medium prior to being able to grow in medium that contains xylose as the only sugar.

*Zymomonas* cells may be additionally engineered for arabinose utilization as described in U.S. Pat. No. 5,843,760. To allow arabinose utilization, genes expressed in addition to genes of the xylose utilization pathway include: 1) L-arabinose isomerase to convert L-arabinose to L-ribulose, 2) L-ribulokinase to convert L-ribulose to L-ribulose-5-phosphate, and 3) L-ribulose-5-phosphate-4-epimerase to convert L-ribulose-5-phosphate to D-xylulose (U.S. Pat. No. 5,843,760). As disclosed in US 2011/0143408, improved arabinose utilization may be achieved by additionally expressing an arabinose-proton symporter, such as by expressing a coding region from an araE gene.

In addition the *Zymomonas* cells may have one or more additional genetic modifications that improve the strain such as one that increases growth rate and/or cell mass, increases utilization of xylose and/or allows use of other sugars such as arabinose, increases tolerance to inhibitory compounds such as acetate, or increases production of ethanol. For example the endogenous himA gene, which encodes the alpha subunit of the integration host factor, may be genetically modified to reduce its expression which improves growth in medium containing acetate as described in U.S. Pat. No. 7,897,396. Acetate is present in biomass hydrolysate, thus when using medium containing biomass hydrolysate, increased tolerance to this component is desired.

In another example a genetic modification may be made that reduces glucose-fructose oxidoreductase (GFOR) activity as described in U.S. Pat. No. 7,741,119. Reduced expression of GFOR, as well as of the himA gene, may be by any method such as those described above for reducing aldose reductase activity.

In another example a genetic modification may be made which increases ribose-5-phosphate isomerase (RPI) activity, as disclosed in commonly owned and co-pending US 2012/0156746. Increased RPI expression may be accomplished by increasing expression of the endogenous RPI encoding gene, such as with a promoter that is more highly active than the native promoter, or by expressing a heterologous gene encoding any protein or polypeptide with ribose-5-phosphate isomerase activity in *Zymomonas*.

In another example the xylose utilization isomerase that is expressed as part of the xylose utilization metabolic pathway is expressed using a mutant, highly active promoter that is disclosed in U.S. Pat. No. 7,989,206 and U.S. Pat. No. 7,998,722. The mutant promoters disclosed therein are promoters of the *Zymomonas mobilis* glyceraldehyde-3-phosphate dehydrogenase gene. Also the xylose isomerase may be a Group I xylose isomerase included in the class of enzymes identified by EC 5.3.1.5 as disclosed in commonly owned and co-pending US 2011/0318801. It is disclosed therein that Group I xylose isomerases, such as one expressed from a coding region isolated from *Actinoplanes missouriensis*, have higher activity in *Zymomonas* than Group 2 xylose isomerase. Group I xylose isomerases are defined therein by molecular phylogenetic bioinformatics analysis (using PHYLIP neighbor joining algorithm as implemented in PHYLIP (Phylogeny Inference Package version 3.5c; Felsenstein (1989) Cladistics 5:164-166), GroupSim analysis (Capra and Singh (2008) Bioinformatics 24: 1473-1480), and a Profile Hidden Markov Model (using the hmmsearch algorithm of the HMMER software package; Janelia Farm Research Campus, Ashburn, Va.).

In another example the *Zymomonas* cells may be adapted for growth in a stress culture containing ethanol and ammonium acetate as disclosed in U.S. Pat. No. 8,247,208. These *Zymomonas* strains with improved acetate tolerance are particularly useful when using cellulosic biomass hydrolysate containing fermentation medium, which contains acetate.

Strains disclosed in the above references and strains described herein provide examples of strains that may be used as biocatalysts and include ATCC31821/pZB5, ZW658 (ATCC #PTA-7858), ZW800, ZW801-4, ZW801-4::ΔhimA, AcR#3, ZW705, AR3 7-321, and ZW1-XA111.

Additional biocatalysts that produce ethanol such as yeasts and genetically modified strains of *E. coli* (Underwood et al., (2002) Appl. Environ. Microbiol. 68:6263-6272), as well as biocatalysts that produce other target compounds such as those listed above may be used in fermentation of fermentable sugars produced using the present process. For example, yeast cells that are engineered to express a pathway for synthesis of butanol and *E. coli* engineered for production of 1,3-propanediol have been described. Engineering of pathways for butanol synthesis (including isobutanol, 1-butanol, and 2-butanol) in biocatalysts has been disclosed, for example in U.S. Pat. No. 8,206,970, US 20070292927, US 20090155870, U.S. Pat. No. 7,851,188, and US 20080182308. Engineering of pathways in biocatalysts for 1,3-propanediol has been disclosed in U.S. Pat. No. 6,514,733, U.S. Pat. No. 5,686,276, U.S. Pat. No. 7,005,291, U.S. Pat. No. 6,013,494, and U.S. Pat. No. 7,629,151.

For utilization of xylose as a carbon source, a yeast cell may be engineered for expression of a complete xylose utilization pathway. Engineering of yeast such as *S. cerevisiae* for production of ethanol from xylose is described in Matsushika et al. (Appl. Microbiol. Biotechnol. (2009) 84:37-53) and in Kuyper et al. (FEMS Yeast Res. (2005) 5:399-409).

Lactic acid has been produced in fermentations by recombinant strains of *E. coli* (Zhou et al., (2003) Appl. Environ. Microbiol. 69:399-407), natural strains of *Bacillus* (U.S. Pat. No. 7,098,009), and *Rhizopus oryzae* (Tay and Yang (2002) Biotechnol. Bioeng. 80:1-12). Recombinant strains of *E. coli* have been used as biocatalysts in fermentation to produce 1,3 propanediol (U.S. Pat. No. 6,013,494, U.S. Pat. No. 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (U.S. Pat. No. 7,642,083).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17crl (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-Ul-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2, 3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium*, *Brevibacterium*, and *Serratia*. For example, production of histidine using a strain resistant to a histidine analog is described in Japanese Patent Publication No. 56008596 and using a recombinant strain is described in EP 136359. Production of tryptophan using a strain resistant to a tryptophan analog is described in Japanese Patent Publication Nos. 47004505 and 51019037. Production of isoleucine using a strain resistant to an isoleucine analog is described in Japanese Patent Publication Nos. 47038995, 51006237, 54032070. Production of phenylalanine using a strain resistant to a phenylalanine analog is described in Japanese Patent Publication No. 56010035. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 54037235 and 57150381) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. No. 6,861,237, U.S. Pat. No. 6,777,207, U.S. Pat. No. 6,228,630).

Target compounds produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

Fermentation

Any biocatalyst, such as those described above, is used for fermentation of fermentable sugars produced by the present process. Fermentation conditions used with a particular biocatalyst may be as described in the above cited references, or as known to one skilled in the art.

As an example, the following describes a large-scale fermentation using *Zymomonas mobilis* for production of ethanol. The desired *Z. mobilis* cells are grown in shake flasks in semi-complex medium at about 30° C. to about 37° C. with shaking at about 150 rpm in orbital shakers and then transferred to a 10 L seed fermenter containing similar medium. The seed culture is grown in the seed fermenter anaerobically until $OD_{600}$ is between 3 and 6, when it is transferred to the production fermenter where the fermentation parameters are optimized for ethanol production. Typical inoculum volumes transferred from the seed tank to the production tank range from about 2% to about 20% v/v. The fermentation medium may be composed solely of hydrolysate, or may include components additional to the hydrolysate such as sorbitol or mannitol at a final concentration of about 5 mM as described in U.S. Pat. No. 7,629,156. The fermentation may be a batch process, fed-batch process, or continuous process, Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992).

The fermentation is typically controlled at pH 4.5-6.5 using caustic solution (such as ammonium hydroxide, potassium hydroxide, or sodium hydroxide) and either sulfuric or phosphoric acid. The temperature of the fermentor is controlled at 30° C.-37° C. In order to minimize foaming, antifoam agents (any class-silicone based, organic based, etc.) may be added to the vessel as needed.

Any set of conditions described above, and additional variations in these conditions that are well known in the art, are suitable conditions for production of ethanol by xylose-utilizing recombinant *Zymomonas* cells. Typically cultures are incubated without supplemented air, oxygen, or other gases (which may include conditions such as anaerobic, microaerobic, or microaerophilic fermentation), for at least about 20 hours, and may be run for about 48 hours, 120 hours or longer.

In addition, fermentation may be performed using a simultaneous saccharification and fermentation (SSF) process or hybrid saccharification and fermentation (HSF) process. In HSF partial saccharification is carried out prior to addition of *Zymomonas* cells, then further saccharification and fermentation occur simultaneously. The second stage simultaneous saccharification and fermentation may be performed as described in US Patent Application Publication 2011/0318803. In this process *Zymomonas* cells are grown under conditions of low impeller agitation with high concentration of insoluble solids in a saccharification-fermentation mixture during a simultaneous saccharification and fermentation reaction for the production of high concentrations of ethanol.

Feed Applications

In some embodiments the destructured biomass obtained in accordance with the present invention and/or the biomass hydrolysate (which refers to a product resulting from saccharification (suitably enzyme saccharification) of the destructured biomass) is used in feed (e.g. animal feed) applications, e.g. as a feed additive composition, a premix, or a feedstuff or a part of any one of a feed additive composition, a premix, or a feedstuff.

The destructured biomass and/or the biomass hydrolysate may be used in combination with at least one in-feed glycosyl hydrolase enzyme.

When the destructured biomass or the biomass hydrolysate is used in combination with the at least one in-feed glycosyl hydrolase enzyme, the combination may be fed to an animal immediately after admixing the destructured biomass or the biomass hydrolysate with the at least one in-feed glycosyl hydrolase enzyme.

In other embodiments the in-feed glycosyl hydrolase enzyme is maintained in an inactive form on the destructured biomass or the biomass hydrolysate, until such time that the enzyme enters the gastrointestinal tract (GIT) of an animal. In such instances, when the enzyme enters the GIT of the animal the enzyme is activated (e.g. becomes active).

The term "in-feed" as used herein means that the enzyme is functional, preferably primarily functional, more preferably solely functional, in the GIT of the animal. In other words, the term "in-feed" as used herein means that the enzyme is substantially inactive (or is inactive) in the feed additive composition and/or on the destructured biomass or the biomass hydrolysate prior to feeding the feed additive composition or feedstuff comprising same to an animal.

The term "primarily functional" means that the enzyme mainly functions on its substrate once it enters the GIT. In other words, prior to entering the GIT the level of enzyme activity defined as the amount of solubilisation of biomass material to oligosaccharides and monosaccharides is less than 20%, suitably less than 10%, preferably less than 5%, of the level of enzyme activity after it enters the GIT (particularly, after it enters the small intestine of the GIT).

The term "solely functional" as used herein means that the enzyme is inactive before entering the GIT and is activated upon entering the GIT.

The term "inactive" as used herein means that the enzyme is not active. This may mean that the enzyme's activity is somehow inhibited or that the enzyme is in an environment in which it is inactive or that the enzyme is presented to its substrate immediately prior to feeding to the animal such that there is not enough time to be active. The "inactivity" of the enzyme is in any event reversible once it enters the GIT of an animal.

The term "substantially inactive" as used herein means that the enzyme has low activity compared with its activity once it has entered the GIT (e.g. in the small intestine of the animal). For instance, substantially inactive may mean that the enzyme in the feed additive composition and/or on the lignocellulosic biomass has less than 10% of its activity when compared with its activity in the GIT (particularly, in the small intestine of the GIT).

Maintaining the "in-feed" enzyme in an inactive or substantially inactive state in the feed additive composition and/or on the destructured biomass or the biomass hydrolysate can be achieved in a number of ways known to one skilled in the art.

By way of example only maintaining the water content (wt %) of the destructured biomass or the biomass hydrolysate and/or of the in-feed enzyme and/or of the feed additive composition at less than 15%, preferably less than 10%, is sufficient to ensure that the in-feed enzyme is inactive or substantially inactive in the feed additive composition and/or on the destructured biomass or on the biomass hydrolysate.

Therefore in one embodiment the in-feed enzyme may be admixed with the destructured biomass or the biomass hydrolysate when the destructured biomass or the biomass hydrolysate, the in-feed enzyme or both are in a dry state or a substantially dry state.

In one embodiment the destructured biomass or the biomass hydrolysate and/or the in-feed enzyme and/or the feed additive composition, post-admixing the destructured biomass or the biomass hydrolysate and the in-feed enzyme, are (maintained and/or stored) in a dry state or substantially dry state.

The term "dry state" as used herein means that the destructured biomass or the biomass hydrolysate and/or the in-feed enzyme and/or the feed additive composition contains no or only a very low amount of water. In other words the term "dry state" as used herein may mean that the destructured biomass or the biomass hydrolysate and/or the in-feed enzyme and/or the feed additive composition comprises less than 5%, preferably less than 1%, water content (wt %).

The term "substantially dry state" as used herein means that the destructured biomass or the biomass hydrolysate and/or the in-feed enzyme and/or the feed additive composition contains only a very low amount of water. In other words the term "substantially dry state" as used herein may mean that the destructured biomass or the biomass hydrolysate and/or the in-feed enzyme and/or the feed additive composition comprises less than 15%, preferably less than 10%, water content (wt %).

In one embodiment, the method according to the present invention may comprise drying the destructured biomass or the biomass hydrolysate prior to, during or after (preferably prior to) admixing the biomass with at least one in-feed glycosyl hydrolase enzyme.

In another embodiment the destructured biomass or the biomass hydrolysate either before or after adding the at least one in-feed glycosyl hydrolase enzyme comprises less than 15 wt % moisture content.

In another embodiment the destructured biomass or the biomass hydrolysate either before or after adding the at least one in-feed glycosyl hydrolase enzyme comprises less than 10 wt % moisture content.

In another embodiment the destructured biomass or the biomass hydrolysate either before or after adding the at least one in-feed glycosyl hydrolase enzyme comprises less than 5 wt % moisture content.

In another embodiment the destructured biomass or the biomass hydrolysate either before or after adding the at least one in-feed glycosyl hydrolase enzyme comprises less than 1 wt % moisture content.

The "in-feed" enzyme may be maintained in an inactive or substantially inactive state in the feed additive composition and/or on the destructured biomass or the biomass hydrolysate by physically preventing the enzyme from interacting with its substrate. For example the in-feed enzyme may be encapsulated prior to admixing with the destructured biomass or the biomass hydrolysate.

When the in-feed enzyme is physically prevented from interacting with its substrate in the destructured biomass or the biomass hydrolysate, then once in the GIT the physical barrier is removed thus allowing the interaction of the in-feed enzyme with its substrate.

By way of example only, the encapsulation may be removed by passage of the encapsulated enzyme through the stomach of an animal. The stomach of an animal is at very low (acidic) pH (e.g. pH 2-4). This acidity can be used to activate encapsulated enzymes.

In one embodiment the enzyme may be encapsulated by a polymer, such as chitin or chitosans, gelatin, gum arabic or wax for example. By way of example only the polymer may be a gelatin or gum arabic as taught in Xue et al Food Funct. 2013 Apr. 25; 6 Feb. (epub); 4 (4) 610-7 (which is incorporated herein by reference). Alternatively, the polymer may a chitosan-based hydrogel as taught in Zhang et al Biomacromolecules 2011, 12, 2894-2901 (which is incorporated herein by reference).

In one embodiment the at least one in-feed glycosyl hydrolase enzyme may be activated by feeding the at least one in-feed glycosyl hydrolase enzyme to an animal.

The term "inactive" as used herein may mean that the enzyme is presented to its substrate immediately prior to feeding to the animal such that there is not enough time to be active before it enters the GIT of the animal.

In one embodiment the at least one in-feed glycosyl hydrolase enzyme may be admixed with the destructured biomass or the biomass hydrolysate immediately prior to feeding the feed additive composition or feedstuff comprising the destructured biomass or the biomass hydrolysate to an animal.

In one preferred embodiment the in-feed enzyme is maintained in an inactive or substantially inactive state by maintaining the feed additive composition in a dry state or substantially dry state. This has additional benefits in that the handling, e.g. processing, packaging, storage and transport of a dry composition is easier than non-dry formulations (e.g. liquids).

However, it can also be envisaged that a kit where the destructured biomass or the biomass hydrolysate is physically separated from the in-feed enzyme (e.g. by being in separate containers) would enable the end user (e.g. farmer) to admix the destructured biomass or the biomass hydrolysate with the in-feed enzyme immediately prior to feeding the mixture to the animal. In such a situation the destructured biomass or the biomass hydrolysate and/or the in-feed enzyme may be in any formulation, e.g. solid, semi-solid or liquid for example.

The destructured biomass or the biomass hydrolysate can have even more nutritional value for use as a feed if one combines this biomass with in-feed enzymes. It was surprising that the relatively short period of time that the biomass is in the GIT of an animal provides sufficient time for the in-feed enzyme(s) to improve the nutritional value of this sort of biomass.

In-Feed Enzymes

In the present application the in feed enzyme(s) is/are suitably in feed glycosyl hydrolase enzyme(s).

Glycosyl hydrolase enzymes are a widespread group of enzymes which hydrolyse the glycosidic bond between two or more carbohydrates or between a carbohydrate and a non-carbohydrate moiety. Many of these are enzymes produced by microorganisms for the degradation of the polysaccharides in the cell walls of plants.

A glycosyl hydrolase enzyme is classified as having an E.G. classification 3.2.1.4 (in accordance with the Recommendations of the Nomenclature Committee (NC) of the International Union of Biochemistry and Molecular Biology (IUBMB) on the Nomenclature and Classification of Enzymes by the Reactions they Catalyse; as Published in *Enzyme Nomenclature* 1992 [Academic Press, San Diego; 0-12-227165-3] with Supplement 1 (1993), Supplement 2 (1994), Supplement 3 (1995), Supplement 4 (1997) and Supplement 5 (in *Eur. J. Biochem.* 1994, 223, 1-5; *Eur. J. Biochem.* 1995, 232, 1-6; *Eur. J. Biochem.* 1996, 237, 1-5; *Eur. J. Biochem.* 1997, 250; 1-6, and *Eur. J. Biochem.* 1999, 264, 610-650; respectively).

Suitably the at least one in-feed glycosyl hydrolase enzyme(s) may be a glycan degrading enzyme.

In one embodiment the at least one in-feed glycosyl hydrolase enzyme(s) hydrolyses a beta-1,4-glycosidic link.

In one embodiment, the at least one in-feed glycosyl hydrolase enzyme(s) may comprise (or consist essentially of, or consist of) one or both of the following enzyme activities: cellulase activity and/or hemi-cellulase activity.

In one embodiment, the at least one in-feed glycosyl hydrolase enzyme(s) may comprise (or consist essentially of, or consist of) at least cellulase and hemi-cellulase activity.

The cellulase activity may comprise (or consist essentially of, or consist of) at least the following enzyme activities: endoglucanase activity and β-glucosidase activity.

The hemi-cellulase activity may comprise (or consist of, or consist essentially of) at least endoxylanase enzyme activity.

Suitably, the at least one in-feed glycosyl hydrolase enzyme(s) comprising at least one or both of cellulase activity and/or hemi-cellulase activity may further comprise one or both of the following activities: exoglucosidase activity and/or lytic polysaccharide monooxygenase activity.

In one embodiment the at least one in-feed glycosyl hydrolase enzyme(s) comprises (or consists essentially of, or consists of) one or more of the following enzyme activities: endoglucanase activity, endoxylanase activity or β-glucosidase activity.

Suitably, the at least one in-feed glycosyl hydrolase enzyme(s) comprising at least one of the following enzyme activities: endoglucanase activity, endoxylanase activity or β-glucosidase activity may further comprise one or both of the following activities: exoglucosidase activity and/or lytic polysaccharide monooxygenase activity.

In one embodiment the at least one in-feed glycosyl hydrolase enzyme(s) comprises (or consists essentially of, or consists of) two or more (e.g. suitably three) of the following enzyme activities: endoglucanase activity, endoxylanase activity or β-glucosidase activity.

Suitably the at least one in-feed glycosyl hydrolase enzyme(s) comprising two or more (e.g. suitably three) of the following enzyme activities: endoglucanase activity, endoxylanase activity or β-glucosidase activity may further comprise one or both of the following activities: exoglucosidase activity and/or lytic polysaccharide monooxygenase activity.

In one embodiment the at least one in-feed glycosyl hydrolase enzyme(s) is an enzyme composition comprising more than one enzyme. The enzyme composition comprising more than one enzyme preferably has at least one cellulase enzyme and at least one hemi-cellulase enzyme.

In another embodiment the enzyme composition comprising more than one enzyme preferably has at least one of the following: an endoglucanase, an endoxylanase or a β-glucosidase.

In one embodiment the enzyme composition comprises at least two (suitably at least three) enzymes. The enzyme composition comprising the at least two (suitably at least three) enzymes preferably has at least two (suitably at least three) of the following: an endoglucanase, an endoxylanase or a β-glucosidase.

Suitably the enzyme composition may further comprise one or both of the following activities: exoglucosidase activity and/or lytic polysaccharide monooxygenase activity.

In a preferable embodiment the enzyme composition may comprise (or consist essentially of, or consist of) at least the following activities: endoglucanase activity, endoxylanase activity and β-glucosidase activity.

In one embodiment the at least one in-feed glycosyl hydrolase enzyme(s) (or enzyme composition) may be characterized by its enzyme activity.

In one embodiment the at least one in-feed glycosyl hydrolase enzyme(s) may be a single enzyme or a combination of enzymes (e.g. an enzyme mix).

In one preferred embodiment the at least one in-feed glycosyl hydrolase enzyme is an enzyme mixture.

Preferably the in-feed enzyme in accordance with the present invention is stable and active in the gastrointestinal tract (GIT) of an animal. In one embodiment the in-feed enzyme is resistant to pepsin. In one embodiment the in-feed enzyme is tolerant to bile salts. In one embodiment the in-feed enzyme is resistant to low pH. In one embodiment the in-feed enzyme can withstand pelleting temperatures (70-95° C.). In one embodiment the in-feed enzyme is active in the range of 37-40° C.

Biophysical Characteristics

The present invention also relates to uses and methods for improving the biophysical characteristics of an animal by administering to an animal an effective amount of a feed additive composition or a feedstuff according to the present invention.

As used herein the term "biophysical characteristics" as used herein means one or more of the group selected from the following: performance of an animal, growth performance of an animal, feed conversion ratio (FCR), ability to digest a raw material (e.g. nutrient digestibility, including starch, fat, protein, fibre digestibility), nitrogen retention, carcass yield, growth rate, weight gain, body weight, mass, feed efficiency, body fat percentage, body fat distribution, growth, egg size, egg weight, egg mass, egg laying rate and environmental impact, e.g. manure output and/or nitrogen excretion.

In one embodiment the biophysical characteristic of the animal means the performance of the animal.

Performance

As used herein, "performance of the animal" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention.

Preferably "performance of the animal" is determined by feed efficiency and/or weight gain of the animal and/or by the feed conversion ratio (FCR).

By "improved performance of the animal" it is meant that there is increased feed efficiency, and/or increased weight gain and/or reduced feed conversion ratio and/or improved digestibility of nutrients or energy in a feed and/or by improved nitrogen retention in the animal resulting from the use of feed additive composition of the present invention compared with feeding the animal the lignocellulosic biomass which has not been treated in accordance with the present invention.

Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time.

By "increased feed efficiency" it is meant that the use of a feed additive composition according the present invention in feed results in an increased weight gain per unit of feed intake compared with an animal fed with the lignocellulosic biomass which has not been treated in accordance with the present invention.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the lignocellulosic biomass which has not been treated in accordance with the present invention is used in or as the feed.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the animal and what comes out in the faeces of the animal, or between what is administered to the animal and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, fiber digestibility and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen Retention

Nitrogen retention as used herein means an animal's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

Carcass Yield and Meat Yield

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

Weight Gain

The present invention further provides a method of increasing weight gain in an animal, e.g. poultry or swine, comprising feeding said animal a feedstuff comprising a feed additive composition according to the present invention.

An "increased weight gain" refers to an animal having increased body weight on being fed feed comprising a feed additive composition compared with an animal being fed a feed comprising or consisting of lignocellulosic biomass which has not been treated in accordance with the present invention.

Improving

The term "improving" as used herein means improved compared with feeding animal the lignocellulosic biomass which has not been treated in accordance with the present invention.

Admixing

In one embodiment "admixing" as used herein includes any method for admixing, such as mixing, combining, spraying etc.).

Animal

The term "animal", as used herein, means an animal that is to be or has been administered with a feed additive composition according to the present invention or a feedstuff comprising said feed additive composition according to the present invention.

Preferably, the animal is a mammal (e.g. a non-human mammal), bird, fish or crustacean including for example livestock or a domesticated animal (e.g. a pet).

In one embodiment the "animal" is livestock.

The term "livestock", as used herein refers to any farmed animal. Preferably, livestock is one or more of cows or bulls (including calves), pigs (including piglets, swine), poultry (including broilers, layers, chickens and turkeys), birds, fish (including freshwater fish, such as salmon, cod, trout and carp, e.g. koi carp, and marine fish, such as sea bass), crustaceans (such as shrimps, mussels and scallops), horses (including race horses), sheep (including lambs).

In one embodiment the animal is poultry (including broilers, layers, chickens and turkeys).

In another embodiment the "animal" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

In one embodiment the animal is a monogastric animal. In a preferred embodiment the monogastric animal may be poultry or pig (or a combination thereof).

In another embodiment the animal is a ruminant animal.

Packaging

In one embodiment the enzyme composition and/or feed additive composition and/or premix and/or feed or feedstuff according to the present invention is packaged.

In one preferred embodiment feed additive composition and/or feed ingredient and/or premix and/or feed or feedstuff is packaged in a bag, such as a paper bag.

In an alternative embodiment the enzyme composition and/or feed additive composition and/or feed ingredient and/or premix and/or feed or feedstuff may be sealed in a container. Any suitable container may be used.

Feed

The destructured biomass or the biomass hydrolysate (with or without in feed enzyme(s)) may be used as or in the preparation of a feed additive composition or a feed.

The feed additive composition of the present invention may be used as—or in the preparation of—a feed.

The term "feed" is used synonymously herein with "feedstuff".

The feed may be in the form of a solution or as a solid—depending on the use and/or the mode of application and/or the mode of administration.

When used as—or in the preparation of—a feed—such as functional feed—the destructured biomass or the biomass hydrolysate (with or without in feed enzyme(s)) of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the destructured biomass or the biomass hydrolysate (with or without in feed enzyme(s)) or the feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes hay, straw, silage, compressed and pelleted feeds, oils and mixed rations, and also sprouted grains and legumes.

Fodder may be obtained from one or more of the plants selected from: alfalfa (Lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats and combinations thereof) and/or large grains such as maize or sorghum; b) by products from plants (e.g. cereals), such as wet-cake, distillers dried grain (DDG), and distillers dried grain solubles (DDGS), corn fibre, corn germ meal, corn bran, Hominy feed, corn gluten feed, wheat shorts, wheat middlings or combinations thereof (preferably by products of methods according to the present invention); c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

A feedstuff of the present invention may contain at least 30%, at least 40%, at least 50% or at least 60% by weight corn and soybean meal or corn and full fat soy, or wheat meal or sunflower meal.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from plants (e.g. cereals), such as wet-cake, distillers dried grain (DDG), and distillers dried grain solubles (DDGS), corn fibre, corn germ meal, corn bran, Hominy feed, corn gluten feed, wheat shorts, wheat middlings or combinations thereof. Some protein sources may also be regarded as high fibre: protein obtained from sources such as sunflower, lupin, fava beans and cotton.

In the present invention the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

The term "feed" in the present invention also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term "feed" in the present invention also encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the colour of ornamental fish.

The term "feed" in the present invention also encompasses in some embodiment bird food. Bird food includes food that is used both in birdfeeders and to feed pet birds. Typically bird food comprises of a variety of seeds, but may also encompass suet (beef or mutton fat).

As used herein the term "contacting" refers to the indirect or direct application of the destructured biomass or the biomass hydrolysate (with or without in feed enzyme(s)) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the destructured biomass or the biomass hydrolysate (with or without in feed enzyme(s)) or the feed additive composition of the present invention is preferably admixed with the product (e.g. feedstuff). Alternatively, the destructured biomass or the biomass hydrolysate (with or without in feed enzyme(s)) or the feed additive composition may be included in the emulsion or raw ingredients of a feedstuff.

For some applications, it is important that the in feed enzyme(s) is made available on or to the surface of a product to be affected/treated. This allows the composition to impart one or more of the following favourable characteristics: biophysical characteristics, e.g. wherein the biophysical characteristic is selected from the group consisting of one or more of the following: performance of an animal, growth performance of an animal, feed conversion ratio (FCR), ability to digest a raw material (e.g. nutrient digestibility, including starch, fat, protein, fibre digestibility), nitrogen retention, carcass yield, growth rate, weight gain, body weight, mass, feed efficiency, body fat percentage, body fat distribution, growth, egg size, egg weight, egg mass, egg laying rate and environmental impact, e.g. manure output and/or nitrogen excretion.

The feed additive compositions of the present invention may be applied to intersperse, coat and/or impregnate a product (e.g. feedstuff or raw ingredients of a feedstuff) with a controlled amount of enzyme(s).

Preferably, the enzyme composition and/or feed additive composition of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components that were present/active in the additive before heating to the specified temperature are still present/active after it cools to room temperature. Preferably, at least about 80% of the enzyme components that were present and active in the additive before heating to the specified temperature are still present and active after it cools to room temperature.

In a particularly preferred embodiment the in-feed enzymes may be formulated into an enzyme composition.

The enzyme composition and/or feed additive composition may be homogenized to produce a powder.

In an alternative preferred embodiment, the enzyme composition and/or feed additive composition may be formulated to granules as described in WO2007/044968 (referred to as TPT granules) incorporated herein by reference.

In another preferred embodiment when the enzyme composition and/or feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing a feed additive composition may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the feed additive composition of the present invention is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

As used herein, the term "feedstuff" refers to a feed material to which one or more feed additive compositions or destructured biomass or the biomass hydrolysate (with or without in feed enzyme(s)) have been added.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

Preferably, the feedstuff is a corn soybean meal mix.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

Formulation

In one embodiment the destructured biomass or the biomass hydrolysate (with or without in feed enzyme(s)) and/or feed additive composition and/or premix and/or feedstuff in accordance with the present invention are dried.

The term "drying" means that the water content (wt %) of the destructured biomass product (with or without in feed enzyme(s)) or biomass hydrolysate product (with or without in feed enzyme(s)) and/or feed additive composition and/or premix and/or feedstuff in accordance with the present invention is reduced to at less than 15%, preferably less than 10%.

Therefore the present invention yet further provides a dried or substantially dried destructured biomass product (with or without in feed enzyme(s)) or biomass hydrolysate product (with or without in feed enzyme(s)) or feed additive composition or premix or feedstuff.

The term substantially-dried in accordance with the present invention means that the water content (wt %) of the product/feed additive composition/premix/feedstuff is less than 30%, preferably less than 15%, preferably less than 10%, preferably less than 5%.

In one embodiment the in-feed enzyme composition may be in a dry enzyme formulation (e.g. in the form of granules or on a carrier (such as a wheat carrier)) prior to admixing with the destructured biomass or biomass hydrolysate.

In one embodiment the saccharification enzyme composition may be in a liquid enzyme formulation prior to admixing with the destructured biomass.

In another embodiment the in-feed enzyme composition may be in a liquid formulation prior to admixing with the destructured biomass or biomass hydrolysate.

In another embodiment the saccharification enzyme composition may be in a liquid formulation prior to admixing with the destructured biomass.

In some embodiments the present invention may provide a semi-liquid product or slurry product. A semi-liquid product or slurry product in accordance with the present invention is a product the water content (wt %) of which is at less than 90%, preferably less than 80%, preferably less than 70% or more preferably less than 60%.

When the enzyme is in a liquid formulation prior to admixing with the destructured biomass or biomass hydrolysate, the enzyme may be admixed by spraying the enzyme formulation or dipping the destructured biomass or biomass hydrolysate into the enzyme formulation for example.

The destructured biomass or biomass hydrolysate (before or after enzyme treatment) and/or the dried solid fraction may be milled and/or powdered and/or formed into a meal.

In one embodiment the product and/or feed additive composition and/or premix and/or feedstuff in accordance with the present invention, are packaged and/or stored in a dry state or substantially dry state.

The terms "dried" or "dry state" as used herein means that the product and/or feed additive composition and/or premix and/or feedstuff in accordance with the present invention contain no or only a very low amount of water. In other words the term "dried" or "dry state" as used herein may mean that the product and/or feed additive composition and/or premix and/or feedstuff in accordance with the present invention comprises less than 5%, preferably less than 1%, water content (wt %).

The term "substantially dry state" as used herein means that the product and/or feed additive composition and/or premix and/or feedstuff in accordance with the present invention contains only a very low amount of water. In other words the term "substantially dry state" as used herein may mean that the and/or feed additive composition and/or premix and/or feedstuff in accordance with the present invention comprises less than 30%, preferably less than 15%, preferably less than 10%, water content (wt %).

In one embodiment the product and/or feed additive composition and/or premix and/or feedstuff in accordance with the present invention comprises less than 20 wt % moisture content.

In another embodiment the product on and/or feed additive composition and/or premix and/or feedstuff in accordance with the present invention comprises less than 15 wt % moisture content.

In another embodiment the product and/or feed additive composition and/or premix and/or feedstuff in accordance with the present invention comprises less than 10 wt % moisture content.

In another embodiment the product and/or feed additive composition and/or premix and/or feedstuff in accordance with the present invention comprises less than 5 wt % moisture content.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "h" or "hr" means hour(s), "min" means minute(s), "s" or "sec" means second(s), "d" means day(s), "L" means liter(s), "mL" means milliliter(s), "µL" means microliter(s), "kg" means kilograms, "g" means grams, "µg" means microgram(s), "ng" means nanogram(s), "mg" means milligrams, "g/L" means grams per liter, "mM" means millimolar, "µM" means micromolar, "nm" means nanometer(s), "mm" means millimeter, "cm" means centimeter(s), "µmol" means micromole(s), "pmol" means picomole(s), "N" means newton(s), "G-force" means force of gravity, "MPa" means megapascals, "kPa" means kilopascals, "psi" means pounds per square inch, "CF" means crystalline fraction, "CDS" means coherent domain size, "F" means force, " " or "in" means inch(s).

General Methods
Cellulosic Biomass

Corn stover was hammer milled to a particle size of $d_{50}$=410 µm. The final moisture content of the stover was 7.7% by weight.

Wood was obtained from Fortress Paper LCC (Thurso Quebec, Canada). It was received in chip form (~0.25-0.5" (0.635-1.27 cm) thick with a width and length from ~0.5-3" (1.27-7.62.cm)) as determined via measurements with a ruler. All of the chips were air dried by spreading 1-2 layers of chips in a pan and letting them dry under ambient conditions for at least two days before any further processing; these chips are identified as "air-dried wood chips." The air-dried wood chips were chopped to pass through a 3/16 inch (0.476 cm) screen and then bantam milled to pass through a 1 mm screen. Post bantam milling, the wood chips were vacuum dried at 70° C. overnight with a nitrogen purge. The bantam milled and vacuum dried chips are referred to herein as "bantam milled-dried wood chips".

Centrifugal Ring and Puck Milling

Cellulosic biomass was treated in a vibratory pulverizer (model VP-1989: 3 phase Vibratory Pulverizer; Bico Inc., Burbank, Calif.); also called a ring and puck mill. The pulverizer consists of a hardened chrome alloy steel bowl (8.125" (20.64 cm) inner diameter), which contains two rings of ½" (1.27 cm) thick hardened steel, one with an inner diameter of 3.06" (7.77 cm) and the other with an inner diameter of 2.05" (5.21 cm) and a solid puck (i.e. disc) with diameter of 1.64" (4.17 cm). The lengths of the rings and puck and corresponding depth of the bowl are 2" (5.08 cm). The bowl containing the rings, puck, and sample were vibrated with a one horsepower eccentric motor at 900 rpm. The radius of eccentricity of the mill is 4.5 mm, which is the radius of the circle that is drawn out by the vibration of the mill. The power of the mill was determined by the using the measured current, applied voltage, and a power factor of 0.8 in the standard equation for a three phase motor.

Moisture Assay

The moisture content of the biomass was measured using a Mettler-Toledo HR73 Halogen Moisture Analyzer. An amount of at least 0.5 g (but less than 3 g) was used for each measurement. Each biomass sample was weighed out into an aluminum pan and heated according to the standard drying program to at temperature of 105° C. Each sample was held at 105° C. until the measured mass loss was <1 mg/50 s, at which point the weight was recorded and the moisture content determined by the ratio of the difference between the initial and final weights to the initial weight of the biomass.

Particle Size Assay

Particle size distribution (PSD) was determined via laser diffraction (reference ISO 13320-1:1999) using a Malvern Mastersizer 2000 (Malvern Instruments, Malvern UK). Sample particles were dispersed in air using a Malvern Scirocco 2000 dry disperser unit with the dispersion jet pressure set to about 60 psi (0.41 MPa) and the feed rate set to about 45% of maximum. The dispersed particles were pneumatically conveyed through the Mastersizer's flow cell, which was outfitted with quartz windows for optical access. Laser light entering the flow cell was diffracted by the particles, and the diffraction pattern was imaged onto an array of detectors. The PSD was calculated by analyzing the recorded diffraction pattern using the Fraunhofer scattering model (described in ISO 13320-1:1999, Annex A). A standard reference for PSD measurement and terminology is T. Allen, Particle Size Measurement, Vol. 1, $5^{th}$ Ed. (Chapman & Hall 1997).

X-Ray Diffraction (XRD) Measurements

X-ray diffraction data were obtained with a Philips X'PERT automated powder diffractometer, Model 3040. The diffractometer is equipped with automatic variable anti-scatter and divergence slits, X'Celerator RTMS detector, and Ni filter. The radiation is CuK(alpha) (45 kV, 40 mA). Data were collected at room temperature from 4 to 80 degrees 2-theta; using a continuous scan with an equivalent step size of 0.02 degrees; and a count time of 80 seconds per step in theta-theta geometry. Samples were packed into an aluminum sample holder and run with no additional grinding. MDI/Jade software version 9.1 was used to remove sharp diffraction peaks from crystalline, inorganic contaminants and to convert the data to text format for further processing. Microsoft® Excel® (2010) software was used for all additional processing.

Background subtraction and determination of the so-called crystallinity index (CrI) were carried out according to methods described by Segal (L. Segal et al., (1959) Textile Research Journal 29: 786-794). This method relies on a ratio of diffracted intensities at two specific two-theta angles to establish a measure of relative crystallinity. A number of authors have attempted to improve on this method. It is desirable to have a more absolute measure of crystallinity, and to allow for swelling of the cellulose lattice, changes in crystallite coherent domain size and two-theta zero offset errors. Bansal et al. ((2010) Bioresource Technology 101, No. 12: 4461-4471) describe a multivariate approach that involves fitting the diffraction pattern as a linear combination of model patterns representing cystalline and amorphous standards. Thygesen et al. ((2005) Cellulose 12:563-576) describe a modified Rietveld refinement which fits the crystalline contribution to the diffraction with a calculated pattern based on the known crystal structure of alpha cellulose and a fitted background representing the amorphous contribution. In either of these methods the crystalline index is the ratio of the area under the crystalline model to the area under the whole diffraction pattern. The Rietveld method has the advantage of allowing for changes in the crystalline lattice. Both swelling from absorption of solvents and reduction of crystallite size can be accommodated and extracted from the modeling as useful data points in and of themselves.

A hybrid method was used in which the Rietveld refinement was carried out on a limited range of two-theta data (10-32 degrees) which has had a linear background subtracted from it as in the Segal method. We base the structural model on the known crystalline structure of alpha cellulose (Y. Nishiyama et al. (2002) J. Am. Chem. Soc. 124, no. 31:9074-9082). Rather than fit an arbitrary function to represent the amorphous contribution, we fit a linearly scaled pattern from a fully amorphous standard. To reduce the number of parameters in our refinement we do not fit the inter axis angles or the c axis of the crystalline lattice. The a and b axes are only fit when crystallinity and coherent domain size are sufficiently large to allow clear resolution of the crystalline peaks. Our reported crystalline fraction (CF) is the ratio of the area under the Rietveld refined crystalline model to the area under the fitted range. Coherent domain size (CDS) is extracted from the refinement (Warren (1969) X-Ray Diffraction; Reading, Mass.; Addison-Wesley) and is the average distance over which the crystalline cellulose is free of structural defects.

This is a method for obtaining cellulose crystalline fraction from X-ray diffraction data in which constrained least squares refinement and an amorphous contribution extracted from a fully amorphous cellulose sample allow for reliable determination of crystalline diffraction peak widths from which cellulose coherent domain size may be calculated. In this process the number of adjustable parameters is reduced through use of a fixed shape for the amorphous fraction and constraints on the calculated crystalline fraction (e.g. crystalline lattice constant is fixed, all diffracted peaks have the same shape and width, and the peak intensity ratios for the crystalline peaks are fixed).

The equation relating peak width to domain size is known as the Scherrer equation: $L=0.94l/(B \cos(q))$, where L is the CDS in angstroms, l is the wavelength in angstroms, q is the diffraction angle of the peak in question and B is the full width at half maximum of that peak in radians.

Compositional Analysis of Cellulosic Biomass

Total carbohydrate of the cellulosic biomass starting material was determined by Microbac Laboratory Services, Boulder, Colo., as well as using a modification of the LAP2 procedure (Sluiter et al. (April 2008; revised Jul. 8, 2011) National Renewable Energy Technical Report NREL/TP-510-42618; revised Jul. 8, 2011. Total carbohydrate of the starting material was averaged between the two techniques to give the total carbohydrate composition of the starting material that was used to calculate sugars yields after saccharification.

Cellulosic biomass compositional analysis was done in duplicate using the following modification of the LAP2 procedure. The solid to be analyzed was either air dried or dried in a vacuum oven at 80° C. until the moisture content was less than 20%. It was then milled in a knife mill until it passed through a 30 mesh screen and/or it was sieved through 20 and 80 mesh screens and the 20-80 mesh fraction was used. The percent solid for the biomass was determined by drying with a halogen moisture analyzer to 105° C. (Mettler Toledo, HR83-P), and then 300 mg (dry weight basis) of the biomass was weighed into a 100 mL glass pressure vessel (Chemglass, CG-1880-05). 3.0 mL of 72 wt % $H_2SO_4$ in water was added to the solid and the mixture was mixed using a 0.25" diameter polytetrafluoroethylene (PTFE) rod to ensure complete coverage of acid on the solid particles. The mixture was submerged in a stirred 30° C. water bath for 30 min. It was then briefly mixed again and put back into the water bath for an additional 30 min. To avoid losses, the PTFE rod remained in the mixture for the first hour. After this initial incubation period, deionized water (84 g) was added to the vessel and it was thoroughly mixed. This method was modified when there was not enough biomass to complete the analysis on the scale described above. In these instances, only 50 mg of solid (dry weight basis) was added to a 15 mL pressure vessel (Chemglass, CG-1880-01) along with 0.5 mL of 72 wt % $H_2SO_4$ in water. This was mixed thoroughly, as described above, and was then incubated at 30° C. for 1 h. An additional 14 mL of water were added and the contents thoroughly mixed.

A sugar recovery standard (SRS) was prepared by weighing glucose, xylose, arabinose and DMSO (as an internal standard) to a bottle and filling it will 100 g of water. 14.0 g of this solution was added to a 15 mL pressure vessel (Chemglass, CG-1880-01) along with 0.5 mL of 72 wt % $H_2SO_4$ in water. This was done in duplicate. A sample of each acidic SRS solution was removed before and after heating and was analyzed by HPLC. After heating, the HPLC areas were less than they were before heating because of sugar degradation during the acid hydrolysis. The area ratios of each sugar were recorded and were used to calculate a unique degradation correction factor for the glucose, xylose and arabinose sugars. The correction factor was applied to the sugars detected in the unknown biomass samples being analyzed during the same experiment in an attempt to adjust for degraded sugars during the procedure.

After the 1 h incubation period at 30° C. and subsequent dilution with water, the pressure vessels were put into an autoclave. The autoclave was rapidly heated to a temperature of 121-126° C. and held there for 60 min after which time it cooled slowly. The samples were pulled from the autoclave after 1.5 h. The temperature of the autoclave cooled to approximately 80° C. at this time. The vessels were then further cooled on ice. A weighed amount of DMSO (internal standard; near 0.8000 g or 0.1000 g in the case of the smaller scale analysis) was added to the sample vessel and the mixture was shaken vigorously. The mixture was filtered from any remaining undisssolved solids through a tared polypropylene filter funnel with a 10 micron polyethylene fritted disc (Chemglass, OP-6602). A portion of the filtrate was collected and analyzed by HPLC. The undissolved solid collected on the fritted disc was washed with a copious amount of water and was dried in a vacuum oven at 80° C. The weight of the washed and dried acid insoluble material was recorded and expressed as wt % lignin. The mole amounts of monomeric carbohydrates solubilized by the compositional analysis process and detected by the HPLC analysis were determined. The mole amounts of each were converted to weights using the molecular weights of the polymer bound sugars (i.e. 132 g/mole for xylose and arabinose as monomeric units in hemicellulose, or 162 g/mole for glucose as the monomeric unit in cellulose). These saccharides were present as polysaccharides in the native biomass, not as monomers, so their molecular weights were assumed to be 18 amu less than the monomeric molecular weight, owing to the loss of one molecule of water for each monomer in the polysaccharide chain. The detected weights of each sugar were then reported as a weight % of the dry biomass.

Enzymatic Saccharification

Samples before or after centrifugal milling were saccharified using Accelerase Trio® (DuPont/Danisco U.S. Inc., Genencor, International, Rochester, N.Y.) at a loading of about 10-20 mg enzyme per g of carbohydrate in 50 mM sodium acetate plus 5 mM $MnCl_2$ buffer, pH 5.0, at a temperature of 48° C. for 72 hr. Reaction samples were made to about 10% solids with a total final mass of 0.5 g in a 15 mm×47 mm Kimax® screw cap glass vial (VWR International, West Chester, Pa.) and a 5/16 in stainless steel ball to aid mixing. The sample vials were then placed in a shaker-incubator set at 180 rpm and 48° C. At the 72 hr endpoint the sample was diluted with 2 mL of pure (Millipore) water and clarified by centrifugation. The reaction was quenched by adding 0.1 mL of the clarified sample to 0.1 mL of 1 M sodium carbonate solution. Before analysis, samples were passed through a Nanosep® MF 0.2 micron centrifugal filter (Pall Life Sciences, Ann Arbor, Mich.) using a Microfuge 18 Centrifuge (Beckman Coulter) set at 13,000 rpm for 3-5 min. Glucose and xylose were measured by HPLC with a Waters Alliance HPLC system. The column used was a Transgenomic® ION-300 column (#ICE-99-9850, Transgenomic, Inc., Ohmaha, Nebr.) with a BioRad Micro-Guard Cartridge Cation-H (#125-0129, Bio-Rad, Hercules, Calif.). The column was run at 75° C. and 0.4 mL/min flow rate using 0.01 N $H_2SO_4$ as solvent. The concentrations of starting sugars and products were determined with a refractive index detector using external standard calibration curves. For total soluble sugar a portion of the clarified sample was diluted 1 to 1 with 4.4% (w/w) sulfuric acid. The resulting solution was autoclaved in a 11 mm×32 mm glass vial with an aluminum seal top (VWR International, West Chester, Pa.) for a total cycle time of 1 hr at 120° C.

HPLC Analysis for Chemical Saccharification

An Agilent 1100 series HPLC equipped with degasser, binary pump, autosampler, column heater and refractive index detector modules was used to analyze glucose and xylose yields. The column used was a Bio-Rad Aminex HPX-87H 300 mm×7.8 mm column (Catalog No. 125-0140) with a 30 mm×4.6 mm Cation-H refill cartridge guard column (Catalog No. 125-0129) held in a stainless steel guard column holder (Catalog No. 125-0131). The column was heated to 65° C.; the guard column was at room temperature. The refractive index detector was using positive polarity and was heated as close to the column temperature as possible, which was 55° C. in this case. 0.01 N sulfuric acid mobile phase was prepared using a 1N sulfuric acid stock solution of sulfuric acid in filtered Millipore water. This solution was pumped through the column at 0.6 ml/min. A 20 μL injection of each analytical sample was initiated for the 60 min run. Quantitation of compounds was performed using internal standards. Analytical samples are prepared by adding DMSO to a final concentration of approximately 10 mg/ml. Samples were filtered through 0.2 micron filters before injection into the HPLC instrument. To determine initial sample compositions, the above stated method was run at least in duplicate, and the measurements were combined with values measured independently by Microbac Laboratories, Inc. (Pittsburgh, Pa.), using the method of least squares.

Specific Energy Calculations

The specific energy used in a destructuring process was calculated by dividing the steady state power output [kW] of the apparatus used by the throughput [kg/s], which gives kWs/kg or kJ/g.

Example 1 Comparative

Sugars Yields from Hammer Milled Corn Stover

Hammer milled corn stover contained 7.7% moisture and particles in the size of about $d_{50}=410$ μm (both measured as described in General Methods). Crystalline fraction and coherent domain size of the hammer milled stover were measured as described in General Methods to be 53% and 3.8 nm, respectively. The hammer milled stover was saccharified as described in General Methods. The enzyme loading and solids content were 10.9 mg enzyme/g carbohydrate and 10.0%, respectively. The total glucose yield, from both soluble monomer and acid hydrolyzed soluble oligomers, was 14.9%. The total xylose yield, from both soluble monomer and acid hydrolyzed soluble oligomers, was 12.1%. The results are summarized in Table 3.

Example 2

Effect of Centrifugal Ring and Puck Milling on Sugars Yields from Hammer Milled Corn Stover About 5 g of hammer milled corn stover with the same properties as described in Example 1 were divided equally in the three spaces between the media in the bowl (i.e. between the bowl and larger ring, between the larger ring and smaller ring, and between the smaller ring and puck) of the vibratory pulverizer (ring and puck mill) described in General Methods for centrifugal milling. The ring and puck mill was run for 5 min, after which the biomass was sieved through a 45 mesh screen and pass through and retained fractions were collected into plastic bags. The throughput for the milling was ~1 g/min or $1.67 \times 10^{-5}$ kg/s, which gives a specific energy input of 0.134 hp/($1.67 \times 10^{-5}$ kg/s) or ~1.68 kWh/kg or ~6.03 kJ/g, which achieved a processed energy equivalency of 65-73%.

The biomass was subjected to forces ranging from 646 to 1,511 N and "G-forces" ranging from 21.5 to 32.3 as calculated and described below.

Dimensions and mass of the media in the ring and puck mill are:

Bowl: 8.125" (20.64 cm) inner diameter, 2" (5.08 cm) depth, 18.80 lbs (8.53 kg)
Large Ring: 6.125" (15.56 cm) inner diameter, 2" (5.08 cm) depth, 0.6" (1.52 cm) thickness, 6.60 lbs (2.99 kg)
Small Ring: 4.1" (10.41 cm) inner diameter, 2" (5.08 cm) depth, 0.6" (1.52 cm) thickness, 4.69 lbs (2.13 kg)
Puck: 3.270" (8.31 cm) diameter, 2" (5.08 cm) depth, 4.49 lbs (2.04 kg)

The ring and puck mill operates at a constant 900 rpm angular frequency. The circle of eccentricity of the motor (i.e. the circumference of the circle drawn out by the motion of the oscillating stage) is 1.11". Equation 1 can be used to calculate the centrifugal force at the interface between any of the media in the mill. The center-of-mass radius is calculated according to Equation 7.

$$r = \frac{\sum_{i}^{n} m_i r_i}{m_{total}} \qquad \text{Equation 7}$$

where n is the number of media, i is the specific index identifying each unique medium, $m_i$ is the specific mass of an indexed medium, $r_i$ is the specific center-of-mass radius of an indexed medium, and $m_{tot}$ is the total or combined mass of all the media. The total mass of the medial is 15.78 lbs (7.16 kg). The center-of-mass radii of the media are found first by setting the center of the milling stage as the origin. Next, the large ring, small ring, and puck are placed into the bowl and pushed to one side, causing the center-of-mass radius for each medium to be offset from the center of the milling stage, as well as the bowl. The circle of eccentricity of the motor (i.e. the circumference of the circle drawn out by the motion of the oscillating stage) is 1.11", which further offsets the center of mass from the center of the milling stage by the radius of the circle (0.18"). The specific center-of-mass radius, $r_i$, for each medium is the distance from the bowl center to the center of each medium, with the addition of 0.18" to account for the motion of the stage. For example, the center-of-mass radius of the puck is 1.40" (5.44 cm), which is found by subtracting the large ring thickness (0.6"; 1.52 cm), small ring thickness (0.6"; 1.52 cm), and puck radius (1.64") from the bowl inner radius (4.0625") and adding 0.18". Lastly, the "g-forces" in the ring and puck mill can be calculated by dividing the centripetal acceleration (i.e. F/m) by the acceleration due to gravity (~9.8 m/s$^2$). Table 1 summarizes the masses, center-of-mass radii, centrifugal forces at the interfaces between the media, and the "g-forces" in the ring and puck mill.

TABLE 1

Parameters of the apparatus used for centrifugal milling

| Interface | Mass [kg] | Center-of-mass radius [m] | Force [N] | "G-force" | Stress [ksi] |
|---|---|---|---|---|---|
| Bowl-Large Ring | 7.16 | 0.024 | 1,511 | 21.5 | 4.93 |
| Large Ring-Small Ring | 4.17 | 0.030 | 1,121 | 27.4 | 5.84 |
| Small Ring-Puck | 2.04 | 0.036 | 646 | 32.3 | 6.92 |

After milling 8 separate batches as described above, representative biomass particle size, moisture content, crystalline fraction, and coherent domain size (as measured according to the General Methods) were 29-68 μm, ~5%, ~58%, and ~1.6 nm, respectively. The results are summarized in Table 2.

The ring and puck milled corn stover was saccharified as described in General Methods. Saccharification of the samples processed as described above was performed with enzyme loading and solids content of about 11 mg enzyme/g carbohydrate and 10%, respectively. The average total glucose yield, from both soluble monomer and acid hydrolyzed soluble glucose oligomers, was 83%. The average total xylose yield, from both soluble monomer and acid hydrolyzed soluble oligomers, was 74%. The results are summarized in Table 3.

Example 3

Effect of Centrifugal Milling on Sugars Yields from Chopped Corn Stover

Approximately 5 g of chopped corn stover with a particle size of >20 mm in one dimension and >100 mm in another dimension, as measured with a ruler, and moisture content of 8.27% were divided equally in the three spaces between the media in the bowl of the ring and puck mill (i.e. between the bowl and larger ring, between the larger ring and smaller ring, and between the smaller ring and puck). Centrifugal milling was performed for 5 min, after which time the biomass was collected from the mill into a plastic bag. The throughput for the milling was ~1 g/min or $1.67 \times 10^{-5}$ kg/s, which leads to a specific energy input of 0.134 hp/(1.67× 10$^{-5}$ kg/s) or ~1.68 kWh/kg or ~6.03 kJ/g, which achieved a processed energy equivalency of 65-73%.

The initial crystalline fraction of the sample was not measured. The forces and "G-forces" applied by the ring and puck mill to the biomass were the same as those calculated and described in Example 2. The resulting material was analyzed as described in General Methods. Four separate samples were milled as described above, yielding representative values for biomass particle size, moisture content, crystalline fraction, and coherent domain size of 79 μm, 4%, 58%, and 2.3 nm, respectively. The results are summarized in Table 2.

The centrifugal milled corn stover was saccharified as described in General Methods. Saccharification was run a total of 6 times using 4 separate samples that were processed as described above, and was performed with enzyme loading and solids content of about 12 mg enzyme/g carbohydrate and 10%, respectively. The average total glucose yield, from both soluble monomer and acid hydrolyzed soluble oligomers, was 96%. The average total xylose yield, from both soluble monomer and acid hydrolyzed soluble oligomers, was 89%. The results are summarized in Table 3.

Example 4

Comparative

Sugars Yields from Bantam Milled Wood Chips

The particle size, moisture content, crystalline fraction and coherent domain size of bantam milled-dried wood chips, described in General Methods, were measured (as in General Methods) giving values of $d_{50}$=362 μm, 2.1%, 94%, and 3.2 nm, respectively. This material was saccharified as described in General Methods. The enzyme loading and solids content were 9.9 mg enzyme/g carbohydrate and 10.3%, respectively. The total glucose yield, from both soluble monomer and acid hydrolyzed soluble oligomers, was 6.8%. The total xylose yield, from both soluble monomer and acid hydrolyzed soluble oligomers, was 8.1%. The results are summarized in Table 3.

Example 5

Effect of Centrifugal Milling on Sugars Yields from Bantam Milled Wood Chips

Either 5 g or 20 g of bantam milled-dried wood chips described in Example 4 were divided equally in the three spaces between the media in the bowl of the ring and puck mill (i.e. between the bowl and larger ring, between the larger ring and smaller ring, and between the smaller ring and puck). Centrifugal milling was performed for 5 min (on 5 g sample) or 20 min (on 20 g samples), after which the biomass was collected from the mill into a plastic bag. The throughput for the milling was ~1 g/min or $1.67 \times 10^{-5}$ kg/s, which leads to a specific energy input of 0.134 hp/(1.67× 10$^{-5}$ kg/s) or ~1.68 kWh/kg or ~6.03 kJ/g, which achieved a processed energy equivalency of 65-73%.

The forces and "g-forces" applied by the puck mill to the biomass were the same as those calculated and described in Example 2. The resulting material was analyzed as described in General Methods. At least four separate samples were milled as described above, yielding representative values for biomass particle size, moisture content, crystalline fraction, and coherent domain size of 19-42 μm, 3%, 65%, and 1.5 nm, respectively. The results are summarized in Table 2.

The resulting material was saccharified as described in General Methods. Saccharification was run a total of 6 times using 4 separate samples processed as described above, and was performed with enzyme loading and solids content of about 10 mg enzyme/g carbohydrate and 10%, respectively. The average total glucose yield, from both soluble monomer and acid hydrolyzed soluble oligomers, was ~81%. The average total xylose yield, from both soluble monomer and acid hydrolyzed soluble oligomers, was ~79%. The results are summarized in Table 3.

Example 6

Effect of Centrifugal Milling on Sugars Yields from Wood Chips 20.032 g of air-dried wood chips with dimensions of about 0.25-0.5" (0.635-1.27 cm) thick and width/length of about 0.5-3" (1.27-7.62 cm), containing 8.1% moisture, were divided equally in the three spaces between the media in the bowl of the ring and puck mill (i.e. between the bowl and larger ring, between the larger ring and smaller ring, and between the smaller ring and puck). Centrifugal milling was performed for 20 min, after which the biomass was collected from the mill into a plastic bag. The throughput for the milling was ~1 g/min or $1.67 \times 10^{-5}$ kg/s, which leads to a specific energy input of 0.134 hp/($1.67 \times 10^{-5}$ kg/s) or ~1.68 kWh/kg or ~6.03 kJ/g, which achieved a processed energy equivalency of 65-73%.

The initial crystalline fraction of the sample was not measured. The forces and "G-forces" applied by the ring & puck mill to the biomass are the same as those calculated and described in Example 2. The resulting material was analyzed as described in General Methods and gave biomass particle size, moisture content, crystalline fraction, and coherent domain size of 95 μm, 6.3%, 77%, and 1.3 nm, respectively. The results are summarized in Table 2.

The resulting material was saccharified as described in General Methods. The enzyme loading and solids content were 10.4 mg enzyme/g carbohydrate and 9.7%, respectively. The total glucose yield, from both soluble monomer and acid hydrolyzed soluble oligomers, was 88.8%. The total xylose yield, from both soluble monomer and acid hydrolyzed soluble oligomers, was 80.8%. The results are summarized in Table 3.

TABLE 2

Properties of centrifugal milled biomass samples in examples 1-6

| | Example # | | | |
|---|---|---|---|---|
| | 2 | 3 | 5 | 6 |
| Initial size [mm] | 0.410 | >20 and >100 each in at least one dimension | 0.362 | Chips (>6.35 × >6.35 × 75.2) |
| Initial moisture [wt %] | 7.7 | 8.3 | 2.1 | 8.1 |
| Initial CF [vol %] | 53% | *NA | 94% | NA |
| Initial CDS [nm] | 3.8 | NA | 3.2 | NA |
| Final size [mm] | 0.029-0.068 | 0.079 | 0.019-0.042 | 0.095 |

TABLE 2-continued

Properties of centrifugal milled biomass samples in examples 1-6

| | Example # | | | |
|---|---|---|---|---|
| | 2 | 3 | 5 | 6 |
| Final moisture [wt %] | 5 | 4 | 3 | 6.3 |
| Final CF [vol %] | 58 | 58 | 65 | 77 |
| Final CDS [nm] | 1.6 | 2.3 | 1.5 | 1.3 |

*NA = not assayed

TABLE 3

Summary of sugars yields from examples 1-6

| Example # | Biomass type | Enzyme Load [mg/mL] | Glucose Yield [%] | Xylose Yield [%] |
|---|---|---|---|---|
| 1 | hammer milled corn stover (hmcs) | 10.9 | 14.9 | 12.1 |
| 2 | Centrifugal milled hmcs | 11.0 ± 0.5 | 83 ± 4 | 74 ± 3 |
| 3 | Centrifugal milled chopped corn stover | 12.0 ± 0.1 | 96 ± 6 | 89 ± 3 |
| 4 | Bantam milled wood chips (bmwc) | 9.9 | 6.8 | 8.1 |
| 5 | Centrifugal milled bmwc | 10.2 ± 0.3 | 81 ± 6 | 79 ± 4 |
| 6 | Centrifugal milled wood chips | 10.4 | 88.8 | 80.8 |

Thus the glucose yield increased from 14.9% for hammer milled corn stover to 83% after centrifugal milling of hammer milled stover. Under the same saccharification conditions, unmilled stover that underwent centrifugal milling yielded 96% glucose.

The glucose yield increased from 6.8% for bantam milled wood chips to 81% after centrifugal milling of bantam milled wood chips. Under the same saccharification conditions, wood chips that underwent centrifugal milling yielded 88.8% glucose.

Example 7—Comparative

Effect of Jet Milling on Sugars Yields from Hammer Milled Corn Stover

Jet Milling Force Calculation

Jet milling of hammer milled corn stover was performed in a Trost Model TX Jet Mill Pulverizer. The corn stover was fed using a Syntron vibratory feeder at a rate of between 1-2 lbs (454-907 g)/h. The milling was performed with two opposing compressed air streams at about 100 psi (689 kPa). Material was passed through the jet mill twice. The material was collected though a cyclone and into a bag. The fines of the bag were also shaken out and mixed with the rest of the material. A diagram of the particles colliding with one another is shown in FIG. 2. To calculate the force of impact between the particles, with reference to FIG. 2, the following assumptions were made:
1) masses m1 and m2 of the particles are equal
2) masses after collision remain unchanged, i.e. m1=m1' and m2=m2'
3) the collision is elastic
4) the time scale, Δt, of the collision is fixed at 1 μs
5) the particles are travelling toward each other in a straight line
6) the speed of each particle is constant at 300 m/s (speed of sound for upper force limit)

The force of the impact can be calculated by focusing on one particle and calculating the rate change of momentum, i.e. F=m|Δv|/Δt, where Δv is the change in velocity before and after collision (e.g. v1-v1'). The magnitude of the force was calculated to be ~1.1 N, as shown in Table 4.

TABLE 4

Assumptions and Calculations of the
Impact Force Between Particles in a Jet Mill

| | |
|---|---|
| Void Fraction | 0.9 |
| Density [g/cm3] | 0.13 |
| particle size [μm] | 300 |
| Volume of 1 particle [cm3] | 1.41E-05 |
| mass of one particle [μg] (m) | 1.84 |
| particle velocity [m/s] | 300 |
| time scale of collision [μs] (Δt) | 1 |
| Force [N] | 1.1 |

Jet Milling/Saccharification 1 kg of hammer milled corn stover, with the same properties as described in Example 1, was jet milled as described in the General Methods section for jet milling. After milling, the biomass particle size, moisture content, crystalline fraction, and coherent domain size were measured (as in General Methods) giving values of 51 μm, 5.3%, 72%, and 2.9 nm, respectively.

The jet milled stover was saccharified as described in General Methods. The enzyme loading and solids content were 10.9 mg enzyme/g carbohydrate and 10.0%, respectively. The total glucose yield, from both soluble monomer and acid hydrolyzed soluble oligomers, was 27.5%. The total xylose yield, from both soluble monomer and acid hydrolyzed soluble oligomers, was 28.1%.

This material had particle size (51 μm) similar to or smaller than the particle sizes of ring and puck milled biomass (29-68 μm in Example 2; 79 μm in Example 3; 95 μm in Example 6), but had much lower yields of glucose and xylose indicating that particle size alone is not the basis for yield.

Example 8

Effect of 1 wt % Ca(OH)$_2$ on Sugars Yields from Centrifugal Milled Corn Stover Hammer milled corn stover was treated in the ring and puck mill under similar conditions to those in Example 2. Specifically, ~5 g batches of hammer milled corn stover with the same properties as described in Example 1 were divided equally in the three spaces between the media in the bowl (i.e. between the bowl and larger ring, between the larger ring and smaller ring, and between the smaller ring and puck) of the vibratory pulverizer (ring and puck mill) described in General Methods for centrifugal milling. The ring and puck mill was run for 5 min, after which the biomass was collected into a plastic bag. The throughput for the milling was ~1 g/min or $1.67 \times 10^{-5}$ kg/s, which leads to a specific energy input of 0.134 hp/($1.67 \times 10^{-5}$ kg/s) or ~1.68 kWh/kg or ~6.03 kJ/g, which achieved a processed energy equivalency of 65-73%.

A total of four batches were run and mixed together to generate a feedstock material for further experimentation. After milling, the biomass particle size, moisture content, crystalline fraction, and coherent domain size were measured (as in General Methods) giving values of 87 μm, 5.4%, 64.6%, and 1.9 nm, respectively. CF and CDS results are summarized in Table 5.

Approximately 1 g (1.049 g) of the ring and puck milled corn stover (5.4% moisture) was mixed with a 0.04 M solution of Ca(OH)$_2$ (3.382 mL) to give a 1 wt % base loading based on dry mass of base+biomass. The mixture was topped with ~10 mL of DI water and stirred for 10-30 sec. The mixture was vacuum filtered and washed with 41 mL of water. The moisture content of the biomass in the wet state, after washing and filtering, was measured as described in the General Methods section to be 65.61%. The moist biomass was saccharified as described in General Methods. The enzyme loading and solids content were 10.8 mg enzyme/g carbohydrate and 10.0%, respectively. The saccharification was done in duplicate, using two separately milled and filtered samples prepared similarly according to this example. The average total glucose yield for the 2 runs, from both soluble monomer and acid hydrolyzed soluble oligomers, was 86.3%±6.8%. The average total xylose yield from the two runs, from both soluble monomer and acid hydrolyzed soluble oligomers, was 78.7%±1.9%. The saccharification results are summarized in Table 6.

Example 9

Effect of 1 wt % CaO on Sugars Yields from Centrifugal Milled Corn Stover

The same ring and puck milled feedstock from Example 8 was used in this example. Approximately 1 g (0.992 g) of the ring and puck milled corn stover (5.4% moisture) was mixed with a 0.05 M solution of CaO (3.381 mL) to give a 1 wt % base loading based on dry mass of base+biomass. The mixture was topped with ~10 mL of DI water and stirred for 10-30 s. The mixture was vacuum filtered and washed with 60 mL of water. The moisture content of the biomass in the wet state, after washing and filtering, was measured as described in the General Methods section to be 60.53%. The moist biomass was saccharified as described in General Methods. The enzyme loading and solids content were 10.8 mg enzyme/g carbohydrate and 10.0%, respectively. The saccharification was done in duplicate, using the two separately milled and filtered samples prepared similarly according to this example. The average total glucose yield from the two runs, from both soluble monomer and acid hydrolyzed soluble oligomers, was 84.9%±7.3%. The total average xylose yield from the two runs, from both soluble monomer and acid hydrolyzed soluble oligomers, was 78.4%±0.0%. The saccharification results are summarized in Table 6.

Example 10

Effect of 1 wt % NaOH on Sugars Yields from Centrifugal Milled Corn Stover

The same ring and puck milled feedstock from Example 8 was used in this example. Approximately 1 g (1.008 g) of the ring and puck milled corn stover (5.4% moisture) was mixed with a 0.07 M solution of NaOH (3.440 mL) to give a 1 wt % base loading based on dry mass of base+biomass. The mixture was topped with ~10 mL of DI water and stirred for 10-30 sec. The mixture was vacuum filtered and washed with 65 mL of water. The moisture content of the biomass in the wet state, after washing and filtering, was measured as described in the General Methods section to be 71.93%. The moist biomass was saccharified as described in General Methods. The enzyme loading and solids content were 10.8 mg enzyme/g carbohydrate and 10.0%, respectively. The saccharification was done in duplicate, using the two separately milled and filtered samples prepared similarly according to this example. The average total glucose yield from the two runs, from both soluble monomer and acid hydrolyzed soluble oligomers, was 86.1%±0.7%. The average total xylose yield from the two runs, from both soluble monomer and acid hydrolyzed soluble oligomers, was 83.1%±0.5%. The saccharification results are summarized in Table 6.

Example 11

Effect of Centrifugal Milling in the Presence of 1 wt % $Ca(OH)_2$ on Sugars Yields 4.960 g of hammer milled corn stover with the same properties as described in Example 1 was combined with 0.051 g of $Ca(OH)_2$ (yielding a base loading of 1.1 wt %) and divided equally in the three spaces between the media in the bowl (i.e. between the bowl and larger ring, between the larger ring and smaller ring, and between the smaller ring and puck) of the vibratory pulverizer (ring and puck mill) described in General Methods for centrifugal milling. The ring and puck mill was run for 5 min, after which the biomass was collected into a plastic bag. The throughput for the milling was ~1 g/min or $1.67 \times 10^{-5}$ kg/s, which leads to a specific energy input of 0.134 hp/($1.67 \times 10^{-5}$ kg/s) or ~1.68 kWh/kg or ~6.03 kJ/g, which achieved a processed energy equivalency of 65-73%.

After milling, the crystalline fraction and coherent domain size were measured (as in General Methods) on triplicate samples giving average values of 54.2%±3.2% and 1.6±0.1 nm, respectively. The final moisture content and particle size were not measured, though the powder appeared similar to those from examples 2, 8, 9, and 10, but had a slightly yellow color. The averaged results from XRD are summarized in Table 5.

After milling, samples of the biomass were washed and vacuum filtered to remove $Ca(OH)_2$ before saccharification. For this specific experiment, samples of about 5 g were each washed with 193 mL of water. The moisture content of the biomass in the wet state, after washing and filtering, was measured as described in the General Methods section to be 68.59%. The moist biomass was saccharified as described in General Methods. The enzyme loading and solids content were 10.0 mg enzyme/g carbohydrate and 10.0%, respectively. The saccharification was done in triplicate on the three separately milled and filtered samples prepared similarly according to this example. The average total glucose yield from the three runs, from both soluble monomer and acid hydrolyzed soluble oligomers, was 87.5%±1.6%. The average total xylose yield from the three runs, from both soluble monomer and acid hydrolyzed soluble oligomers, was 78.0%±0.6%. The saccharification results are summarized in Table 6.

Example 12

Effect of Centrifugal Milling in the Presence of 1 wt % CaO on Sugars Yields 4.963 g of hammer milled corn stover with the same properties as described in Example 1 was combined with 0.051 g of CaO (yielding a base loading of 1.1 wt %) and divided equally in the three spaces between the media in the bowl (i.e. between the bowl and larger ring, between the larger ring and smaller ring, and between the smaller ring and puck) of the vibratory pulverizer (ring and puck mill) described in General Methods for centrifugal milling. The ring and puck mill was run for 5 min, after which the biomass was collected into a plastic bag. The throughput for the milling was ~1 g/min or $1.67 \times 10^{-5}$ kg/s, which leads to a specific energy input of hp/($1.67 \times 10^{-5}$ kg/s) or ~1.68 kWh/kg or ~6.03 kJ/g, which achieved a processed energy equivalency of 65-73%.

After milling, the crystalline fraction and coherent domain size were measured (as in General Methods) on triplicate samples giving averaged values of 54.3%±3.3% and 1.7±0.1 nm, respectively. The final moisture content and particle size were not measured, though the powder appeared similar to those from examples 2, 8, 9, and 10, but had a slightly yellow color. The averaged results from XRD are summarized in Table 5.

After milling, samples of the biomass were washed and vacuum filtered to remove CaO. For this specific experiment, samples of about 5 g were each washed with 200 mL of water. The moisture content of the biomass in the wet state, after washing and filtering, was measured as described in the General Methods section to be 72.56%. The moist biomass was saccharified as described in General Methods. The enzyme loading and solids content were 10.0 mg enzyme/g carbohydrate and 10.0%, respectively. The saccharification was done in triplicate on the three separately milled and filtered samples prepared similarly according to this example. The average total glucose yield from the three runs, from both soluble monomer and acid hydrolyzed soluble oligomers, was 87.6%±2.4%. The average total xylose yield from the three runs, from both soluble monomer and acid hydrolyzed soluble oligomers, was 80.3%±2.9%. The saccharification results are summarized in Table 6.

Example 13

Effect of Centrifugal Milling in the Presence of 1 wt % NaOH on Sugars Yields 4.99 g of hammer milled corn stover with the same properties as described in Example 1 was combined with 0.054 g of NaOH (yielding a base loading of 1.2 wt %) and divided equally in the three spaces between the media in the bowl (i.e. between the bowl and larger ring, between the larger ring and smaller ring, and between the smaller ring and puck) of the vibratory pulverizer (ring and puck mill) described in General Methods for centrifugal milling. The ring and puck mill was run for 5 min, after which the biomass was collected into a plastic bag. The throughput for the milling was ~1 g/min or $1.67 \times 10^{-5}$ kg/s, which leads to a specific energy input of 0.134 hp/($1.67 \times 10^{-5}$ kg/s) or ~1.68 kWh/kg or ~6.03 kJ/g, which achieved a processed energy equivalency of 65-73%.

After milling, the crystalline fraction and coherent domain size were measured (as in General Methods) on triplicate samples giving averaged values of 55.0%±8.2% and 1.7±0.2 nm, respectively. The final moisture content and particle size were not measured, though the powder appeared similar to those from examples 2, 8, 9, and 10, but had a slightly yellow color The XRD results are summarized in Table 5.

After milling, samples of the biomass were washed and filtered to remove NaOH. For this specific example, samples of about 5 g were each washed with 268 mL of water. The moisture content of the biomass in the wet state, after washing and filtering, was measured as described in the General Methods section to be 72.09%. The moist biomass was saccharified as described in General Methods. The enzyme loading and solids content were 10.0 mg enzyme/g carbohydrate and 10.0%, respectively. The saccharification was done in triplicate on the three separately milled and filtered samples prepared similarly according to this example. The average total glucose yield from the three runs, from both soluble monomer and acid hydrolyzed soluble oligomers, was 82.8%±5.8%. The average total xylose yield from the three runs, from both soluble monomer and acid hydrolyzed soluble oligomers, was 74.9%±3.2%. The saccharification results are summarized in Table 6.

TABLE 5

XRD Measurements

| Example # | CF % | CDS [nm] |
|---|---|---|
| 1 | 53 | 3.8 |
| 2 | 58 | 1.6 |
| 8 | 64.6 | 1.9 |
| 9 | 64.6 | 1.9 |
| 10 | 64.6 | 1.9 |
| 11 | 54.2 ± 3.2 | 1.6 ± 0.1 |
| 12 | 54.3 ± 3.3 | 1.7 ± 0.1 |
| 13 | 55.0 ± 8.2 | 1.7 ± 0.2 |

*NA = not assayed

TABLE 6

Summary of sugars yields from base treatment examples

| Example # | Enzyme Load [mg/g glucan + xylan] | Glucose Yield [%] | Xylose Yield [%] |
|---|---|---|---|
| 8 | 10.8 | 80.6 ± 6.3 | 72.6 ± 1.8 |
| 9 | 10.8 | 78.6 ± 6.7 | 72.4 ± 0.0 |
| 10 | 10.8 | 89.1 ± 0.07 | 76.7 ± 0.5 |
| 11 | 10.0 | 87.5 ± 1.6 | 78.0 ± 0.6 |
| 12 | 10.0 | 87.6 ± 2.4 | 80.3 ± 2.9 |
| 13 | 10.0 | 82.8 ± 5.8 | 74.9 ± 3.2 |

Example 14

Saccharification of Biomass Samples Using Acid

Biomass (0.5 g) pretreated using different methods, as indicated below, was mixed with $H_2SO_4$ aqueous solution (1 wt %, 4.5 g) in a 25 mL glass pressure tube at room temperature. The mixture was heated at 120° C. for various time periods. The aqueous phase was monitored by HPLC. The insoluble biomass was washed with 1% $H_2SO_4$ aqueous solution (3 times, 5 mL each) and deionized water (once, 50 mL), then dried in a vacuum oven at 80° C. for mass balance calculation. The washes were added to the first aqueous phase prior to the sugar analysis.

Corn stover that was hammer milled and then treated with centrifugal milling as described in General Methods and Example 2 was treated with $H_2SO_4$ aqueous solution as described above, and samples were taken at times listed in the tables for analysis of sugars and remaining undissolved biomass. Glucose and xylose yield results are given in Table 7. Table 8 gives the solid phase analysis of the biomass. The dissolved biomass was determined by subtracting the remaining insoluble biomass from the starting biomass.

TABLE 7

Glucose and xylose yields in liquid phase of dilute acid hydrolyzed puck-milled corn stover

| Rxn Time (hr) | *% of Glucose | *% of Xylose |
|---|---|---|
| 0.00 | 3.3% | 10.0% |
| 0.50 | 4.5% | 29.7% |
| 1.00 | 5.6% | 46.6% |
| 2.00 | 9.1% | 79.7% |
| 3.00 | 12.6% | 81.1% |
| 4.00 | 13.5% | 85.4% |
| 6.00 | 15.5% | 84.4% |
| 8.00 | 16.7% | 81.3% |

*Relative yield is adjusted by the composition of the corresponding biomass, e.g. 100% relative yield of dissolved glucose equals 39.6 wt % of the biomass; 100% relative yield of dissolved xylose equals 22 wt % of the biomass

TABLE 8

Solid phase analysis of dilute acid hydrolyzed puck-milled corn stover

| Rxn Time (hr) | Biomass Dissolved (gram) | Biomass Left (gram) | Biomass Dissolution based on Mass Loss (wt %) |
|---|---|---|---|
| 0.00 | 0.04 | 0.456 | 8.8% |
| 0.50 | 0.17 | 0.327 | 34.6% |
| 1.00 | 0.19 | 0.312 | 37.6% |
| 2.00 | 0.21 | 0.293 | 41.4% |
| 3.00 | 0.23 | 0.275 | 45.0% |
| 4.00 | 0.22 | 0.277 | 44.6% |
| 6.00 | 0.23 | 0.275 | 45.0% |
| 8.00 | 0.24 | 0.265 | 47.0% |

Corn stover that was hammer milled only as described in Example 1 was treated with $H_2SO_4$ aqueous solution as described above, with samples taken at times listed in the tables for sugar and remaining undissolved biomass analysis. Glucose and xylose yield results are given in Table 9. Table 10 gives the solid phase analysis of the biomass.

TABLE 9

Glucose and xylose yields in liquid phase of dilute acid hydrolyzed hammer-milled corn stover

| Rxn Time (hr) | *% of Glucose | *% of Xylose |
|---|---|---|
| 0.00 | 3.2% | 10.6% |
| 0.50 | 5.9% | 47.6% |
| 1.00 | 8.7% | 72.3% |
| 2.00 | 8.5% | 76.2% |
| 3.00 | 10.0% | 77.0% |
| 6.00 | 10.1% | 78.4% |
| 8.00 | 11.2% | 77.3% |

*Relative yield is adjusted by the composition of the corresponding biomass, e.g. 100% relative yield of dissolved glucose equals 39.6 wt % of the biomass; 100% relative yield of dissolved xylose equals 22 wt % of the biomass

TABLE 10

Solid Phase Analysis of Dilute Acid Hydrolyzed Hammer-milled Corn Stover

| Rxn Time (hr) | Biomass Dissolved (gram) | Biomass Left (gram) | Biomass Dissolution based on Mass Loss (wt %) |
|---|---|---|---|
| 0.00 | 0.04 | 0.46 | 8.0% |
| 0.50 | 0.15 | 0.348 | 30.4% |
| 1.00 | 0.17 | 0.33 | 34.0% |
| 2.00 | 0.19 | 0.312 | 37.6% |
| 3.00 | 0.19 | 0.308 | 38.4% |

TABLE 10-continued

Solid Phase Analysis of Dilute Acid Hydrolyzed Hammer-milled Corn Stover

| Rxn Time (hr) | Biomass Dissolved (gram) | Biomass Left (gram) | Biomass Dissolution based on Mass Loss (wt %) |
|---|---|---|---|
| 4.00 | 0.20 | 0.3 | 40.0% |
| 6.00 | 0.20 | 0.299 | 40.2% |
| 8.00 | 0.21 | 0.292 | 41.6% |

Wood chips that were subjected to centrifugal milling as described in Example 6 were treated with $H_2SO_4$ aqueous solution as described above, with samples taken at times listed in the tables for sugar and remaining undissolved biomass analysis. Glucose and xylose yield results are given in Table 11. Table 12 gives the solid phase analysis of the biomass.

TABLE 11

Glucose and xylose yields in liquid phase of dilute acid hydrolyzed puck-milled wood chips

| Rxn Time (hr) | *% of Glucose | *% of Xylose |
|---|---|---|
| 0.00 | 0.2% | 0.3% |
| 0.50 | 1.0% | 24.6% |
| 1.00 | 2.1% | 48.5% |
| 2.00 | 5.3% | 68.1% |
| 3.00 | 7.5% | 70.9% |
| 4.00 | 9.3% | 65.0% |
| 6.00 | 12.7% | 71.8% |
| 8.00 | 14.6% | 74.6% |

*Relative yield is adjusted by the composition of the corresponding biomass, e.g. 100% relative yield of dissolved glucose equals 39.6 wt % of the biomass; 100% relative yield of dissolved xylose equals 22 wt % of the biomass

TABLE 12

Solid phase analysis of dilute acid hydrolyzed puck-milled wood chips

| Rxn Time (hr) | Biomass Dissolved (gram) | Biomass Left (gram) | Biomass Dissolution based on Mass Loss (wt %) |
|---|---|---|---|
| 0.00 | 0 | 0.53 | 0.0% |
| 0.50 | 0.114 | 0.416 | 22.8% |
| 1.00 | 0.142 | 0.388 | 28.4% |
| 2.00 | 0.168 | 0.362 | 33.6% |
| 3.00 | 0.175 | 0.355 | 35.0% |
| 4.00 | 0.181 | 0.349 | 36.2% |
| 6.00 | 0.201 | 0.329 | 40.2% |
| 8.00 | 0.2 | 0.33 | 40.0% |

Wood chips that were bantam-milled as described in General Methods were treated with $H_2SO_4$ aqueous solution as described above, with samples taken at times listed in the tables for sugar and remaining undissolved biomass analysis. Glucose and xylose yield results are given in Table 13. Table 14 gives the solid phase analysis of the biomass.

TABLE 13

Glucose and xylose yields in liquid phase of dilute acid hydrolyzed hammer-milled wood chips

| Rxn Time (hr) | *% of Glucose | *% of Xylose |
|---|---|---|
| 0.00 | 0.0% | 0.0% |
| 0.50 | 0.4% | 13.2% |
| 1.00 | 0.9% | 35.1% |
| 2.00 | 1.8% | 55.5% |
| 3.00 | 2.8% | 64.0% |
| 6.00 | 3.1% | 64.1% |
| 8.00 | 3.9% | 68.8% |

*Relative yield is adjusted by the composition of the corresponding biomass, e.g. 100% relative yield of dissolved glucose equals 39.6 wt % of the biomass; 100% relative yield of dissolved hemicellulose equals 22 wt % of the biomass.

TABLE 14

Solid phase analysis of dilute acid hydrolyzed bantam-milled wood chips

| Rxn Time (hr) | Biomass Dissolved (gram) | Biomass Left (gram) | Biomass Dissolution based on Mass Loss (wt %) |
|---|---|---|---|
| 0.00 | 0.003 | 0.527 | 0.6% |
| 0.50 | 0.054 | 0.476 | 10.8% |
| 1.00 | 0.099 | 0.431 | 19.8% |
| 2.00 | 0.128 | 0.402 | 25.6% |
| 3.00 | 0.149 | 0.381 | 29.8% |
| 4.00 | 0.155 | 0.375 | 31.0% |
| 6.00 | 0.16 | 0.37 | 32.0% |
| 8.00 | 0.173 | 0.357 | 34.6% |

Example 15

Destructuring in a Centrifugal Force Ring-Roller Mill

Centrifugal force ring-roller mills (cfRRMs) have been described in Perry's Chemical Engineers' Handbook ($8^{th}$ Edition, ch 21 p 60), and can contain a wide variety of dimensions based on the scale of the operation. Dimensions for representative scales of cfRRMs were chosen and the forces and stresses generated for these examples of commercial scale cfRRMs were calculated based on their dimensions and masses. The dimensions, masses, and results are given in Table 15. The mill designs have at least two rollers, each attached to a swinging arm, with the arms attached to a drive shaft. The rollers revolve within a chamber, which causes the rollers to press radially outward against a ring.

TABLE 15

Centrifugal Force Ring-Roller Mill Specifications and Forces

| Parameter | cfRRM-1 | cfRRM-2 | cfRRM-3 | cfRRM-4 |
|---|---|---|---|---|
| RPM | 90 | 150 | 100 | 100 |
| Chamber Diameter [in] | 40 | 40 | 80 | 100 |
| Roller Diameter [in] | 13.3 | 13.3 | 26.7 | 33.3 |
| Roller/Ring Height [in] | 10 | 10 | 20 | 29.2 |
| Roller Density [g/cm3] | 8 | 8 | 8 | 8 |
| Mass of Roller [kg] | 183 | 183 | 1,464 | 3,337 |
| Centrifugal Force [N] | 5512 | 15311 | 108,770 | 309,810 |
| Hertzian Stress (w/o material) [psi] | 8140 | 13566 | 18,046 | 22,557 |
| G Force | 3.07 | 8.53 | 7.57 | 9.47 |

Equation 1 was used to calculate the centrifugal forces in each apparatus. The center-of-mass radii for the rollers were found by first setting the axis along the central drive shaft as the origin. The distances from the center of each roller to the central drive shaft are the center-of-mass radii. They are positioned so that they are against the ring, as well as equidistant from each other along the circumference of the ring (such that the center of mass of the all of the rollers considered together, would align with the central shaft on which they are attached).

The "g-forces" in the centrifugal force roller mill were calculated by dividing the centripetal acceleration (i.e. F/m) by the acceleration owing to gravity (~9.8 m/s$^2$).

Thus biomass treated in the described apparatuses would be subjected to forces of >5000 N and "G-forces" of ~3 G, or forces >15,000 N and "G-forces"<9 G, or forces of >100,00 N and "G-forces" of <8 G, or forces >300,000 N and "G-forces"<10 G.

Equation 3 was used to calculate Hertzian stress. The number used for poison's ratio (v) was 0.3 and the number used for elastic modulus (E) was 2.1*10$^{11}$ Pa. These values were chosen based on assumptions that are generally applied to common metals. These same numbers were used for $v_1$ as well as $v_2$, and for $E_1$ as well as $E_2$. The centrifugal forces calculated and given in Table 15 were used as F. The Ring/Roller Heights given in Table 15 were used as l. For purposes of the calculation, an assumption was made that the roller and ring surfaces were perfect cylinders, while in reality the roller becomes concave and does not present an even line contact with the ring.

For a combined milling system (mill and auxiliary equipment such as blower or classifier), the hp can vary dramatically based on the size of the milling system. The full power capabilities for typical cfRRM systems can be anywhere from ~20 hp up to <5000 hp. Once the mill is operated in the desired force and stress range (>5000 N and >5,000 psi (34.47 MPa)), then the air handling system and classifier are modified to achieve a throughput such that the power draw on the machine divided by the throughput yields a specific energy that is <40% of the total combustible energy of the feed material. All of these running modifications are routine to one of skill in the art. The lignocellulosic biomass product is expected to have a CDS of <2.5 nm, and a saccharification yield that is at least 15% higher than the yield of the material before processing. The specific energy input is expected to be <7.2 kJ/g, which is <40% of the combustible energy of corn stover biomass (~18 kJ/g of dry biomass).

Example 16

Effect of Milling on Dissolution of Biomass in Acidic Sulfolane

A mixture of sulfolane, water, and sulfuric acid (10.0 g; weight percent of each component is shown in Table 16) was added to 15 mL pressure tubes (Chemglass, Inc. CG-1880-01). To the liquid in each tube was added 1.00 g (dry weight basis) of either bantam milled dried wood chips (described in General Methods), or bantam milled dried wood chips that were further processed by centrifugal milling (as described in Example 5). The tubes were sealed and placed in a heated oil bath so that the oil level was near the top of the tubes. The tubes were removed at the times given in Tables 16 and 17, and were immediately cooled in a cold-water bath. Each reaction mixture was then filtered through a 10 micron polyethylene filter frit (Chemglass, Inc. OP-6602-12). The remaining solid on each frit was washed three times with approximately 10 mL portions of 95:5 (w/w) sulfolane:water. The initial filtrate and the filtrates from the washes were collected, weighed, and a sample was analyzed on a calibrated Biorad Aminex® carbohydrate HPX-87H HPLC column (Bio-Rad Company) with a refractive index detector. The filtered solids were then each washed with 100 mL of water, and dried in a vacuum oven at 80° C. overnight. The molar amounts of C5 sugars and C5 sugar byproducts (i.e. xylose, arabinose, and furfural), and C6 sugars and C6 sugar byproducts (i.e. HMF, levoglucosan, and levulinic acid) were detected by HPLC analysis. Analytical results and remaining weight of undissolved biomass for each experiment are shown in Tables 16 and 17; the dissolved biomass was determined by subtracting the remaining dried insoluble biomass weight from the starting biomass weight. The results showed that puck & ring milled bantam milled wood dissolved to a greater extent than wood that was bantam milling alone.

TABLE 16

Solid and liquid phase analysis results for hydrolysis of centrifugal milled bantam milled wood in acidic sulfolane at 120° C.

| Reaction Number | Wt % Biomass | Wt % Sulfolane | Wt % Water | Wt % Sulfuric Acid | Time (h) | Wt % Dissolved Solid | Mol % C5 sugar and C5 sugar byproducts | Mol % C6 sugar and C6 sugar byproducts |
| --- | --- | --- | --- | --- | --- | --- | --- | --- |
| 1a | 9.7% | 80.4% | 9.0% | 0.9% | 0.0 | 8% | 4.1% | 1.9% |
| 2a | 9.7% | 80.3% | 9.1% | 0.9% | 0.5 | 67% | 78.9% | 22.5% |
| 3a | 9.7% | 80.3% | 9.1% | 0.9% | 1.0 | 72% | 81.6% | 30.0% |
| 4a | 9.7% | 80.3% | 9.1% | 0.9% | 2.0 | 79% | 82.2% | 46.2% |
| 5a | 9.7% | 80.4% | 9.0% | 0.9% | 4.0 | 88% | 68.2% | 49.6% |
| 6a | 9.7% | 80.4% | 9.0% | 0.9% | 6.0 | 92% | 48.7% | 51.1% |
| 7a | 9.7% | 80.0% | 9.3% | 1.0% | 8.0 | 95% | 28.0% | 52.6% |

TABLE 17

Solid and liquid phase analysis results for hydrolysis of bantam milled wood in acidic sulfolane at 120° C.

| Reaction Number | Wt % Biomass | Wt % Sulfolane | Wt % Water | Wt % Sulfuric Acid | Time (h) | Wt % Dissolved Solid | Mol % C5 sugar and C5 sugar byproducts | Mol % C6 sugar and C6 sugar byproducts |
| --- | --- | --- | --- | --- | --- | --- | --- | --- |
| 1b | 9.9% | 80.1% | 9.0% | 0.9% | 0.0 | 1% | 0.0% | 0.0% |
| 2b | 10.0% | 80.1% | 9.0% | 0.9% | 0.3 | 45% | 62.3% | 6.0% |

TABLE 17-continued

Solid and liquid phase analysis results for hydrolysis of bantam milled wood in acidic sulfolane at 120° C.

| Reaction Number | Wt % Biomass | Wt % Sulfolane | Wt % Water | Wt % Sulfuric Acid | Time (h) | Wt % Dissolved Solid | Mol % C5 sugar and C5 sugar byproducts | Mol % C6 sugar and C6 sugar byproducts |
|---|---|---|---|---|---|---|---|---|
| 3b | 10.0% | 80.1% | 9.0% | 0.9% | 0.5 | 53% | 74.6% | 5.3% |
| 4b | 9.9% | 80.2% | 9.0% | 0.9% | 0.8 | 56% | 74.2% | 8.0% |
| 5b | 10.0% | 80.1% | 9.0% | 0.9% | 1.0 | 57% | 76.1% | 5.6% |
| 6b | 10.0% | 80.1% | 9.0% | 0.9% | 2.0 | 59% | 87.8% | 8.3% |
| 7b | 10.0% | 80.1% | 9.0% | 0.9% | 4.0 | 65% | 78.1% | 13.3% |
| 8b | 10.0% | 80.1% | 9.0% | 0.9% | 6.0 | 71% | 74.7% | 29.4% |
| 9b | 9.9% | 80.1% | 9.0% | 0.9% | 8.0 | 75% | 61.4% | 29.5% |

Example 17

Compositional Analysis of Various Samples

Analysis of composition was done for the bantam milled dried wood chips, and for the two isolated solid samples from reactions 2a (Tables 16) and 3b (Table 17) using the following procedure (results are shown in Table 18).

The solid to be analyzed was milled in a knife mill until it passed through a 30 mesh screen. The percent solid for each biomass sample was determined by drying, and then the appropriate amount of each was weighed into a glass pressure vessel such that the dry weight was either 300 mg in the case of either the bantam milled dried wood chips, or bantam milled dried wood chips further processed by centrifugal milling. For the remaining solids from reaction 2a and 3b, the amount added to the glass pressure vessels was 50 mg. 72 wt % $H_2SO_4$ in water was added to each solid and the mixtures were individually mixed using a ¼" (0.635 cm) diameter glass rod to ensure complete coverage of acid on the solid particles. The mixtures were allowed to stand at ambient temperature for 30 min, and then submerged in a stirred 30° C. water bath for 45 min. Deionized water (84 g) was added to each vessel.

A sugar recovery standard (SRS) was prepared by weighing glucose, xylose, arabinose and DMSO to a bottle and filling it will 100 g of water. 14.0 g of this solution was added to a 15 mL pressure vessel along with 0.8 g (0.5 mL) of 72 wt % $H_2SO_4$. This was done in duplicate. A sample of each acidic SRS solution was filtered and analyzed by HPLC both before and after heating. The area ratios of each sugar relative to the internal standard were recorded for the two samples before and after heating. These were averaged and then divided by each other to determine the extent of the correction factor that should be applied to the data from the experimental samples to compensate for sugar degradation.

All of the pressure vessels were put into an autoclave. The autoclave was rapidly heated to a temperature of 121-126° C. and held there for 60 min after which time it cooled slowly. The samples were pulled from the autoclave after 1.5 h. The temperature of the autoclave cooled to 82° C. at this time. The vessels were then further cooled on ice. To each vessel (except the SRS vessels) was added a weighed amount of DMSO (internal standard; near 0.8000 g); the mixture was shaken vigorously. Each sample was filtered from any remaining solids through a 10 micron polypropylene frit. A portion of the filtrate was collected and analyzed by HPLC.

TABLE 18

Compositional analysis of the bantam milled dried wood chips and for the remaining solid samples 2a (Table 16) and 3b (Table 17)

| Sample | Wt % Glucan | Wt % Xylan |
|---|---|---|
| Bantam milled dried wood chips | 42.0% | 16.6% |
| Sample 2a, Table X1 | 65.0% | 2.7% |
| Sample 3b, Table X2 | 78.8% | 5.5% |

The weight % glucan and xylan dissolved in the acidic sulfolane in samples 2a and 3b (shown below in Tables 19 and 20) were determined by subtracting the total glucan or xylan by compositional analysis of the remaining solids from the total glucan or xylan of the starting Batum milled dried wood chips.

Example 18

Enzymatic Saccharification of Samples 2a and 3b

The isolated solids from reactions 2a (Table 16) and 3b (Table 17) were saccharified using Accelerase Trio® (Dupont/Danisco U.S. Inc., Genencor, International, Rochester, N.Y.) at a loading of 10 mg enzyme per g of carbohydrate (glucan plus xylan contained in the sample) in 50 mM sodium acetate plus 5 mM $MnCl_2$ buffer (pH=5.0), and at a temperature of 48° C. for 72 h. Total carbohydrate and sugar yields of the samples were determined as described in General Methods.

TABLE 19

Results for weight % of total glucan removed from the starting Bantum milled wood chips from a combination of dissolution into acidic sulfolane for 0.5 h at 120° C. and by saccharification of the remaining solids for 72 hours at 48° C. with Accelerase Trio ® of samples 2a (Table 16) and 3b (Table 17).

| Sample | Wt % Glucan dissolved by sulfolane | Wt % Glucan saccharified from solid | Total Wt % Glucan removed |
|---|---|---|---|
| Sample 2a, Table X1 | 49% | 100% | 100% |
| Sample 3b, Table X2 | 12% | 42% | 49% |

TABLE 20

Results for weight % of total xylan removed from the starting Bantum milled wood chips from a combination of dissolution into acidic sulfolane for 0.5 h at 120° C. and by saccharification of the remaining solids for 72 hours at 48° C. with Accelerase Trio ® of samples 2a (Table 16) and 3b (Table 17).

| Sample | Wt % Xylan dissolved by sulfolane | Wt % Xylan saccharified from solid | Total Wt % Xylan removed |
|---|---|---|---|
| Sample 2a, Table X1 | 95% | 95% | 100% |
| Sample 3b, Table X2 | 85% | 66% | 95% |

The results in Table 19 and Table 20 showed that the amount of sugar dissolved from the biomass is nearly quantitative in the case of puck & ring milled bantam milled wood compared to bantam milled wood.

Example 19

Effects of in-Feed Glycosyl Hydrolase Enzymes on the Digestibility of the Fibre Found in Centrifugal Milled Corn Stover Compared with Jet Milled Corn Stover Using an In-Vitro Model Simulating Upper Tract Digestion in Chickens Materials and Methods
In Vitro Digestions of the Simulated Feed Containing Corn Stover Biomass Material Composition of the in vitro digestion treatments is shown in Table 21. To mimic chicken feed, 70% of the biomass material was mixed with 30% soybean meal (SBM). For biomass samples, two types of upper gastrointestinal (GIT) digestions were carried out. First, samples were prepared for both jet milled (JM) corn stover (see Example 7) and centrifugal milled (CM) corn stover, that were not treated with in-feed glycosyl hydrolase enzyme(s) (samples referred to as 'None'). Centrifugal milled means centrifugal ring and puck milling as taught in the General Methods. Secondly, samples that were treated with the in-feed glycosyl hydrolase enzyme(s) during the uGIT in vitro digestions were prepared.

The in-feed glycosyl hydrolase enzymes) used for this study included Axtra®XB which is a commercial enzyme available from Danisco Animal Nutrition, DuPont and contains endoxylanase and endoglucanase activity, Accellerase® Trio™ which is a commercial enzyme available from Dupont™/Genencor®, Wilmington and contains certain cellulase activities such as endoglucanase activity and beta-glucosidase activity and certain hemi-cellulases activity such as endoxylanase activity and Fab which contains beta-glucosidase activity.

TABLE 21

Composition of the in-vitro digestion treatments.

| Samples Name | Composition of treatment | Physical pretreatment method | Exogenous enzymes |
|---|---|---|---|
| JM - Corn Stover | 70% corn stover + 30% soybean meal | Jet milling | None |
| JM - Corn Stover | 70% corn stover + 30% soybean meal | Jet milling | Axtra ®XB + Fab |
| JM - Corn Stover | 70% corn stover + 30% soybean meal | Jet milling | Accellerase ®Trio ™ |
| CM - Corn Stover | 70% corn stover + 30% soybean meal | Centrifugal milling by the herein described mechanical process | None |
| CM - Corn Stover | 70% corn stover + 30% soybean meal | Centrifugal milling by the herein described mechanical process | Axtra ®XB + Fab |
| CM - Corn Stover | 70% corn stover + 30% soybean meal | Centrifugal milling by the herein described mechanical process | Accellerase ®Trio ™ |

Figure 4:
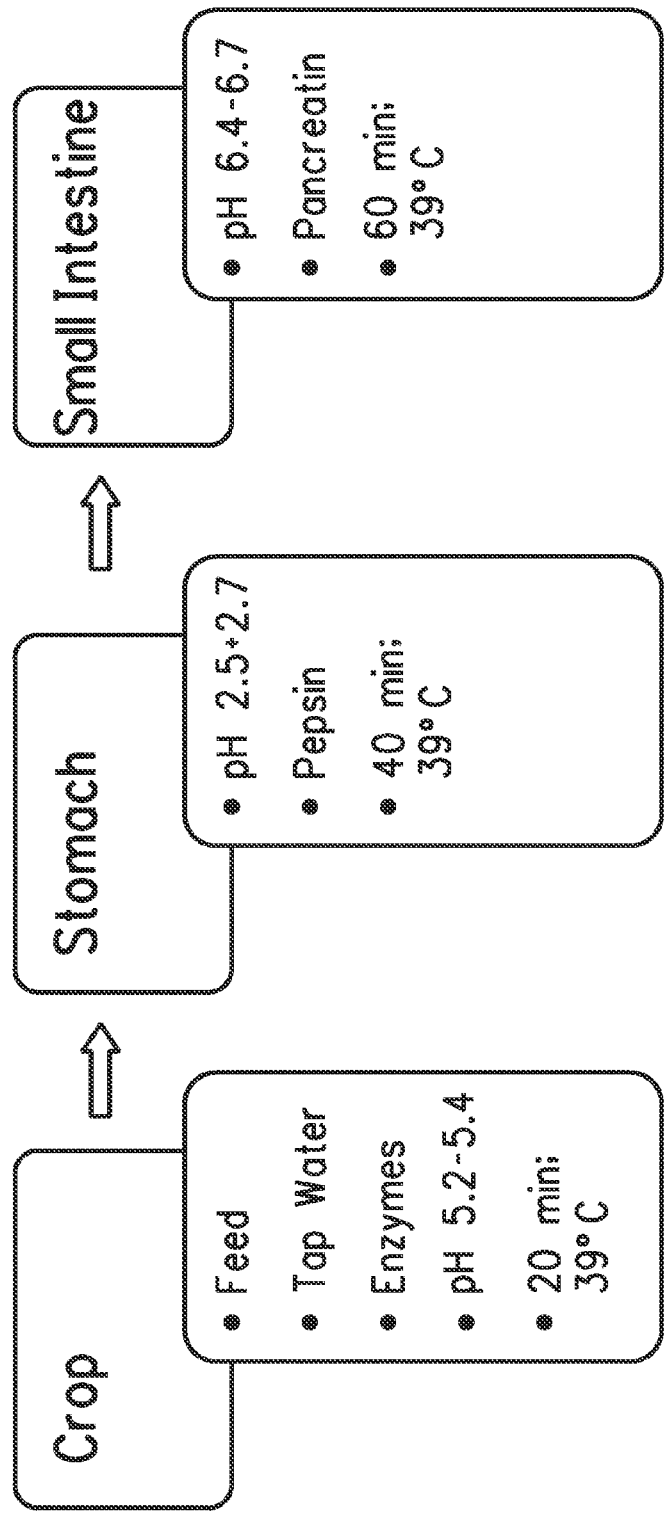
FIG. 4 shows a schematic of the chicken upper GIT in vitro digestion procedure.

The chicken upper GIT in vitro digestion was conducted using the procedure depicted in FIG. 4. A total of three grams of dry matter (DM) was weighed per simulation unit, depending on the target dry matter content (DM % End) during small intestinal digestion step. After mixing the feed with water and adjusting the pH with HCl, in-feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars
Determination of Soluble Sugars after In Vitro Digestion The centrifuged supernatant samples were purified on a C18 solid phase extraction column and the free monosaccharides were analysed with HPLC as described below. Total soluble sugars were determined after acid hydrolysis of the supernatant in 1 M $H_2SO_4$ in an oven at 100° C. for three hours. After dilution with water and filtration, the monosaccharides were analysed by HPLC as described below. The amount of soluble polymeric sugars (oligo- and polysaccharides) in the sample solution was calculated as follows: oligo- and polysaccharides=total soluble sugars− free soluble monosaccharides.

Determination of Monosaccharides by HPLC

The monosaccharides (glucose and xylose) were separated and detected using high pH anion exchange chromatography with pulsed electrochemical detection. The pre-column was CarboPac PA1 (4×40 mm) and the analytical column CarboPac PA1 (4×250 mm). The flow rate was 1 mL/min and the mobile phase consisted of A: water and B: 0.2 M NaOH as the gradient detailed in Table 22:

TABLE 22

Water and NaOH gradient used in the mobile phase of the HPLC method used to determine monosaccharide concentration.

| Time (min) | A (%) | B (%) |
|---|---|---|
| 0 | 90 | 10 |
| 1.1 | 90 | 10 |
| 5 | 100 | 0 |
| 29 | 100 | 0 |
| 30 | 0 | 100 |
| 40 | 0 | 100 |
| 41 | 90 | 107 |
| 58 | 90 | 10 |

Statistical Analyses

The statistical analyses were carried out using One-way ANOVA (Graphpad Prism version 6.01) with Turkey's post-hoc test. The P-value P<0.05 was considered statistically significant.

Mean+SD is shown for all the figures.

Results

The Release of Soluble Sugars from Biomass Materials

The amount of total soluble sugars, free monosaccharides, soluble oligo- and polymeric sugars after in-vitro digestions of jet milled and centrifugally milled corn stover treatments are presented in Tables 23 and 24, respectively. The addition of Axtra®XB in combination with Fab or Accellerase® Trio™ to jet milled corn stover significantly increased the release of total soluble glucose above the control of no enzyme treatment. Centrifugal milling of corn stover (Table 24) improved the response of Accellerase® Trio™ and in particular Axtra®XB+Fab where total release of soluble glucose were boosted by 25% compared to the response in jet milled corn stover.

In the case of total soluble xylose release from jet milled corn stover, the addition of Axtra®XB in combination with Fab or Accellerase® Trio™ significantly increased xylose yield above the negative control (no enzymes). Centrifugal milling of corn stover significantly enhanced the release of total soluble xylose from all treatments including the control (Table 24). Axtra®XB in combination with Fab had significantly higher yields of total soluble xylose than all other treatments in the centrafugally milled corn stover and yields were improved by almost 50% when compared to jet milling.

The release of free soluble glucose was enhanced by all enzyme treatments. Axtra®XB+Fab resulted in the greatest release of glucose followed by Accellerase® Trio™. While centrifugal milling did not substantially boost the release of free glucose compared to jet milling in terms of yield (Table 23), the response of all enzyme treatments was significantly better than the control with Axtra®XB+Fab resulted in the highest glucose yield. Axtra®XB+Fab and Accellerase® Trio™ all enhanced the release of xylose to a similar degree. While centrifugal milling did increase the yield of mono-xylose from corn stover, there were no differences between enzyme treatments tested.

The yield of glucose oligo- and polysaccharides from jet milled corn stovers was not improved by any of the enzymes evaluated. While in the centrifugally milled corn stover, Axtra®XB in combination with Fab significantly improved glucose oligo- and polysaccharide release above all other treatments. Also, the overall yield of glucose oligo- and polysaccharide from all treatments was improved compared to jet milling and in some cases by as much as 20%. There was no effect of enzyme treatment on the release of xylose oligo- and polysaccharides from jet milled corn stovers. Centrifugal milling improved xylose oligo- and polysaccharide release from corn stover compared to jet milling. In particular the effects of Axtra®XB+Fab were enhanced by centrifugal milling resulting in significantly higher xylose oligo- and polysaccharide than all other treatments and up to 35% higher yields than were observed in the jet milled treatments.

TABLE 23

Jet milled corn stover diet (corn stover 70%-SBM 30%): Sugar analysis after in vitro digestions with 3 g (DM) of test material and different treatments.

|  | Glucose | | Xylose | |
|---|---|---|---|---|
|  | % | SD | % | SD |
| Total soluble sugars after digestion | | | | |
| None | 16.7$^b$ | 0.7 | 1.9$^b$ | 0.2 |
| Axtra ® XB + Fab | 34.1$^a$ | 1.3 | 9.4$^a$ | 0.5 |
| Accellerase ® Trio ™ | 31.2$^a$ | 1.0 | 7.3$^a$ | 0.4 |
| Free soluble monosaccharides after digestion | | | | |
| None | 7.8$^c$ | 0.6 | 0.5$^b$ | 0.3 |
| Axtra ® XB + Fab | 25.9$^a$ | 2.1 | 4.5$^a$ | 0.6 |
| Accellerase ® Trio ™ | 22.8$^b$ | 2.2 | 4.1$^a$ | 0.5 |
| Soluble oligo- and polysaccharides after digestion | | | | |
| None | 8.9 | 0.6 | 1.4 | 0.1 |
| Axtra ® XB + Fab | 8.2 | 0.8 | 4.9 | 0.1 |
| Accellerase ® Trio ™ | 8.5 | 1.5 | 3.2 | 0.3 |

$^{a,b}$Mean values within a column with unlike superscript letters were significantly different (P < 0.05; ANOVA followed by Turkey's post hoc test).

TABLE 24

Centrifugal milled corn stover diet (corn stover 70%-SBM 30%): Sugar analysis after in vitro digestions with 3 g (DM) of test material and different treatments.

|  | Glucose | | Xylose | |
|---|---|---|---|---|
|  | % | SD | % | SD |
| Total soluble sugars after digestion | | | | |
| None | 19.1$^c$ | 0.60 | 17.$^c$ | 0.41 |
| Axtra ® XB + Fab | 60.1$^a$ | 2.40 | 61.6$^a$ | 1.38 |
| Accellerase ® Trio ™ | 49.0$^b$ | 2.27 | 48.8$^b$ | 1.17 |
| Free soluble monosaccharides after digestion | | | | |
| None | 3.8$^b$ | 4.53 | 1.5 | 2.54 |
| Axtra ® XB + Fab | 28.7$^a$ | 19.65 | 14.5 | 11.63 |
| Accellerase ® Trio ™ | 20.8$^a$ | 12.92 | 11.0 | 9.57 |
| Soluble oligo- and polysaccharides after digestion | | | | |
| None | 15.3$^b$ | 5.13 | 15.7$^c$ | 2.96 |
| Axtra ® XB + Fab | 31.4$^a$ | 17.53 | 47.2$^a$ | 10.40 |
| Accellerase ® Trio ™ | 28.2$^{ab}$ | 10.96 | 37.7$^{ab}$ | 8.68 |

$^{a,b,c}$Mean values within a column with unlike superscript letters were significantly different (P < 0.05; ANOVA followed by Turkey's post hoc test).

Discussion

While centrifugal milling enhanced the release of both total soluble glucose and xylose from corn stover, the greatest response was observed in xylose release where there was a 15% improvement in yield compared to 3% for glucose. The addition of in-feed enzymes, in particular Axtra®XB+Fab and Accellerase® Trio™ improved the yield of total glucose and xylose in both jet and centrifugal milled corn stover, however; the magnitude of response was far greater as a result of centrifugal milling and for xylose yield.

The enhanced release of total soluble glucose from centrifugal milled corn stover can be explained in part by enhanced mono-glucose release however, the largest improvement can be seen in the release of glucose oligo- and polysaccharides. Likewise, while mono-xylose release was increased through a combination of centrifugal milling and in-feed enzymes, the greatest improvements in yield was observed in the soluble oligo- and polysaccharide fraction.

The combination of endoxylanase and beta-glucanase found in Axtra®XB added in combination with Fab (beta-glucosidase) consistently resulted in the highest yield of both glucose and xylose regardless of sugar unit size particularly in the centrifugal milled corn stover.

Conclusion

Deconstruction of the cellulose fraction of corn stover through centrifugal milling significantly enhanced the release of soluble glucose and xylose by 3 and 15%, respectively compared to particle size reduction alone (jet milling). However, the greatest response was observed when in-feed enzymes were combined with centrifugal milled corn stover where the yield of total soluble glucose and xylose increased by 35 and 50%, respectively.

Example 20

Effects of in-Feed Glycosyl Hydrolase Enzyme(s) on the Digestibility of the Fibre Found in Centrifugal Versus Jet Milled Sugarcane Bagasse Using an In-Vitro Model Simulating Upper Tract Digestion in Chickens Materials and Methods
In Vitro Digestions of the Simulated Feed Containing Sugarcane Bagasse Biomass Material Composition of the in vitro digestion treatments is shown in Table 25. To mimic chicken feed, 70% of the biomass material was mixed with 30% soybean meal (SBM). For biomass samples, two types of upper gastrointestinal (GIT) digestions were done. First, samples were prepared for both jet and centrifugal milled sugarcane bagasse, that were not treated with in-feed glycosyl hydrolase enzyme(s) (samples referred as 'None'). Secondly, samples that were treated with the in-feed glycosyl hydrolase enzyme(s) during the uGIT in vitro digestions were prepared. Centrifugal milled means centrifugal ring and puck milling as taught in the General Methods.

The in-feed glycosyl hydrolase enzyme(s) used for this study included Axtra®XB which is a commercial enzyme available from Danisco (now part of DuPont) and contains endoxylanase and beta-glucanase activity, Accellerase® Trio™ which is a commercial enzyme available from Dupont™/Genencor®, Wilmington and contains certain cellulase activities such as endoglucanase activity and beta-glucosidase activity and certain hemi-cellulases activity such as endoxylanase activity and Fab which contains beta-glucosidase activity.

TABLE 25

Composition of the in-vitro digestion treatments.

| Samples Name | Composition of treatment | Physical pretreatment method | Exogenous enzymes |
|---|---|---|---|
| JM-Sugarcane bagasse | 70% sugarcane bagasse + 30% soybean meal | Jet milling | None |
| JM-Sugarcane bagasse | 70% sugarcane bagasse + 30% soybean meal | Jet milling | Axtra ® XB + Fab |
| JM-Sugarcane bagasse | 70% sugarcane bagasse + 30% soybean meal | Jet milling | Accellerase ® Trio ™ |
| CM-Sugarcane bagasse | 70% sugarcane bagasse + 30% soybean meal | Centrifugal milling | None |
| CM-Sugarcane bagasse | 70% sugarcane bagasse + 30% soybean meal | Centrifugal milling | Axtra ® XB + Fab |
| CM-Sugarcane bagasse | 70% sugarcane bagasse + 30% soybean meal | Centrifugal milling | Accellerase ® Trio ™ |

The chicken upper GIT in vitro digestion was conducted using the procedure as described in Example 19. A total of three grams of dry matter (DM) was weighed per simulation unit, depending on the target dry matter content (DM % End) during small intestinal digestion step. After mixing the feed with water and adjusting the pH with HCl, in-feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars

The methods used to determine the release of soluble sugars are described in Example 19.

Statistical Analyses

The statistical analyses were carried out using One-way ANOVA (Graphpad Prism version 6.01) with Turkey's post-hoc test. The P-value P<0.05 was considered statistically significant. Mean+SD is shown for all the figures.

Results
The Release of Soluble Sugars from Biomass Materials

The amount of total soluble sugars, free monosaccharides, soluble oligo- and polymeric sugars after in-vitro digestions of jet milled and centrifugal milled sugarcane bagasse treatments are presented in Tables 26 and 27, respectively. The addition of Axtra®XB in combination with Fab to jet milled sugarcane bagasse significantly increased the release of total soluble glucose above the control no enzyme treatment. Total glucose release from the Accellerase® Trio™ treatment was not different to all other treatments. Centrifugal milling of sugarcane bagasse (Table 27) improved the response of Accellerase® Trio™ and in particular Axtra®XB+Fab where the yield of total soluble glucose were boosted by 21 and 31% respectively, compared to the response in jet milled sugarcane bagasse.

In the case of total soluble xylose release from jet milled sugarcane bagasse, the addition of Axtra®XB in combination with Fab or Accellerase® Trio™ did not increase the yield of xylose compared to the negative control (no enzymes). Centrifugal milling of sugarcane bagasse significantly enhanced the release of total soluble xylose from all treatments including the control (Table 27). Axtra®XB in combination with Fab had significantly higher yields of total soluble xylose than all other treatments in the centrifugal milled sugarcane bagasse and yields were improved by almost 59% when compared to jet milling. Accellerase® Trio™ also significantly increased the yield of total xylose from centrifugal milled sugarcane bagasse compared to centrifugal milling alone with no enzyme addition.

The release of free soluble glucose from jet milled sugarcane bagasse was enhanced by all enzyme treatments. Axtra®XB+Fab resulted in the greatest release of glucose followed by Accellerase® Trio™. Centrifugal milling substantially boosted the release of free glucose compared to jet milling in terms of yield (up to 22% improvement; Table 26). The response of all enzyme treatments was significantly better than the control with Axtra®XB+Fab resulted in the highest glucose yield. Accellerase® Trio™ also enhanced the release of glucose but to a lesser degree than Axtra®XB+Fab. Both Axtra®XB+Fab and Accellerase® Trio™ addition to jet milled sugarcane bagasse significantly increased free soluble xylose release. Centrifugal milling of sugarcane bagasse alone failed to boost mono-xylose release; however the addition of Axtra®XB+Fab or Accellerase® Trio™ significantly increased yield compared no enzymes by 23.9 and 18.3%, respectively.

The yield of glucose oligo- and polysaccharides from jet milled sugarcane bagasse was not improved by any of the enzymes evaluated. While in the centrifugal milled sugarcane bagasse, Axtra®XB in combination with Fab significantly improved glucose oligo- and polysaccharide release above the control no enzyme treatment, as did the Accellerase® Trio™ treatment. Also, the overall yield of glucose oligo- and polysaccharide from all treatments was improved compared to jet milling and in some cases as much as 9%. There was no effect of enzyme treatment on the release of xylose oligo- and polysaccharides from jet milled sugarcane bagasse. Centrifugal milling improved xylose oligo- and polysaccharide release from sugarcane bagasse compared to jet milling. The effects of Axtra®XB+Fab and Accellerase® Trio™ were enhanced by centrifugal milling resulting in significantly higher xylose oligo- and polysaccharide yields compared to the no enzyme treatment and up to 38% higher yields than were observed in the jet milled treatments.

TABLE 26

Jet milled sugarcane bagasse diet (sugarcane bagasse 70%-SBM 30%): Sugar analysis after in vitro digestions with 3 g (DM) of test material and different treatments.

|  | Glucose | | Xylose | |
| --- | --- | --- | --- | --- |
|  | % | SD | % | SD |
| Total soluble sugars after digestion | | | | |
| None | 8.3$^b$ | 0.12 | 0.7 | 0.01 |
| Axtra ® XB + Fab | 18.5$^a$ | 0.41 | 4.6 | 0.11 |
| Accellerase ® Trio ™ | 16.9$^{ab}$ | 0.39 | 3.5 | 0.05 |
| Free soluble monosaccharides after digestion | | | | |
| None | 0.6$^c$ | 0.07 | 0.0$^b$ | 0.01 |
| Axtra ® XB + Fab | 10.4$^a$ | 0.42 | 2.8$^a$ | 0.05 |
| Accellerase ® Trio ™ | 8.5$^b$ | 0.13 | 2.5$^a$ | 0.05 |
| Soluble oligo- and polysaccharides after digestion | | | | |
| None | 7.8 | 0.15 | 0.7 | 0.03 |
| Axtra ® XB + Fab | 8.0 | 0.61 | 1.8 | 0.15 |
| Accellerase ® Trio ™ | 8.4 | 0.49 | 1.0 | 0.10 |

$^{abc}$Mean values within a column with unlike superscript letters were significantly different (P < 0.05; ANOVA followed by Turkey's post hoc test).

TABLE 27

Centrifugal milled sugarcane bagasse diet (sugarcane bagasse 70%-SBM 30%): Sugar analysis after in vitro digestions with 3 g (DM) of test material and different treatments.

|  | Glucose | | Xylose | |
| --- | --- | --- | --- | --- |
|  | % | SD | % | SD |
| Total soluble sugars after digestion | | | | |
| None | 10.1$^c$ | 0.23 | 14.4$^c$ | 0.48 |
| Axtra ® XB + Fab | 49.5$^a$ | 1.30 | 63.4$^a$ | 1.2 |
| Accellerase ® Trio ™ | 37.9$^b$ | 0.70 | 44.8$^b$ | 0.91 |
| Free soluble monosaccharides after digestion | | | | |
| None | 0.2$^c$ | 0.03 | 0.0$^c$ | 0.02 |
| Axtra ® XB + Fab | 32.3$^a$ | 2.20 | 23.9$^a$ | 3.30 |
| Accellerase ® Trio ™ | 23.2$^b$ | 1.47 | 18.3$^b$ | 0.67 |
| Soluble oligo- and polysaccharides after digestion | | | | |
| None | 9.9$^b$ | 0.24 | 14.4$^c$ | 0.47 |
| Axtra ® XB + Fab | 17.2$^a$ | 1.54 | 39.5$^a$ | 2.96 |
| Accellerase ® Trio ™ | 14.6$^{ab}$ | 2.16 | 26.5$^b$ | 1.22 |

$^{abc}$Mean values within a column with unlike superscript letters were significantly different (P < 0.05; ANOVA followed by Turkey's post hoc test).

Discussion

While centrifugal milling enhanced the release of both total soluble glucose and xylose from sugarcane bagasse, the greatest response was observed in xylose release where there was a 14% improvement in yield compared to 2% for glucose. The addition of the in-feed enzymes, Axtra®XB+Fab and Accellerase® Trio™ improved the yield of total glucose and xylose in both jet and centrifugal milled sugarcane bagasse, The magnitude of response was far greater as a result of centrifugal milling and for xylose yield.

The enhanced release of total soluble glucose from centrifugal milled sugarcane bagasse can be explained in part by enhanced glucose oligo- and polysaccharides release however, the largest improvement can be seen in the release of mono-glucose. While mono-xylose release was increased through a combination of centrifugal milling and in-feed enzymes, the greatest improvements in yield was observed in the soluble oligo- and polysaccharide fraction.

The combination of endoxylanase and endoglucanase found in Axtra®XB added in combination with Fab (beta-glucosidase) consistently resulted in the highest yield of both glucose and xylose regardless of sugar unit size particularly in the centrifugal milled sugarcane bagasse.

Conclusion

Deconstruction of the cellulose fraction of sugarcane bagasse through centrifugal milling significantly enhanced the release of soluble glucose and xylose by 2 and 13%, respectively compared to particle size reduction alone (jet milling). However, the greatest response was observed when in-feed enzymes were combined with centrifugal milled sugarcane bagasse where the yield of total soluble glucose and xylose increased by 40 and 49%, respectively.

Example 21

Effects of in-Feed Glycosyl Hydrolase Enzyme(s) on the Digestibility of the Fibre Found in Centrifugal Versus Jet Milled Soft Wood Using an In-Vitro Model Simulating Upper Tract Digestion in Chickens Materials and Methods In Vitro Digestions of the Simulated Feed Containing Soft Wood Biomass Material Composition of the in vitro digestion treatments is shown in Table 28. To mimic chicken feed, 70% of the biomass material was mixed with 30% soybean meal (SBM). For biomass samples, two types of upper gastrointestinal (GIT) digestions were done. First, samples were prepared for both jet and centrifugal milled soft wood, that were not treated with in-feed glycosyl hydrolase enzyme(s) (samples referred as 'None'). Secondly, samples that were treated with the in-feed glycosyl hydrolase enzyme(s) during the uGIT in vitro digestions were prepared. Centrifugal milled means centrifugal ring and puck milling as taught in the General Methods.

The in-feed glycosyl hydrolase enzyme(s) used for this study included Axtra®XB which is a commercial enzyme available from Danisco (now part of DuPont) and contains endoxylanase and beta-glucanase activity, Accellerase® Trio™ which is a commercial enzyme available from Dupont™/Genencor®, Wilmington and contains certain cellulase activities such as endoglucanase activity and beta-glucosidase activity and certain hemi-cellulases activity such as endoxylanase activity and Fab which contains beta-glucosidase activity.

TABLE 28

Composition of the in-vitro digestion treatments.

| Samples Name | Composition of treatment | Physical pretreatment method | Exogenous enzymes |
|---|---|---|---|
| JM-Soft wood | 70% soft wood + 30% soybean meal | Jet milling | None |
| JM-Soft wood | 70% soft wood + 30% soybean meal | Jet milling | Axtra ® XB + Fab |
| JM-Soft wood | 70% soft wood + 30% soybean meal | Jet milling | Accellerase ® Trio ™ |
| CM-Soft wood | 70% soft wood + 30% soybean meal | Centrifugal milling | None |
| CM-Soft wood | 70% soft wood + 30% soybean meal | Centrifugal milling | Axtra ® XB + Fab |
| CM-Soft wood | 70% soft wood + 30% soybean meal | Centrifugal milling | Accellerase ® Trio ™ |

The chicken upper GIT in vitro digestion was conducted using the procedure as described in Example 19. A total of three grams of dry matter (DM) was weighed per simulation unit, depending on the target dry matter content (DM % End) during small intestinal digestion step. After mixing the feed with water and adjusting the pH with HCl, feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars

The methods used to determine the release of soluble sugars are described in Example 19.

Statistical Analyses

The statistical analyses were carried out using One-way ANOVA (Graphpad Prism version 6.01) with Turkey's post-hoc test. The P-value P<0.05 was considered statistically significant. Mean+SD is shown for all the data.

Results

The Release of Soluble Sugars from Biomass Materials

The amount of total soluble sugars, free monosaccharides, soluble oligo- and polymeric sugars after in vitro digestions of jet milled and centrifugal milled sugarcane bagasse treatments are presented in Tables 29 and 30, respectively. The addition of Axtra®XB in combination with Fab or Accellerase® Trio™ to jet milled soft wood significantly increased the release of total soluble glucose above the control of no enzyme treatment. Centrifugal milling of soft wood (Table 30) improved the response of Accellerase® Trio™ and in particular Axtra®XB+Fab where the yield of total soluble glucose were boosted by 14 and 18% respectively, compared to the response in jet milled soft wood.

In the case of total soluble xylose release from jet milled sugarcane bagasse, the addition of Axtra®XB in combination with Fab or Accellerase® Trio™ did increased the yield of xylose compared to the negative control (no enzymes). Centrifugal milling of sugarcane bagasse significantly enhanced the release of total soluble xylose from all treatments including the control when compared to jet milling (Table 30). Axtra®XB in combination with Fab had significantly higher yields of total soluble xylose than all other treatments in the centrifugal milled soft wood and yields were improved by almost 52% when compared to jet milling.

The release of free soluble glucose from jet milled soft wood was enhanced by all enzyme treatments. Axtra®XB+Fab resulted in the greatest release of glucose followed by Accellerase® Trio™. Centrifugal milling substantially boosted the release of free glucose compared to jet milling in terms of yield due to enhanced enzyme efficacy (up to 18% improvement; Table 30). The response of all enzyme treatments was significantly better than the control with Axtra®XB+Fab resulted in the highest glucose yield. Accellerase® Trio™ also enhanced the release of glucose but to a lesser degree than Axtra®XB+Fab. Both Axtra®XB+Fab and Accellerase® Trio™ addition to jet milled soft wood significantly increased free soluble xylose release. Centrifugal milling of soft wood alone failed to boost mono-xylose release; however the addition of Axtra®XB+Fab or Accellerase® Trio™ significantly increased yield compared with no enzymes by 27.8 and 13%, respectively.

The yield of glucose oligo- and polysaccharides from jet milled soft wood was not improved by any of the enzymes evaluated. While in the centrifugal milled soft wood, Axtra®XB in combination with Fab significantly improved glucose oligo- and polysaccharide release above the control of no enzyme. Also, the overall yield of glucose oligo- and polysaccharide from all treatments was improved compared to jet milling. There was no effect of enzyme treatment on the release of xylose oligo- and polysaccharides from jet milled soft wood. Centrifugal milling improved xylose oligo- and polysaccharide release from soft wood compared to jet milling. The effects of Axtra®XB+Fab and Accellerase® Trio™ were enhanced by centrifugal milling resulting in significantly higher xylose oligo- and polysaccharide yields compared to the no enzyme treatment and up to 27% higher yields than were observed in the jet milled treatments.

TABLE 29

Jet milled soft wood diet (soft wood 70%-SBM 30%):
Sugar analysis after in vitro digestions with 3 g (DM) of test
material and different treatments.

|  | Glucose | | Xylose | |
|---|---|---|---|---|
|  | % | SD | % | SD |
| Total soluble sugars after digestion | | | | |
| None | 8.5$^b$ | 0.12 | 0.5$^b$ | 0.01 |
| Axtra ® XB + Fab | 18.3$^a$ | 0.13 | 5.4$^a$ | 0.09 |
| Accellerase ® Trio ™ | 16.7$^a$ | 0.18 | 4.1$^a$ | 0.06 |
| Free soluble monosaccharides after digestion | | | | |
| None | 0.2$^c$ | 0.20 | 0.0$^c$ | 0.03 |
| Axtra ® XB + Fab | 9.4$^a$ | 0.29 | 3.8$^a$ | 0.19 |
| Accellerase ® Trio ™ | 7.6$^b$ | 0.21 | 3.1$^b$ | 0.29 |
| Soluble oligo- and polysaccharides after digestion | | | | |
| None | 8.3 | 0.21 | 0.4 | 0.03 |
| Axtra ® XB + Fab | 8.9 | 0.34 | 1.6 | 0.28 |
| Accellerase ® Trio ™ | 9.0 | 0.39 | 1.0 | 0.29 |

$^{abc}$Mean values within a column with unlike superscript letters were significantly different (P < 0.05; ANOVA followed by Turkey's post hoc test).

TABLE 30

Centrifugal milled soft wood diet (soft wood 70%-SBM 30%):
Sugar analysis after in vitro digestions with 3 g (DM) of test material
and different treatments.

|  | Glucose | | Xylose | |
|---|---|---|---|---|
|  | % | SD | % | SD |
| Total soluble sugars after digestion | | | | |
| None | 9.9$^c$ | 0.23 | 17.0$^c$ | 0.50 |
| Axtra ® XB + Fab | 41.9$^a$ | 0.71 | 56.8$^a$ | 1.01 |
| Accellerase ® Trio ™ | 30.9$^b$ | 2.66 | 40.7$^b$ | 2.49 |
| Free soluble monosaccharides after digestion | | | | |
| None | 0.4$^c$ | 0.06 | 0.0$^c$ | 0.02 |
| Axtra ® XB + Fab | 27.5$^a$ | 2.71 | 27.8$^a$ | 9.77 |
| Accellerase ® Trio ™ | 18.5$^b$ | 3.50 | 13.0$^b$ | 2.59 |
| Soluble oligo- and polysaccharides after digestion | | | | |
| None | 9.5$^b$ | 0.21 | 17.0$^b$ | 0.51 |
| Axtra ® XB + Fab | 14.5$^a$ | 2.33 | 29.0$^a$ | 8.93 |
| Accellerase ® Trio ™ | 12.4$^{ab}$ | 1.45 | 27.6$^a$ | 1.09 |

$^{abc}$Mean values within a column with unlike superscript letters were significantly different (P < 0.05; ANOVA followed by Turkey's post hoc test).

Discussion

While centrifugal milling enhanced the release of both total soluble glucose and xylose from soft wood, the greatest response was observed in xylose release where there was a 16% improvement in yield compared to 1.5% for glucose. The addition of in-feed enzymes, in particular Axtra®XB+Fab and Accellerase® Trio™ improved the yield of total glucose and xylose in both jet and centrifugal milled soft wood, however; the magnitude of response was far greater as a result of centrifugal milling and for xylose yield.

The enhanced release of total soluble glucose from centrifugal milled soft wood can be explained in part by enhanced glucose oligo- and polysaccharides release however, the largest improvement can be seen in the release of mono-glucose. While soluble oligo- and polysaccharide xylose release was increased through a combination of centrifugal milling and in-feed enzymes, the greatest improvements in yield was observed in the mono-xylose fraction.

The combination of endoxylanase and beta-glucanase found in Axtra®XB added in combination with Fab (beta-glucosidase) consistently resulted in the highest yield of both glucose and xylose regardless of sugar unit size particularly in the centrifugal milled soft wood.

Conclusion

Deconstruction of the cellulose fraction of soft wood through centrifugal milling significantly enhanced the release of soluble glucose and xylose by 1.5 and 16%, respectively compared to particle size reduction alone (jet milling). However, the greatest response was observed when in-feed enzymes were combined with centrifugal milled soft wood where the yield of total soluble glucose and xylose increased by 31 and 39%, respectively.

Example 22

Effects of Saccharification (Referred to in this Example as Pre-Digestion) of Centrifugal Milled Corn Stover with Cellulases (e.g. Cellulase SC) on the Digestibility of the Fibre with and without in-Feed Glycosyl Hydrolase Enzymes Using an In-Vitro Model Simulating Upper Tract Digestion in Chickens Materials and Methods Pre-Digestion of the Simulated Feed Containing Corn Stover Biomass Material Centrifugal milled (CM) corn stover (2.1 g) was weighed into a centrifuge tube with three replicate tubes per each treatment. Tap water was added (13 mL), the components were mixed and pH adjusted to 5.0 with 1 M HCl. The volume in each tube was set equal with water to ensure consistent conditions. To this suspension, 0.145 mL of Cellulase SC (pH 4.4; protein concentration 76.6 g/L) enzyme was added per gram dry matter and mixed thoroughly. The suspensions were incubated at 50° C. for 48 hours with shaking at 200 rpm. The material generated from this process is referred to as pre-digested centrifugal milled corn stover (this is the same as centrifugal milled corn stover biomass hydrolysate).

In Vitro Digestions of the Simulated Feed Containing Corn Stover Biomass Material Composition of the in vitro digestion treatments is shown in Table 31. Both centrifugal milled corn stover that had (pre-digested CM corn stover) or had not (CM corn stover) been saccharified (pre-digested) with Cellulase SC were used in the in-vitro digestions. The pre-digested CM corn stover biomass hydrolysate was in some treatments also treated with in-feed glycosyl hydrolase enzyme(s) during the in-vitro digestion. Centrifugal milled means centrifugal ring and puck milling as taught in the General Methods.

The cellulase used for the saccharification (pre-digestion) of the corn stover is a cellulase called Cellulase SC which contains certain cellulase activities including endoglucanase and beta-glucosidase activity.

The in-feed glycosyl hydrolase enzyme(s) used during the "in-feed" digestion included Axtra®XB which is a commercial enzyme available from Danisco (now part of DuPont) and contains endoxylanase and beta-glucanase activity, Accellerase® Trio™ which is a commercial enzyme available from Dupont™/Genencor®, Wilmington and contains certain cellulase activities such as endoglucanase activity and beta-glucosidase activity and certain hemi-cellulases activity such as endoxylanase activity and Fab which contains beta-glucosidase activity.

TABLE 31

Composition of the in-vitro digestion treatments.

| Samples Name | Composition of treatment | Physical pre-treatment method | Saccharification (Pre-digestion) enzyme | In-feed enzyme |
|---|---|---|---|---|
| CM-Corn Stover | 70% corn stover + 30% soybean meal | Centrifugal milling | None | None |
| Pre-digested CM Corn stover | 70% corn stover + 30% soybean meal | Centrifugal milling | Cellulase SC | |
| Pre-digested CM Corn stover + in-feed enzymes Axtra ® XB + Fab | 70% corn stover + 30% soybean meal | Centrifugal milling | Cellulase SC | Axtra ® XB + Fab |
| Pre-digested CM Corn stover + in-feed enzyme Accellerase ® Trio ™ | 70% corn stover + 30% soybean meal | Centrifugal milling | Cellulase SC | Accellerase ® Trio ™ |

To mimic chicken feed, 70% of the biomass material was mixed with 30% soybean meal (SBM). The chicken upper GIT in vitro digestion was conducted using the procedure outlined in Example 19. A total of three grams of dry matter (DM) was weighed per simulation unit (2.1 g biomass and 0.9 g SBM), depending on the target dry matter content (DM % End) during small intestinal digestion step. After mixing the feed with water and adjusting the pH with HCl, feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars

The methods used to determine the release of soluble sugars are described in Example 19.

Results

The Release of Soluble Sugars from Biomass Materials

The amount of total soluble sugars, free monosaccharides, soluble oligo- and polymeric sugars after in-feed digestions of centrifugal milled (CM) corn stover and predigested CM corn stover are presented in Table 32. Pre-digestion of CM corn stover with Cellulase SC increased the total soluble glucose release compared to material that was not pre-digested (67.9 vs 19.1%). The addition of Axtra®XB in combination with Fab or Accellerase® Trio™ to pre-digested CM corn stover also increased the yield of soluble glucose release to a similar degree.

Similar to what was observed with the release of total soluble glucose, pre-digestion of CM corn stover with Cellulase SC increased the release of total soluble xylose compared to centrifugal milling of corn stover. The addition of Axtra®XB in combination with Fab or Accellerase® Trio™ to pre-digested CM corn stover during in-vitro (in feed) digestion increased total soluble xylose yield above enzyme pre-digestion alone.

The release of free soluble glucose was enhanced by the pre-digestion of CM corn stover with Cellulase SC compared to centrifugal milling alone. However, the addition of Axtra®XB+Fab or Accellerase® Trio™ during in-vitro (in feed) digestion of pre-digested CM corn stover did not greatly increase free soluble glucose release. Free soluble xylose release was enhanced by pre-digestion of CM corn stover with Cellulase SC also. However, unlike what was observed for free soluble glucose, free soluble xylose release was boosted by the addition of Axtra®XB+Fab or Accellerase® Trio™ as an in-vitro (in feed) digestion.

Both Axtra®XB in combination with Fab and Accellerase® Trio™ addition to the in-vitro digestion improved both glucose and xylose oligo- and polysaccharide release.

TABLE 32

Centrifugal milled corn stover diet (corn stover 70%-SBM 30%): Sugar analysis after in vitro digestions with 3 g (DM) of test material and different treatments.

| | Glucose | | Xylose | |
|---|---|---|---|---|
| | % | SD | % | SD |
| Total soluble sugars after digestion | | | | |
| Centrifugal milled (CM) corn stover | 19.1 | 0.6 | 17.2 | 0.4 |
| CM corn stover pre-digested with Cellulase SC (pre-digested CM corn stover) | 67.9 | 28.0 | 40.8 | 20.6 |
| Pre-digested CM corn stover + Axtra ® XB + Fab | 106.7 | 6.0 | 65.6 | 5.8 |
| Pre-digested CM corn stover + Accellerase ® Trio ™ | 106.3 | 5.9 | 64.7 | 6.0 |
| Free soluble monosaccharides after digestion | | | | |
| Centrifugal milled (CM) corn stover | 3.8 | 4.5 | 1.5 | 2.5 |
| CM corn stover pre-digested with Cellulase SC (pre-digested CM corn stover) | 76.7 | 11.0 | 22.5 | 2.9 |
| Pre-digested CM corn stover + Axtra ® XB + Fab | 80.2 | 10.5 | 28.2 | 2.8 |
| Pre-digested CM corn stover + Accellerase ® Trio ™ | 76.5 | 15.4 | 30.4 | 5.6 |
| Soluble oligo- and polysaccharides after digestion | | | | |
| Centrifugal milled (CM) corn stover | 15.3 | 5.1 | 15.7 | 2.9 |
| CM corn stover pre-digested with Cellulase SC (pre-digested CM corn stover) | 6.2 | 10.7 | 18.3 | 20.7 |
| Pre-digested CM corn stover + Axtra ® XB + Fab | 26.5 | 6.6 | 37.4 | 7.6 |
| Pre-digested CM corn stover + Accellerase ® Trio ™ | 29.8 | 12.1 | 34.3 | 10.4 |

Discussion

Pre-digestion of CM corn stover with Cellulase SC for 48 h prior to in feed (in-vitro) digestion substantially boosted the release of glucose compared to centrifugal milling alone and the majority of which was released in monomeric units. The total release of soluble xylose as a result of pre-digestion with Cellulase SC while large, was not as substantial as the glucose release and was divided between both monomer and oligo/polysaccharide release. This outcome is beneficial from an animal feed perspective as monogastric animals readily utilise monomer glucose as an efficient source of energy and the gastrointestinal bacteria can ferment the xylose oligo/polysaccharides to produce short chain fatty acids which are more beneficial to the animal than monomer xylose.

The combination of enzyme pre-digestion and in-feed enzyme digestion as mimicked by the inclusion of enzymes during simulated digestion in the upper GIT of the chicken model enhanced both the release of soluble glucose and xylose. The boost in glucose release came in the form of oligo- and polysaccharides while the xylose boost was in the form of both monomeric and oligo/polymeric subunits.

Conclusion

Enzymatic pre-digestion (saccharification) of corn stover that had already been subjected to cellulose deconstruction by means of centrifugal milling significantly enhanced the release of total soluble glucose and xylose by 48.8 and 23.6%, respectively even compared to centrifugal milling alone. Also, the inclusion of in feed enzymes during in-vitro digestion of the enzymatically pre-digested corn stover was found to enhance further the release of both soluble glucose and xylose. Therefore, the use of centrifugal milling of biomass with enzymatic pre-digestion alone or in combination with in-feed enzymes was found to significantly improve the digestibility of corn stovers for monogastric animals.

Example 23

Effects of Saccharification (Referred to in this Example as Pre-Digestion) of Centrifugal Milled Sugarcane Bagasse with Cellulases (e.g. Cellulase SC) on the Digestibility of the Fibre with and without in-Feed Glycosyl Hydrolase Enzymes Using an In-Vitro Model Simulating Upper Tract Digestion in Chickens Materials and Methods Pre-Digestion of the Simulated Feed Containing Sugarcane Bagasse Biomass Material Centrifugal milled (CM) sugarcane bagasse (2.1 g) was weighed into a centrifuge tube with three replicate tubes per each treatment. Tap water was added (13 mL), the components were mixed and pH adjusted to 5.0 with 1 M HCl. The volume in each tube was set equal with water to ensure consistent conditions. To this suspension, 0.145 mL of Cellulase SC (pH 4.4; protein concentration 76.6 g/L) enzyme was added per gram dry matter and mixed thoroughly. The suspensions were incubated at 50° C. for 48 hours with shaking at 200 rpm. The material generated from this process is referred to as pre-digested centrifugal milled sugarcane bagasse (this is the same as centrifugal milled sugarcane bagasse biomass hydrolysate). Centrifugal milled means centrifugal ring and puck milling as taught in the General Methods.

In Vitro Digestions of the Simulated Feed Containing Sugarcane Bagasse Biomass Material Composition of the in vitro digestion treatments is shown in Table 33. Both centrifugal milled sugarcane bagasse that had (pre-digested CM sugarcane bagasse) or had not (CM sugarcane bagasse) been pre-digested with Cellulase SC were used in the in-vitro digestions. The pre-digested CM sugarcane bagasse was also treated with in-feed glycosyl hydrolase enzyme(s) during the in-vitro digestion.

The cellulase used for the pre-digestion of the sugarcane bagasse is a cellulase called Cellulase SC which contains certain cellulase activities including endoglucanase and beta-glucosidase activity.

The in-feed glycosyl hydrolase enzyme(s) used during the in-vitro digestion included Axtra®XB which is a commercial enzyme available from Dupont™/Genencor®, Wilmington and contains endoxylanase and beta-glucanase activity, Accellerase® Trio™ which is a commercial enzyme available from Danisco (now part of DuPont) and contains certain cellulase activities such as endoglucanase activity and beta-glucosidase activity and certain hemi-cellulases activity such as endoxylanase activity and Fab which contains beta-glucosidase activity.

TABLE 33

Composition of the in-vitro digestion treatments.

| Samples Name | Composition of treatment | Physical pretreatment method | Pre-digestion enzyme | In-feed enzyme |
|---|---|---|---|---|
| CM-Sugarcane bagasse | 70% sugarcane bagasse + 30% soybean meal | Centrifugal milling | None | None |
| Predigested CM Sugarcane bagasse | 70% sugarcane bagasse + 30% soybean meal | Centrifugal milling | Cellulase SC | |
| Predigested CM Sugarcane bagasse + Axtra® XB + Fab | 70% sugarcane bagasse + 30% soybean meal | Centrifugal milling | Cellulase SC | Axtra® XB + Fab |
| Predigested CM Sugarcane bagasse + Accellerase® Trio ™ | 70% sugarcane bagasse + 30% soybean meal | Centrifugal milling | Cellulase SC | Accellerase® Trio ™ |

To mimic chicken feed, 70% of the biomass material was mixed with 30% soybean meal (SBM). The chicken upper GIT in vitro digestion was conducted using the procedure outlined in Example 19. A total of three grams of dry matter (DM) was weighed per simulation unit (2.1 g biomass and 0.9 g SBM), depending on the target dry matter content (DM % End) during small intestinal digestion step. After mixing the feed with water and adjusting the pH with HCl, feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars

The methods used to determine the release of soluble sugars are described in Example 19.

Results

The Release of Soluble Sugars from Biomass Materials

The amount of total soluble sugars, free monosaccharides, soluble oligo- and polymeric sugars after in-vitro digestions of centrifugal milled (CM) sugarcane bagasse and pre-digested CM sugarcane bagasse treatments are presented in Table 34. Pre-digestion (saccharification) of CM sugarcane bagasse with Cellulase SC increased the total soluble glucose release compared to material that was not pre-digested (46.7 vs 10.1%). The addition of in feed Axtra®XB in combination with Fab or Accellerase® Trio™ to pre-digested CM sugarcane bagasse also increased the yield of total soluble glucose release to a similar degree.

Similar to what was observed with the release of total soluble glucose, pre-digestion of CM sugarcane bagasse with Cellulase SC increased the release of total soluble xylose compared to centrifugal milling of sugarcane bagasse. The addition of in feed Axtra®XB in combination with Fab or Accellerase® Trio™ to pre-digested (saccharified) CM sugarcane bagasse during in-vitro digestion increased total soluble xylose yield above enzyme pre-digestion alone.

The release of free soluble glucose was enhanced by pre-digestion of CM sugarcane bagasse with Cellulase SC compared to centrifugal milling alone. However, the addition of in-feed Axtra®XB+Fab or Accellerase® Trio™ during in-vitro digestion of pre-digested CM sugarcane bagasse did not greatly increase free soluble glucose release. Free soluble xylose release was enhanced by pre-digestion of CM sugarcane bagasse with Cellulase SC also. However, unlike what was observed for free soluble glucose, free soluble xylose release was boosted by the addition of in-feed Axtra®XB+Fab or Accellerase® Trio™ to the in-vitro digestion.

Both Axtra®XB in combination with Fab and Accellerase® Trio™ addition in-feed (e.g. to the in-vitro digestion) improved both glucose and xylose oligo- and polysaccharide release.

TABLE 34

Centrifugal milled sugarcane bagasse diet (sugarcane bagasse 70%-SBM 30%): Sugar analysis after in vitro digestions with 3 g (DM) of test material and different treatments.

|  | Glucose | | Xylose | |
|---|---|---|---|---|
|  | % | SD | % | SD |
| Total soluble sugars after digestion | | | | |
| Centrifugal milled (CM) sugarcane bagasse | 10.1 | 0.23 | 14.4 | 0.48 |
| CM sugarcane bagasse pre-digested with Cellulase SC (pre-digested CM sugarcane bagasse) | 46.7 | 2.87 | 32.8 | 1.81 |
| Pre-digested CM sugarcane bagasse + Axtra ® XB + Fab | 95.8 | 4.21 | 71.0 | 3.52 |
| Pre-digested CM sugarcane bagasse + Accellerase ® Trio ™ | 95.9 | 4.38 | 69.9 | 3.53 |
| Free soluble monosaccharides after digestion | | | | |
| Centrifugal milled (CM) sugarcane bagasse | 0.2 | 0.03 | 0.0 | 0.02 |
| CM sugarcane bagasse pre-digested with Cellulase SC (pre-digested CM sugarcane bagasse) | 69.2 | 15.11 | 23.4 | 5.84 |
| Pre-digested CM sugarcane bagasse + Axtra ® XB + Fab | 59.8 | 22.54 | 28.3 | 10.93 |
| Pre-digested CM sugarcane bagasse + Accellerase ® Trio ™ | 75.7 | 10.33 | 37.7 | 5.62 |
| Soluble oligo- and polysaccharides after digestion | | | | |
| Centrifugal milled (CM) sugarcane bagasse | 9.9 | 0.24 | 14.4 | 0.47 |
| CM sugarcane bagasse pre-digested with Cellulase SC (pre-digested CM sugarcane bagasse) | 0.0 | 0.0 | 9.4 | 4.39 |
| Pre-digested CM sugarcane bagasse + Axtra ® XB + Fab | 36.1 | 15.4 | 42.7 | 11.49 |
| Pre-digested CM sugarcane bagasse + Accellerase ® Trio ™ | 20.2 | 9.17 | 32.1 | 5.55 |

Discussion

Pre-digestion (saccharification) of CM sugarcane bagasse with Cellulase SC for 48 h prior to in-feed (in-vitro) digestion substantially boosted the release of glucose compared to centrifugal milling alone and the majority of which was released in monomeric units. The total release of soluble xylose as a result of pre-digestion with Cellulase SC while large, was not as substantial as the glucose release and was divided between both monomer and oligo/polysaccharide release. This outcome is beneficial from an animal feed perspective as monogastric animals readily utilise monomer glucose as an efficient source of energy and the gastrointestinal bacteria can ferment the xylose oligo/polysaccharides to produce short chain fatty acids which are more beneficial to the animal than monomer xylose.

The combination of enzyme pre-digestion and in-feed enzyme digestion as mimicked by the inclusion of enzymes during simulated digestion in the upper GIT of the in vitro chicken model enhanced both the release of soluble glucose and xylose. The boost in glucose release came in the form of oligo- and polysaccharides while the xylose boost was in the form of both monomeric and oligo/polymeric subunits.

Conclusion

Enzymatic pre-digestion (saccharification) of sugarcane bagasse that had already been subjected to cellulose deconstruction by means of centrifugal milling significantly enhanced the release of total soluble glucose and xylose by 36.6 and 22.4%, respectively compared to centrifugal milling alone. Also, the inclusion of in-feed enzymes during simulated digestion (e.g. in the in-vitro digestion model) of the enzymatically pre-digested (saccharified) sugarcane bagasse was found to enhance the release of both soluble glucose and xylose. Therefore, the use of centrifugal milling of biomass with enzymatic pre-digestion alone or in combination with in-feed enzymes was found to significantly improve the digestibility of sugarcane bagasse for monogastric animals.

Example 24

Effects of Saccharification (Referred to in this Example as Pre-Digestion) of Centrifugal Milled Soft Wood with Cellulases (e.g. Cellulase SC) on the Digestibility of the Fibre with and without in-Feed Glycosyl Hydrolase Enzyme(s) Using an In-Vitro Model Simulating Upper Tract Digestion in Chickens Materials and Methods Pre-Digestion of the Simulated Feed Containing Soft Wood Biomass Material Centrifugal milled (CM) soft wood (2.1 g) was weighed into a centrifuge tube with three replicate tubes per each treatment. Tap water was added (13 mL), the components were mixed and pH adjusted to 5.0 with 1 M HCl. The volume in each tube was set equal with water to ensure consistent conditions. To this suspension, 0.145 mL of Cellulase SC (pH 4.4; protein concentration 76.6 g/L) enzyme was added per gram dry matter and mixed thoroughly. The suspensions were incubated at 50° C. for 48 hours with shaking at 200 rpm. The material generated from this process is referred to as pre-digested centrifugal milled soft wood (this is the same as centrifugal milled soft wood biomass hydrolysate). Centrifugal milled means centrifugal ring and puck milling as taught in the General Methods.

In Vitro Digestions of the Simulated Feed Containing Soft Wood Biomass Material

Composition of the in vitro digestion treatments is shown in Table 35. Both centrifugal milled soft wood that had (pre-digested CM soft wood) or had not (CM soft wood) been pre-digested (saccharified) with cellulases (e.g. Cellulase SC) were used in the in-vitro in-feed digestions. The pre-digested CM soft wood was treated with in-feed glycosyl hydrolase enzyme(s) during the in-vitro digestion model.

The cellulase used for the pre-digestion of the soft wood is a cellulase called Cellulase SC which contains certain cellulase activities including endoglucanase and beta-glucosidase activity.

The in-feed glycosyl hydrolase enzyme(s) used during the in-vitro digestion model included Axtra®XB which is a commercial enzyme available from Danisco (now part of DuPont) and contains endoxylanase and beta-glucanase activity, Accellerase® Trio™ which is a commercial enzyme available from Dupont™/Genencor®, Wilmington and contains certain cellulase activities such as endoglucanase activity and beta-glucosidase activity and certain hemi-cellulases activity such as endoxylanase activity and Fab which contains beta-glucosidase activity.

TABLE 35

Composition of the in-vitro digestion treatments.

| Samples Name | Composition of treatment | Physical pretreatment method | Pre-digestion enzyme | In-feed enzyme |
|---|---|---|---|---|
| CM-Soft wood | 70% soft wood + 30% soybean meal | Centrifugal milling | None | None |
| Predigested CM Soft wood | 70% soft wood + 30% soybean meal | Centrifugal milling | Cellulase SC | |
| Predigested CM Soft wood + Axtra ® XB + Fab | 70% soft wood + 30% soybean meal | Centrifugal milling | Cellulase SC | Axtra ® XB + Fab |
| Predigested CM Soft wood + Accellerase ® Trio ™ | 70% soft wood + 30% soybean meal | Centrifugal milling | Cellulase SC | Accellerase ® Trio ™ |

To mimic chicken feed, 70% of the biomass material was mixed with 30% soybean meal (SBM). The chicken upper GIT in vitro digestion was conducted using the procedure outlined in Example 19. A total of three grams of dry matter (DM) was weighed per simulation unit (2.1 g biomass and 0.9 g SBM), depending on the target dry matter content (DM % End) during small intestinal digestion step. After mixing the feed with water and adjusting the pH with HCl, feed enzymes, Axtra®XB, Accellerase® Trio™ and Fab were dosed at 0.1 mL/g DM, 0.2 mL/g DM, and 0.05 mL/g DM, respectively. At the end of in vitro digestion, liquid phase was separated by centrifugation at 30 000×g for 30 minutes (10° C.), and stored at −20° C. until analysed for soluble carbohydrate composition.

Assessment of the Release of Soluble Sugars

The methods used to determine the release of soluble sugars are described in Example 19.

Results

The Release of Soluble Sugars from Biomass Materials

The amount of total soluble sugars, free monosaccharides, soluble oligo- and polymeric sugars after in-vitro digestions of centrifugal milled (CM) soft wood and pre-digested CM soft wood treatments are presented in Table 36. Pre-digestion of CM soft wood with Cellulase SC increased the total soluble glucose release compared to material that was not pre-digested (64.4 vs 9.9%). The addition of in-feed Axtra®XB in combination with Fab or Accellerase® Trio™ to pre-digested (saccharified) CM soft wood also increased the yield of total soluble glucose release to a similar degree.

Similar to what was observed with the release of total soluble glucose, pre-digestion of CM soft wood with Cellulase SC increased the release of total soluble xylose compared to centrifugal milling of soft wood. The addition of Axtra®XB in combination with Fab or Accellerase® Trio™ to pre-digested CM soft wood during in-vitro digestion increased total soluble xylose yield above enzyme pre-digestion alone.

The release of free soluble glucose was enhanced by pre-digestion of CM soft wood with Cellulase SC compared to centrifugal milling alone. However, the addition of Axtra®XB+Fab or Accellerase® Trio™ during in-vitro digestion of pre-digested CM soft wood did not greatly increase free soluble glucose release. Free soluble xylose release was enhanced by pre-digestion of CM soft wood with Cellulase SC also. However, unlike what was observed for free soluble glucose, free soluble xylose release was boosted by the addition of Axtra®XB+Fab or Accellerase® Trio™ to the in-vitro digestion.

Both Axtra®XB in combination with Fab and Accellerase® Trio™ addition to the in-vitro digestion improved both glucose and xylose oligo- and polysaccharide release.

TABLE 36

Centrifugal milled soft wood diet (soft wood 70%-SBM 30%): Sugar analysis after in vitro digestions with 3 g (DM) of test material and different treatments.

| | Glucose | | Xylose | |
|---|---|---|---|---|
| | % | SD | % | SD |
| Total soluble sugars after digestion | | | | |
| Centrifugal milled (CM) soft wood | 9.9 | 0.23 | 17.0 | 0.50 |
| CM soft wood pre-digested with Cellulase SC (pre-digested CM soft wood) | 64.4 | 31.6 | 43.8 | 18.81 |
| Pre-digested CM soft wood + Axtra ® XB + Fab | 98.6 | 3.41 | 71.3 | 12.98 |
| Pre-digested CM soft wood + Accellerase ® Trio ™ | 97.8 | 1.66 | 70.9 | 12.12 |
| Free soluble monosaccharides after digestion | | | | |
| Centrifugal milled (CM) soft wood | 0.4 | 0.06 | 0.0 | 0.02 |
| CM soft wood pre-digested with Cellulase SC (pre-digested CM soft wood) | 76.7 | 10.28 | 25.3 | 3.27 |
| Pre-digested CM soft wood + Axtra ® XB + Fab | 81.0 | 6.89 | 35.3 | 1.07 |
| Pre-digested CM soft wood + Accellerase ® Trio ™ | 81.8 | 4.27 | 33.8 | 0.46 |
| Soluble oligo- and polysaccharides after digestion | | | | |
| Centrifugal milled (CM) soft wood | 9.5 | 0.21 | 17.0 | 0.51 |
| CM soft wood pre-digested with Cellulase SC (pre-digested CM soft wood) | 4.7 | 8.17 | 18.5 | 16.88 |
| Pre-digested CM soft wood + Axtra ® XB + Fab | 17.6 | 5.91 | 35.9 | 14.04 |
| Pre-digested CM soft wood + Accellerase ® Trio ™ | 16.0 | 2.62 | 37.1 | 11.99 |

Discussion

Pre-digestion of CM soft wood with Cellulase SC for 48 h prior to in-vitro digestion substantially boosted the release of glucose compared to centrifugal milling alone and the majority of which was released in monomeric units. The total release of soluble xylose as a result of pre-digestion with Cellulase SC while large, was not as substantial as the glucose release and was divided between both monomer and oligo/polysaccharide release. This outcome is beneficial from an animal feed perspective as monogastric animals readily utilise monomer glucose as an efficient source of energy and the gastrointestinal bacteria can ferment the xylose oligo/polysaccharides to produce short chain fatty acids which are more beneficial to the animal than monomer xylose.

The combination of enzyme pre-digestion and in-feed enzyme digestion as mimicked by the inclusion of enzymes during simulated digestion in the upper GIT of the chicken model enhanced both the release of soluble glucose and xylose. The boost in glucose release came in the form of oligo- and polysaccharides while the xylose boost was in the form of both monomeric and oligo/polymeric subunits.

Conclusion

Enzymatic pre-digestion of soft wood that had already been subjected to cellulose deconstruction by means of centrifugal milling significantly enhanced the release of total soluble glucose and xylose by 53.3 and 26.8%, respectively compared to centrifugal milling alone. Also, the inclusion of in-feed enzymes during in-vitro digestion of the enzymatically pre-digested soft wood was found to enhance the release of both soluble glucose and xylose. Therefore, the use of centrifugal milling of biomass with enzymatic pre-digestion alone or in combination with in-feed enzymes was found to significantly improve the digestibility of soft wood for monogastric animals.

What is claimed is:

1. A process for producing destructured cellulosic biomass comprising:
   a) providing a portion of cellulosic biomass having a moisture content of less than 30% by weight relative to the total weight of the biomass; and
   b) applying to the biomass of (a) at least one set of compression and impact forces totaling at least 5,000 N and combined with shearing forces, wherein the compression and impact forces comprise compressing or impacting the biomass of (a) against at least one surface by use of at least one milling media;
   wherein a contact stress of greater than 5,000 psi is applied to the biomass, wherein specific energy input in the process is less than 40% of the total combustible energy of the portion of biomass being treated and wherein a destructured cellulosic biomass is produced.

2. The process of claim 1 wherein G-force is applied at less than 10 G.

3. The process of claim 1 wherein the forces are imparted using a non-vibratory apparatus which does not contain free flowing media.

4. A process for producing destructured cellulosic biomass comprising:
   a) providing a portion of cellulosic biomass having a moisture content of less than 30% by weight relative to the total weight of the biomass; and
   b) applying to the biomass of (a) at least one set of compression and impact forces totaling at least 1,500 N and combined with shearing forces, and wherein a contact stress of greater than 5,000 psi is applied and the compression and impact forces comprise compressing or impacting the biomass of (a) against at least one surface by use of at least one milling media;
   wherein specific energy input in the process is less than 40% of the total combustible energy of the portion of biomass being treated and wherein a destructured cellulosic biomass is produced.

5. The process of claim 1 or 4 wherein the biomass of (a) is contacted with a pretreatment chemical prior to, during, or after (b).

6. The process of claim 4 wherein the compression and impact forces are at least 3,000 N.

7. The process of claim 1 or 4 wherein the forces are imparted by centrifugal motion, hydraulics, or springs.

8. The process of claim 1 or 4 further comprising contacting the destructured biomass with at least one saccharification enzyme or saccharification chemical under suitable conditions for saccharification wherein sugars are produced.

9. The process of claim 1 or 4 further comprising admixing the destructured biomass with at least one in-feed glycosyl hydrolase enzyme.

10. The process of claim 1 or 4 wherein the destructured biomass has a coherent domain size that is less than about 2.5 nm.

11. The process of claim 1 or 4 wherein each individual application of force occurs in less than ten milliseconds.

12. The process of claim 1 or 4 wherein compression and impact forces applied to the biomass are applied by smooth surfaces.

13. The process of claim 1 or 4 wherein at least one set of compression and impact forces is at least about 10,000 N.

14. The process of claim 1 or 4 wherein the compression and impact forces are applied to a biomass having a particle size of at least 0.635 cm in at least one dimension.

15. The process of claim 1 or 4 wherein the biomass is selected from the group consisting of corn stover, corn cob, corn grain fiber, grasses, beet pulp, wheat straw, wheat chaff, oat straw, barley straw, barley hulls, hay, rice straw, rice hulls, switchgrass, *miscanthus*, cord grass, reed canary grass, waste paper, sugar cane bagasse, sorghum bagasse, sorghum stover, soybean stover, components obtained from milling of grains, trees, branches, roots, leaves, wood chips, sawdust, palm waste, shrubs and bushes, vegetables, fruits, flowers and animal manure.

16. The process of claim 1 or 4 further comprising contacting the destructed biomass with the least one saccharification enzyme or saccharification chemical under suitable conditions for saccharification wherein sugars are produced, wherein the combined sugars yield of glucose and glucose oligomers and of xylose and xylose oligomers is at least about 15% greater on a total possible sugars yield basis compared to the yield from the biomass of (a) that does not have forces applied as in (b).

17. The process of claim 1 or 4 wherein the contact stress is greater than about 8,000 psi.

18. The process of claim 17 wherein the contact stress is greater than about 25,000 psi.

19. The process of claim 7 wherein the forces are imparted by centrifugal motion and the Radii Ratio is less than 0.5.

20. The process of claim 7 wherein the compression and impact forces are imparted by centrifugal motion by moving an object with a mass of at least 100 kilograms.

21. The process of claim 19 wherein the forces are imparted by centrifugal motion and the Radii Ratio is less than 0.4.

22. The process of claim 21 wherein the forces are imparted by centrifugal motion and the Radii Ratio is about 0.33.

23. The process according to claim 8 wherein the at least one saccharification enzyme comprises at least the following activities endoglucanase activity and β-glucosidase activity.

24. The process of claim 8 wherein the sugar produced comprise glucose, glucose oligomers, xylose and xylose oligomers, and the combined yield of glucose, glucose oligomers, xylose, and xylose oligomers is at least about 50% of total possible yield of these sugars.

25. The process of claim 8 wherein the at least one saccharificaiton enzyme is a saccharification enzyme consortium including at least one glycosidase.

26. The process of claim 8 wherein the saccharification chemical is a mineral acid or an organic solvent.

27. The process of claim 8 further comprising fermenting fermentable sugars produced using a biocatalyst to produce a target compound.

28. The process of claim 8 wherein the biomass of (a) is contacted with a pretreatment chemical prior to, during, or after (b).

29. The process of claim 27 further comprising admixing the destructured biomass with the least one in-feed glycosyl hydrolase enzyme.

30. The process of claim 9 wherein said at least one in-feed glycosyl hydrolase enzyme(s) comprises at least the following enzyme activities: cellulase activity and hemicellulase activity.

31. The process of claim 9 wherein said at least one in-feed glycosyl hydrolase enzyme(s) comprises at least the following enzyme activities:
endoglucanase activity, endoxylanase activity and β-glucosidase activity.

32. The process according to claim 31 wherein the at least one in-feed glycosyl hydrolase enzyme(s) comprises a further enzyme comprising one or both of the following activities: exoglucosidase activity and/or lytic polysaccharide monooxygenase activity.

33. The process of claim 24 wherein the yield of glucose and glucose oligomers is at least 60% based on total possible yield of these sugars.

34. The process of claim 24 wherein the yield of xylose and xylose oligomers is at least 60% based on total possible yield of these sugars.

35. The process of claim 24 wherein the yield of glucose and glucose oligomers is at least 60% and the yield of xylose and xylose oligomers is at least 60% based on total possible yield of these sugars.

36. The process of claim 13 wherein at least one set of compression and impact forces is at least about 50,000 N.

37. The process of claim 36 wherein at least one set of compression and impact forces is at least about 100,000 N.

38. The process of claim 27 where in the target compound comprises ethanol.

39. The process of claim 28 further comprising fermenting fermentable sugars produced using a biocatalyst to produce a target compound.

40. The process of claim 39 wherein the target compound comprises ethanol.

* * * * *